United States Patent
Schnorr et al.

(10) Patent No.: US 10,829,751 B2
(45) Date of Patent: *Nov. 10, 2020

(54) POLYPEPTIDES HAVING LYSOZYME ACTIVITY AND POLYNUCLEOTIDES ENCODING SAME

(71) Applicant: Novozymes A/S, Bagsvaerd (DK)

(72) Inventors: Kirk Matthew Schnorr, Holte (DK); Jens Erik Nielsen, Farum (DK); Mikkel Klausen, Copenhagen (DK)

(73) Assignee: Novozyems A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/140,941

(22) Filed: Sep. 25, 2018

(65) Prior Publication Data

US 2019/0153415 A1    May 23, 2019

Related U.S. Application Data

(62) Division of application No. 15/606,031, filed on May 26, 2017, now Pat. No. 10,119,130, which is a division of application No. 14/360,529, filed as application No. PCT/EP2012/073483 on Nov. 23, 2012, now Pat. No. 9,701,952.

(60) Provisional application No. 61/564,372, filed on Nov. 29, 2011.

(30) Foreign Application Priority Data

Nov. 25, 2011 (EP) ..................... 11190690

(51) Int. Cl.
| | | |
|---|---|---|
| *C12N 9/24* | (2006.01) | |
| *A23K 20/184* | (2016.01) | |
| *C12N 9/36* | (2006.01) | |
| *A23K 40/25* | (2016.01) | |
| *A23K 40/20* | (2016.01) | |
| *C11B 1/10* | (2006.01) | |
| *A23K 20/174* | (2016.01) | |
| *A23K 20/20* | (2016.01) | |
| *A23K 50/75* | (2016.01) | |
| *A23K 50/80* | (2016.01) | |
| *C11D 3/386* | (2006.01) | |
| *C12N 15/10* | (2006.01) | |
| *A23K 20/189* | (2016.01) | |
| *A61K 38/00* | (2006.01) | |

(52) U.S. Cl.
CPC .......... *C12N 9/2462* (2013.01); *A23K 20/174* (2016.05); *A23K 20/184* (2016.05); *A23K 20/189* (2016.05); *A23K 20/20* (2016.05); *A23K 40/20* (2016.05); *A23K 40/25* (2016.05); *A23K 50/75* (2016.05); *A23K 50/80* (2016.05); *C11B 1/102* (2013.01); *C11D 3/38636* (2013.01); *C12N 15/1003* (2013.01); *C12Y 302/01017* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,355,022 A | 10/1982 | Rabussy | |
| 5,041,236 A | 8/1991 | Carpenter et al. | |
| 5,376,288 A | 12/1994 | Falholt | |
| 6,710,023 B1 | 3/2004 | Bodet | |
| 7,635,470 B2 | 12/2009 | Wu | |
| 9,663,775 B2 | 5/2017 | Schnorr | |
| 9,701,952 B2 * | 7/2017 | Schnorr | C12N 9/2462 |
| 10,039,300 B2 | 8/2018 | Schnorr | |
| 10,119,130 B2 * | 11/2018 | Schnorr | C12N 9/2462 |

FOREIGN PATENT DOCUMENTS

| | | |
|---|---|---|
| EP | 0425016 A2 | 5/1991 |
| GB | 2331750 A | 6/1999 |
| GB | 2379166 A | 3/2003 |
| JP | 2006-182662 A | 7/2006 |
| RU | 2232818 C1 | 7/2004 |
| WO | 00/21381 A1 | 4/2000 |
| WO | 02/33041 A2 | 4/2002 |
| WO | 02/064814 A2 | 8/2002 |
| WO | 03/005963 A2 | 1/2003 |
| WO | 2004/017988 A1 | 3/2004 |
| WO | 2004/026334 A1 | 4/2004 |
| WO | 2005/080559 A1 | 9/2005 |
| WO | 2008/124764 A1 | 10/2008 |
| WO | 2009/102755 A1 | 8/2009 |
| WO | 2010/115156 A2 | 10/2010 |
| WO | 2011/104339 A1 | 9/2011 |
| WO | 2013/076253 A1 | 5/2013 |

OTHER PUBLICATIONS

Maga et al. Transgenic Res. (2006)15:515-519.*
Oliver et al. Journal of Animal Science and Biotechnology (2015) 6:35.*
Felsch et al., Journal of Biological Chemistry, vol. 250, No. 10, pp. 3713-3720 (1975).
Fourgoux et al., Plant Molecular Biology, vol. 40, pp. 857-872 (1999).
Guo et al., PNAS, vol. 101, pp. 9205-9210 (2004).
Hughey et al., Applied and Environmental Mictobiology, vol. 53, No. 9, pp. 2165-2170 (1987).
Kimmenade et al., UniProt Accession No. AXQ25766 (2009).
Klosterman et al., UniProt Accession No. G2XHC2 (2011).
Korczynska et al., Acta Crystallographica Section F Strutural Biology and Crystallization Communications, vol. 60, No. 9, pp. 973-977 (2010).

(Continued)

*Primary Examiner* — Medina A Ibrahim

(74) *Attorney, Agent, or Firm* — Elias Lambiris

(57) ABSTRACT

The present invention relates to isolated polypeptides having lysozyme activity and polynucleotides encoding the polypeptides. The invention also relates to nucleic acid constructs, vectors, and host cells comprising the polynucleotides as well as methods of producing and using the polypeptides.

21 Claims, 34 Drawing Sheets

Specification includes a Sequence Listing.

(56) References Cited

OTHER PUBLICATIONS

Martinez et al., Nature Biotechnology, vol. 26, No. 5, pp. 553-560 (2008).
Martinez et al., UniProt Accession No. G0RAJ4 (2011).
Masschalck et al., Journal of Food Protection, vol. 65, No. 12, pp. 1916-1923 (2002).
Nierman et al., UniProt Accession No. B8M1A1 (2009).
Paces et al., Accession No. A26215 and J24831 (1986).
Seffernick et al., Journal of Bacteriology, vol. 183, No. 8, pp. 2405-2410 (2001).
Shimonishi et al, Geneseq Access No. AAX08639 (1999).
Wohlkonig et al., Plos One, vol. 5, No. 11, article 15388, pp. 1-10 (2010).

* cited by examiner

Figure 4

*Cl. perfringens* NN011260

Figure 5

*Cl. perfringens* clinical isolate

Figure 6A

```
ATOM      1  N   ARG A   1      44.522  50.717   8.838  1.00 28.67           N
ATOM      2  CA  ARG A   1      43.694  49.714   8.356  1.00 13.65           C
ATOM      3  C   ARG A   1      42.875  50.460   7.316  1.00 11.82           C
ATOM      4  O   ARG A   1      41.722  50.065   7.025  1.00 13.40           O
ATOM      5  CB  ARG A   1      42.689  49.227   9.407  1.00 14.16           C
ATOM      6  CG  ARG A   1      42.877  49.550  10.880  1.00 18.87           C
ATOM      7  CD  ARG A   1      44.201  49.369  11.187  1.00 20.58           C
ATOM      8  NE  ARG A   1      44.812  49.349  12.569  1.00 37.10           N
ATOM      9  CZ  ARG A   1      44.332  49.709  13.792  1.00 32.66           C
ATOM     10  NH1 ARG A   1      43.123  50.137  14.019  1.00 31.65           N
ATOM     11  NH2 ARG A   1      45.164  49.607  14.845  1.00 47.10           N
ATOM     12  N   ILE A   2      43.477  51.484   6.693  1.00  9.49           N
ATOM     13  CA  ILE A   2      42.829  52.301   5.732  1.00  8.53           C
ATOM     14  C   ILE A   2      43.510  52.136   4.370  1.00  7.94           C
ATOM     15  O   ILE A   2      44.735  52.324   4.281  1.00  8.51           O
ATOM     16  CB  ILE A   2      42.818  53.768   6.165  1.00  9.40           C
ATOM     17  CG1 ILE A   2      42.070  53.960   7.542  1.00 10.36           C
ATOM     18  CG2 ILE A   2      42.222  54.673   5.149  1.00  9.51           C
ATOM     19  CD1 ILE A   2      40.610  53.674   7.510  1.00 13.29           C
ATOM     20  N   PRO A   3      42.758  51.956   3.295  1.00  8.33           N
ATOM     21  CA  PRO A   3      43.374  51.836   1.953  1.00  8.50           C
ATOM     22  C   PRO A   3      43.590  53.176   1.294  1.00  7.67           C
ATOM     23  O   PRO A   3      42.848  54.166   1.486  1.00  9.16           O
ATOM     24  CB  PRO A   3      42.353  51.019   1.148  1.00  9.95           C
ATOM     25  CG  PRO A   3      41.022  51.355   1.829  1.00 10.42           C
ATOM     26  CD  PRO A   3      41.290  51.706   3.246  1.00  9.80           C
ATOM     27  N   GLY A   4      44.627  53.242   0.433  1.00  7.51           N
ATOM     28  CA  GLY A   4      44.913  54.373  -0.398  1.00  7.59           C
ATOM     29  C   GLY A   4      45.783  53.972  -1.586  1.00  7.28           C
ATOM     30  O   GLY A   4      45.956  52.778  -1.853  1.00  7.83           O
ATOM     31  N   PHE A   5      46.330  54.959  -2.269  1.00  7.08           N
ATOM     32  CA  PHE A   5      47.028  54.702  -3.507  1.00  7.40           C
ATOM     33  C   PHE A   5      48.018  55.802  -3.773  1.00  7.27           C
ATOM     34  O   PHE A   5      48.047  56.820  -3.049  1.00  7.99           O
ATOM     35  CB  PHE A   5      46.086  54.401  -4.647  1.00  7.75           C
ATOM     36  CG  PHE A   5      45.207  55.534  -5.143  1.00  8.67           C
ATOM     37  CD1 PHE A   5      44.137  55.975  -4.407  1.00  9.72           C
ATOM     38  CD2 PHE A   5      45.401  56.042  -6.402  1.00  9.19           C
ATOM     39  CE1 PHE A   5      43.305  57.031  -4.910  1.00 11.03           C
ATOM     40  CE2 PHE A   5      44.560  57.028  -6.925  1.00 10.44           C
ATOM     41  CZ  PHE A   5      43.538  57.527  -6.187  1.00 11.01           C
ATOM     42  N   ASP A   6      48.820  55.681  -4.824  1.00  6.90           N
ATOM     43  CA  ASP A   6      49.724  56.758  -5.243  1.00  6.79           C
ATOM     44  C   ASP A   6      49.826  56.760  -6.775  1.00  6.82           C
ATOM     45  O   ASP A   6      49.689  55.720  -7.408  1.00  7.49           O
ATOM     46  CB  ASP A   6      51.101  56.692  -4.538  1.00  7.91           C
ATOM     47  CG  ASP A   6      51.857  55.472  -4.847  1.00  9.00           C
ATOM     48  OD1 ASP A   6      52.552  55.425  -5.913  1.00  9.22           O
ATOM     49  OD2 ASP A   6      51.814  54.483  -4.007  1.00  8.80           O
ATOM     50  N   ILE A   7      50.062  57.947  -7.278  1.00  6.73           N
ATOM     51  CA  ILE A   7      50.053  58.210  -8.735  1.00  7.42           C
ATOM     52  C   ILE A   7      51.110  59.263  -9.051  1.00  8.07           C
```

Figure 6B

| ATOM | 53 | O | ILE | A | 7 | 51.579 | 60.035 | -8.239 | 1.00 | 7.60 | O |
| ATOM | 54 | CB | ILE | A | 7 | 48.654 | 58.697 | -9.233 | 1.00 | 8.10 | C |
| ATOM | 55 | CG1 | ILE | A | 7 | 48.225 | 60.003 | -8.485 | 1.00 | 8.33 | C |
| ATOM | 56 | CG2 | ILE | A | 7 | 47.643 | 57.575 | -9.068 | 1.00 | 8.98 | C |
| ATOM | 57 | CD1 | ILE | A | 7 | 46.836 | 60.482 | -8.839 | 1.00 | 9.54 | C |
| ATOM | 58 | N | SER | A | 8 | 51.481 | 59.225 | -10.348 | 1.00 | 8.89 | N |
| ATOM | 59 | CA | SER | A | 8 | 52.388 | 60.211 | -10.988 | 1.00 | 8.79 | C |
| ATOM | 60 | C | SER | A | 8 | 51.797 | 60.578 | -12.361 | 1.00 | 9.19 | C |
| ATOM | 61 | O | SER | A | 8 | 50.724 | 60.199 | -12.750 | 1.00 | 10.07 | O |
| ATOM | 62 | CB | SER | A | 8 | 53.787 | 59.651 | -11.138 | 1.00 | 10.12 | C |
| ATOM | 63 | OG | SER | A | 8 | 53.783 | 58.646 | -12.164 | 1.00 | 10.96 | O |
| ATOM | 64 | N | GLY | A | 9 | 52.606 | 61.339 | -13.106 | 1.00 | 10.94 | N |
| ATOM | 65 | CA | GLY | A | 9 | 52.279 | 61.698 | -14.467 | 1.00 | 12.92 | C |
| ATOM | 66 | C | GLY | A | 9 | 52.156 | 60.479 | -15.358 | 1.00 | 12.95 | C |
| ATOM | 67 | O | GLY | A | 9 | 51.550 | 60.572 | -16.518 | 1.00 | 13.87 | O |
| ATOM | 68 | N | TRP | A | 10 | 52.661 | 59.336 | -14.987 | 1.00 | 11.18 | N |
| ATOM | 69 | CA | TRP | A | 10 | 52.497 | 58.128 | -15.730 | 1.00 | 12.59 | C |
| ATOM | 70 | C | TRP | A | 10 | 51.047 | 57.589 | -15.762 | 1.00 | 12.34 | C |
| ATOM | 71 | O | TRP | A | 10 | 50.701 | 56.733 | -16.578 | 1.00 | 13.98 | O |
| ATOM | 72 | CB | TRP | A | 10 | 53.400 | 57.012 | -15.191 | 1.00 | 13.30 | C |
| ATOM | 73 | CG | TRP | A | 10 | 54.837 | 57.149 | -15.585 | 1.00 | 14.62 | C |
| ATOM | 74 | CD1 | TRP | A | 10 | 55.587 | 58.202 | -15.409 | 1.00 | 15.09 | C |
| ATOM | 75 | CD2 | TRP | A | 10 | 55.651 | 56.228 | -16.335 | 1.00 | 17.86 | C |
| ATOM | 76 | NE1 | TRP | A | 10 | 56.893 | 58.006 | -15.862 | 1.00 | 17.04 | N |
| ATOM | 77 | CE2 | TRP | A | 10 | 56.929 | 56.812 | -16.457 | 1.00 | 18.57 | C |
| ATOM | 78 | CE3 | TRP | A | 10 | 55.465 | 54.928 | -16.825 | 1.00 | 21.59 | C |
| ATOM | 79 | CZ2 | TRP | A | 10 | 58.003 | 56.182 | -17.131 | 1.00 | 21.31 | C |
| ATOM | 80 | CZ3 | TRP | A | 10 | 56.554 | 54.304 | -17.515 | 1.00 | 25.45 | C |
| ATOM | 81 | CH2 | TRP | A | 10 | 57.784 | 54.946 | -17.620 | 1.00 | 24.61 | C |
| ATOM | 82 | N | GLN | A | 11 | 50.183 | 58.108 | -14.889 | 1.00 | 11.59 | N |
| ATOM | 83 | CA | GLN | A | 11 | 48.729 | 57.778 | -14.843 | 1.00 | 11.19 | C |
| ATOM | 84 | C | GLN | A | 11 | 47.962 | 58.913 | -15.531 | 1.00 | 12.13 | C |
| ATOM | 85 | O | GLN | A | 11 | 47.742 | 59.940 | -14.942 | 1.00 | 13.60 | O |
| ATOM | 86 | CB | GLN | A | 11 | 48.272 | 57.611 | -13.408 | 1.00 | 11.93 | C |
| ATOM | 87 | CG | GLN | A | 11 | 48.604 | 56.274 | -12.810 | 1.00 | 11.53 | C |
| ATOM | 88 | CD | GLN | A | 11 | 50.090 | 56.067 | -12.586 | 1.00 | 11.82 | C |
| ATOM | 89 | OE1 | GLN | A | 11 | 50.719 | 56.753 | -11.777 | 1.00 | 11.76 | O |
| ATOM | 90 | NE2 | GLN | A | 11 | 50.678 | 55.110 | -13.245 | 1.00 | 12.98 | N |
| ATOM | 91 | N | PRO | A | 12 | 47.524 | 58.705 | -16.789 | 1.00 | 13.98 | N |
| ATOM | 92 | CA | PRO | A | 12 | 46.797 | 59.805 | -17.504 | 1.00 | 13.98 | C |
| ATOM | 93 | C | PRO | A | 12 | 45.446 | 60.165 | -16.907 | 1.00 | 13.81 | C |
| ATOM | 94 | O | PRO | A | 12 | 44.979 | 61.272 | -17.093 | 1.00 | 15.84 | O |
| ATOM | 95 | CB | PRO | A | 12 | 46.610 | 59.249 | -18.948 | 1.00 | 17.78 | C |
| ATOM | 96 | CG | PRO | A | 12 | 46.878 | 57.852 | -18.884 | 1.00 | 17.75 | C |
| ATOM | 97 | CD | PRO | A | 12 | 47.784 | 57.586 | -17.682 | 1.00 | 15.28 | C |
| ATOM | 98 | N | THR | A | 13 | 44.836 | 59.161 | -16.281 | 1.00 | 13.32 | N |
| ATOM | 99 | CA | THR | A | 13 | 43.458 | 59.221 | -15.873 | 1.00 | 12.96 | C |
| ATOM | 100 | C | THR | A | 13 | 43.266 | 58.706 | -14.449 | 1.00 | 12.59 | C |
| ATOM | 101 | O | THR | A | 13 | 43.712 | 57.628 | -14.111 | 1.00 | 12.26 | O |
| ATOM | 102 | CB | THR | A | 13 | 42.513 | 58.504 | -16.847 | 1.00 | 15.23 | C |
| ATOM | 103 | OG1 | THR | A | 13 | 42.898 | 57.159 | -16.970 | 1.00 | 16.83 | O |
| ATOM | 104 | CG2 | THR | A | 13 | 42.470 | 59.110 | -18.284 | 1.00 | 16.05 | C |
| ATOM | 105 | N | THR | A | 14 | 42.493 | 59.416 | -13.629 | 1.00 | 11.98 | N |

Figure 6C

| | | | | | | | | | | |
|---|---|---|---|---|---|---|---|---|---|---|
| ATOM | 106 | CA | THR | A | 14 | 42.064 | 59.004 | -12.294 | 1.00 | 10.95 | C |
| ATOM | 107 | C | THR | A | 14 | 40.651 | 59.576 | -12.025 | 1.00 | 10.45 | C |
| ATOM | 108 | O | THR | A | 14 | 40.546 | 60.807 | -12.041 | 1.00 | 13.30 | O |
| ATOM | 109 | CB | THR | A | 14 | 43.030 | 59.442 | -11.159 | 1.00 | 10.77 | C |
| ATOM | 110 | OG1 | THR | A | 14 | 44.371 | 59.027 | -11.465 | 1.00 | 11.59 | O |
| ATOM | 111 | CG2 | THR | A | 14 | 42.606 | 58.916 | -9.783 | 1.00 | 12.01 | C |
| ATOM | 112 | N | ASP | A | 15 | 39.676 | 58.734 | -11.773 | 1.00 | 11.44 | N |
| ATOM | 113 | CA | ASP | A | 15 | 38.292 | 59.184 | -11.365 | 1.00 | 11.52 | C |
| ATOM | 114 | C | ASP | A | 15 | 38.317 | 59.124 | -9.828 | 1.00 | 11.40 | C |
| ATOM | 115 | O | ASP | A | 15 | 38.133 | 58.039 | -9.252 | 1.00 | 11.41 | O |
| ATOM | 116 | CB | ASP | A | 15 | 37.286 | 58.227 | -12.051 | 1.00 | 12.88 | C |
| ATOM | 117 | CG | ASP | A | 15 | 35.841 | 58.541 | -11.736 | 1.00 | 14.20 | C |
| ATOM | 118 | OD1 | ASP | A | 15 | 35.610 | 59.256 | -10.714 | 1.00 | 14.70 | O |
| ATOM | 119 | OD2 | ASP | A | 15 | 34.928 | 57.951 | -12.453 | 1.00 | 15.80 | O |
| ATOM | 120 | N | PHE | A | 16 | 38.554 | 60.278 | -9.244 | 1.00 | 10.09 | N |
| ATOM | 121 | CA | PHE | A | 16 | 38.659 | 60.281 | -7.805 | 1.00 | 11.05 | C |
| ATOM | 122 | C | PHE | A | 16 | 37.341 | 59.995 | -7.077 | 1.00 | 11.59 | C |
| ATOM | 123 | O | PHE | A | 16 | 37.351 | 59.448 | -5.992 | 1.00 | 11.40 | O |
| ATOM | 124 | CB | PHE | A | 16 | 39.249 | 61.616 | -7.323 | 1.00 | 11.37 | C |
| ATOM | 125 | CG | PHE | A | 16 | 40.718 | 61.820 | -7.677 | 1.00 | 11.11 | C |
| ATOM | 126 | CD1 | PHE | A | 16 | 41.704 | 61.279 | -6.825 | 1.00 | 11.74 | C |
| ATOM | 127 | CD2 | PHE | A | 16 | 41.132 | 62.532 | -8.770 | 1.00 | 12.41 | C |
| ATOM | 128 | CE1 | PHE | A | 16 | 43.085 | 61.433 | -7.112 | 1.00 | 11.70 | C |
| ATOM | 129 | CE2 | PHE | A | 16 | 42.497 | 62.680 | -9.052 | 1.00 | 13.90 | C |
| ATOM | 130 | CZ | PHE | A | 16 | 43.449 | 62.084 | -8.220 | 1.00 | 13.42 | C |
| ATOM | 131 | N | ALA | A | 17 | 36.210 | 60.423 | -7.633 | 1.00 | 10.82 | N |
| ATOM | 132 | CA | ALA | A | 17 | 34.942 | 60.080 | -6.953 | 1.00 | 10.30 | C |
| ATOM | 133 | C | ALA | A | 17 | 34.762 | 58.591 | -6.902 | 1.00 | 10.11 | C |
| ATOM | 134 | O | ALA | A | 17 | 34.277 | 58.049 | -5.895 | 1.00 | 10.36 | O |
| ATOM | 135 | CB | ALA | A | 17 | 33.746 | 60.751 | -7.686 | 1.00 | 12.67 | C |
| ATOM | 136 | N | ARG | A | 18 | 35.133 | 57.873 | -8.012 | 1.00 | 10.18 | N |
| ATOM | 137 | CA | ARG | A | 18 | 34.994 | 56.406 | -8.040 | 1.00 | 10.65 | C |
| ATOM | 138 | C | ARG | A | 18 | 35.947 | 55.771 | -7.012 | 1.00 | 9.47 | C |
| ATOM | 139 | O | ARG | A | 18 | 35.591 | 54.787 | -6.340 | 1.00 | 10.53 | O |
| ATOM | 140 | CB | ARG | A | 18 | 35.152 | 55.848 | -9.463 | 1.00 | 11.68 | C |
| ATOM | 141 | CG | ARG | A | 18 | 34.998 | 54.353 | -9.601 | 1.00 | 14.84 | C |
| ATOM | 142 | CD | ARG | A | 18 | 34.934 | 54.019 | -11.213 | 1.00 | 23.23 | C |
| ATOM | 143 | NE | ARG | A | 18 | 36.181 | 53.424 | -11.776 | 1.00 | 30.81 | N |
| ATOM | 144 | CZ | ARG | A | 18 | 36.950 | 53.855 | -12.782 | 1.00 | 34.84 | C |
| ATOM | 145 | NH1 | ARG | A | 18 | 36.678 | 54.962 | -13.481 | 1.00 | 48.07 | N |
| ATOM | 146 | NH2 | ARG | A | 18 | 38.019 | 53.163 | -13.085 | 1.00 | 40.89 | N |
| ATOM | 147 | N | ALA | A | 19 | 37.163 | 56.298 | -6.954 | 1.00 | 10.43 | N |
| ATOM | 148 | CA | ALA | A | 19 | 38.146 | 55.747 | -5.988 | 1.00 | 10.49 | C |
| ATOM | 149 | C | ALA | A | 19 | 37.667 | 55.912 | -4.567 | 1.00 | 10.46 | C |
| ATOM | 150 | O | ALA | A | 19 | 37.767 | 54.993 | -3.725 | 1.00 | 10.61 | O |
| ATOM | 151 | CB | ALA | A | 19 | 39.479 | 56.469 | -6.136 | 1.00 | 10.90 | C |
| ATOM | 152 | N | TYR | A | 20 | 37.029 | 57.052 | -4.248 | 1.00 | 10.33 | N |
| ATOM | 153 | CA | TYR | A | 20 | 36.422 | 57.215 | -2.907 | 1.00 | 10.48 | C |
| ATOM | 154 | C | TYR | A | 20 | 35.265 | 56.297 | -2.700 | 1.00 | 11.22 | C |
| ATOM | 155 | O | TYR | A | 20 | 35.116 | 55.728 | -1.618 | 1.00 | 11.68 | O |
| ATOM | 156 | CB | TYR | A | 20 | 36.035 | 58.689 | -2.734 | 1.00 | 12.04 | C |
| ATOM | 157 | CG | TYR | A | 20 | 35.701 | 59.112 | -1.288 | 1.00 | 14.10 | C |
| ATOM | 158 | CD1 | TYR | A | 20 | 34.468 | 58.942 | -0.748 | 1.00 | 15.45 | C |

Figure 6D

| | | | | | | | | | | |
|---|---|---|---|---|---|---|---|---|---|---|
| ATOM | 159 | CD2 | TYR | A | 20 | 36.664 | 59.661 | -0.504 | 1.00 | 15.36 | C |
| ATOM | 160 | CE1 | TYR | A | 20 | 34.189 | 59.287 | 0.645 | 1.00 | 16.04 | C |
| ATOM | 161 | CE2 | TYR | A | 20 | 36.487 | 60.077 | 0.853 | 1.00 | 16.71 | C |
| ATOM | 162 | CZ | TYR | A | 20 | 35.219 | 59.853 | 1.365 | 1.00 | 17.27 | C |
| ATOM | 163 | OH | TYR | A | 20 | 34.988 | 60.278 | 2.723 | 1.00 | 23.85 | O |
| ATOM | 164 | N | ALA | A | 21 | 34.406 | 56.159 | -3.671 | 1.00 | 11.74 | N |
| ATOM | 165 | CA | ALA | A | 21 | 33.302 | 55.247 | -3.572 | 1.00 | 12.52 | C |
| ATOM | 166 | C | ALA | A | 21 | 33.737 | 53.820 | -3.344 | 1.00 | 12.22 | C |
| ATOM | 167 | O | ALA | A | 21 | 33.053 | 53.052 | -2.659 | 1.00 | 16.36 | O |
| ATOM | 168 | CB | ALA | A | 21 | 32.430 | 55.347 | -4.775 | 1.00 | 12.22 | C |
| ATOM | 169 | N | ASN | A | 22 | 34.904 | 53.431 | -3.886 | 1.00 | 11.82 | N |
| ATOM | 170 | CA | ASN | A | 22 | 35.522 | 52.133 | -3.713 | 1.00 | 12.76 | C |
| ATOM | 171 | C | ASN | A | 22 | 36.232 | 51.958 | -2.376 | 1.00 | 13.30 | C |
| ATOM | 172 | O | ASN | A | 22 | 36.641 | 50.854 | -2.066 | 1.00 | 15.52 | O |
| ATOM | 173 | CB | ASN | A | 22 | 36.466 | 51.834 | -4.865 | 1.00 | 14.61 | C |
| ATOM | 174 | CG | ASN | A | 22 | 35.705 | 51.618 | -6.187 | 1.00 | 16.35 | C |
| ATOM | 175 | OD1 | ASN | A | 22 | 34.490 | 51.353 | -6.250 | 1.00 | 20.40 | O |
| ATOM | 176 | ND2 | ASN | A | 22 | 36.414 | 51.861 | -7.277 | 1.00 | 17.12 | N |
| ATOM | 177 | N | GLY | A | 23 | 36.299 | 52.980 | -1.533 | 1.00 | 12.79 | N |
| ATOM | 178 | CA | GLY | A | 23 | 36.765 | 52.872 | -0.185 | 1.00 | 12.56 | C |
| ATOM | 179 | C | GLY | A | 23 | 38.124 | 53.522 | 0.057 | 1.00 | 11.65 | C |
| ATOM | 180 | O | GLY | A | 23 | 38.537 | 53.611 | 1.245 | 1.00 | 11.63 | O |
| ATOM | 181 | N | ASP | A | 24 | 38.819 | 54.020 | -0.954 | 1.00 | 10.49 | N |
| ATOM | 182 | CA | ASP | A | 24 | 40.145 | 54.643 | -0.719 | 1.00 | 9.49 | C |
| ATOM | 183 | C | ASP | A | 24 | 39.986 | 55.980 | -0.062 | 1.00 | 10.28 | C |
| ATOM | 184 | O | ASP | A | 24 | 39.021 | 56.714 | -0.358 | 1.00 | 10.02 | O |
| ATOM | 185 | CB | ASP | A | 24 | 40.852 | 54.758 | -2.046 | 1.00 | 10.59 | C |
| ATOM | 186 | CG | ASP | A | 24 | 41.112 | 53.399 | -2.627 | 1.00 | 13.93 | C |
| ATOM | 187 | OD1 | ASP | A | 24 | 41.547 | 52.437 | -1.896 | 1.00 | 18.04 | O |
| ATOM | 188 | OD2 | ASP | A | 24 | 40.712 | 53.071 | -3.756 | 1.00 | 16.80 | O |
| ATOM | 189 | N | ARG | A | 25 | 40.911 | 56.339 | 0.800 | 1.00 | 9.08 | N |
| ATOM | 190 | CA | ARG | A | 25 | 40.813 | 57.535 | 1.637 | 1.00 | 9.62 | C |
| ATOM | 191 | C | ARG | A | 25 | 41.960 | 58.453 | 1.565 | 1.00 | 9.30 | C |
| ATOM | 192 | O | ARG | A | 25 | 41.887 | 59.618 | 2.015 | 1.00 | 9.40 | O |
| ATOM | 193 | CB | ARG | A | 25 | 40.473 | 57.189 | 3.092 | 1.00 | 10.39 | C |
| ATOM | 194 | CG | ARG | A | 25 | 39.132 | 56.446 | 3.232 | 1.00 | 11.66 | C |
| ATOM | 195 | CD | ARG | A | 25 | 37.938 | 57.417 | 3.081 | 1.00 | 11.00 | C |
| ATOM | 196 | NE | ARG | A | 25 | 36.639 | 56.790 | 3.142 | 1.00 | 12.29 | N |
| ATOM | 197 | CZ | ARG | A | 25 | 35.958 | 56.372 | 2.101 | 1.00 | 14.10 | C |
| ATOM | 198 | NH1 | ARG | A | 25 | 36.436 | 56.341 | 0.845 | 1.00 | 12.17 | N |
| ATOM | 199 | NH2 | ARG | A | 25 | 34.709 | 55.929 | 2.338 | 1.00 | 16.43 | N |
| ATOM | 200 | N | PHE | A | 26 | 43.127 | 58.021 | 1.051 | 1.00 | 8.73 | N |
| ATOM | 201 | CA | PHE | A | 26 | 44.295 | 58.891 | 0.913 | 1.00 | 8.40 | C |
| ATOM | 202 | C | PHE | A | 26 | 44.974 | 58.552 | -0.404 | 1.00 | 7.37 | C |
| ATOM | 203 | O | PHE | A | 26 | 44.852 | 57.486 | -0.942 | 1.00 | 7.96 | O |
| ATOM | 204 | CB | PHE | A | 26 | 45.312 | 58.739 | 2.088 | 1.00 | 8.06 | C |
| ATOM | 205 | CG | PHE | A | 26 | 46.004 | 57.430 | 2.182 | 1.00 | 8.31 | C |
| ATOM | 206 | CD1 | PHE | A | 26 | 45.454 | 56.316 | 2.857 | 1.00 | 8.64 | C |
| ATOM | 207 | CD2 | PHE | A | 26 | 47.213 | 57.226 | 1.502 | 1.00 | 8.16 | C |
| ATOM | 208 | CE1 | PHE | A | 26 | 46.057 | 55.113 | 2.870 | 1.00 | 8.11 | C |
| ATOM | 209 | CE2 | PHE | A | 26 | 47.828 | 55.988 | 1.566 | 1.00 | 7.96 | C |
| ATOM | 210 | CZ | PHE | A | 26 | 47.259 | 54.952 | 2.208 | 1.00 | 8.94 | C |
| ATOM | 211 | N | VAL | A | 27 | 45.711 | 59.541 | -0.850 | 1.00 | 7.64 | N |

Figure 6E

| | | | | | | | | | | | |
|---|---|---|---|---|---|---|---|---|---|---|---|
| ATOM | 212 | CA  | VAL | A | 27 | 46.523 | 59.460 | -2.088 | 1.00 | 7.52  | C |
| ATOM | 213 | C   | VAL | A | 27 | 47.777 | 60.260 | -1.950 | 1.00 | 7.09  | C |
| ATOM | 214 | O   | VAL | A | 27 | 47.736 | 61.420 | -1.473 | 1.00 | 7.98  | O |
| ATOM | 215 | CB  | VAL | A | 27 | 45.672 | 59.836 | -3.363 | 1.00 | 8.09  | C |
| ATOM | 216 | CG1 | VAL | A | 27 | 45.209 | 61.270 | -3.329 | 1.00 | 9.41  | C |
| ATOM | 217 | CG2 | VAL | A | 27 | 46.439 | 59.558 | -4.636 | 1.00 | 8.80  | C |
| ATOM | 218 | N   | TYR | A | 28 | 48.912 | 59.673 | -2.384 | 1.00 | 6.71  | N |
| ATOM | 219 | CA  | TYR | A | 28 | 50.151 | 60.394 | -2.591 | 1.00 | 6.84  | C |
| ATOM | 220 | C   | TYR | A | 28 | 50.405 | 60.653 | -4.094 | 1.00 | 6.78  | C |
| ATOM | 221 | O   | TYR | A | 28 | 50.158 | 59.758 | -4.896 | 1.00 | 7.27  | O |
| ATOM | 222 | CB  | TYR | A | 28 | 51.346 | 59.630 | -1.977 | 1.00 | 6.78  | C |
| ATOM | 223 | CG  | TYR | A | 28 | 51.710 | 60.032 | -0.589 | 1.00 | 7.16  | C |
| ATOM | 224 | CD1 | TYR | A | 28 | 52.347 | 61.208 | -0.337 | 1.00 | 7.34  | C |
| ATOM | 225 | CD2 | TYR | A | 28 | 51.441 | 59.201 |  0.522 | 1.00 | 8.73  | C |
| ATOM | 226 | CE1 | TYR | A | 28 | 52.708 | 61.598 |  0.963 | 1.00 | 8.65  | C |
| ATOM | 227 | CE2 | TYR | A | 28 | 51.785 | 59.579 |  1.844 | 1.00 | 8.71  | C |
| ATOM | 228 | CZ  | TYR | A | 28 | 52.366 | 60.802 |  2.039 | 1.00 | 8.09  | C |
| ATOM | 229 | OH  | TYR | A | 28 | 52.719 | 61.123 |  3.352 | 1.00 | 8.81  | O |
| ATOM | 230 | N   | ILE | A | 29 | 50.843 | 61.880 | -4.393 | 1.00 | 6.84  | N |
| ATOM | 231 | CA  | ILE | A | 29 | 50.945 | 62.326 | -5.779 | 1.00 | 7.10  | C |
| ATOM | 232 | C   | ILE | A | 29 | 52.325 | 62.843 | -6.004 | 1.00 | 7.10  | C |
| ATOM | 233 | O   | ILE | A | 29 | 52.832 | 63.699 | -5.292 | 1.00 | 7.44  | O |
| ATOM | 234 | CB  | ILE | A | 29 | 49.869 | 63.466 | -5.998 | 1.00 | 8.00  | C |
| ATOM | 235 | CG1 | ILE | A | 29 | 48.478 | 62.905 | -5.783 | 1.00 | 9.18  | C |
| ATOM | 236 | CG2 | ILE | A | 29 | 50.010 | 63.992 | -7.409 | 1.00 | 9.33  | C |
| ATOM | 237 | CD1 | ILE | A | 29 | 47.377 | 63.959 | -5.554 | 1.00 | 10.36 | C |
| ATOM | 238 | N   | LYS | A | 30 | 52.965 | 62.384 | -7.106 | 1.00 | 7.18  | N |
| ATOM | 239 | CA  | LYS | A | 30 | 54.313 | 62.873 | -7.399 | 1.00 | 7.93  | C |
| ATOM | 240 | C   | LYS | A | 30 | 54.294 | 64.353 | -7.720 | 1.00 | 6.65  | C |
| ATOM | 241 | O   | LYS | A | 30 | 53.529 | 64.811 | -8.594 | 1.00 | 7.95  | O |
| ATOM | 242 | CB  | LYS | A | 30 | 54.933 | 62.102 | -8.573 | 1.00 | 8.53  | C |
| ATOM | 243 | CG  | LYS | A | 30 | 56.411 | 62.529 | -8.763 | 1.00 | 8.68  | C |
| ATOM | 244 | CD  | LYS | A | 30 | 57.124 | 61.691 | -9.829 | 1.00 | 10.14 | C |
| ATOM | 245 | CE  | LYS | A | 30 | 58.566 | 62.101 | -9.952 | 1.00 | 10.51 | C |
| ATOM | 246 | NZ  | LYS | A | 30 | 59.248 | 61.184 | -10.900 | 1.00 | 12.74 | N |
| ATOM | 247 | N   | ALA | A | 31 | 55.160 | 65.127 | -7.085 | 1.00 | 6.98  | N |
| ATOM | 248 | CA  | ALA | A | 31 | 55.316 | 66.568 | -7.357 | 1.00 | 6.99  | C |
| ATOM | 249 | C   | ALA | A | 31 | 56.630 | 66.827 | -8.135 | 1.00 | 7.25  | C |
| ATOM | 250 | O   | ALA | A | 31 | 56.592 | 67.558 | -9.167 | 1.00 | 7.98  | O |
| ATOM | 251 | CB  | ALA | A | 31 | 55.321 | 67.387 | -6.030 | 1.00 | 8.06  | C |
| ATOM | 252 | N   | THR | A | 32 | 57.741 | 66.364 | -7.654 | 1.00 | 7.88  | N |
| ATOM | 253 | CA  | THR | A | 32 | 59.065 | 66.755 | -8.127 | 1.00 | 7.82  | C |
| ATOM | 254 | C   | THR | A | 32 | 60.043 | 65.615 | -8.162 | 1.00 | 7.57  | C |
| ATOM | 255 | O   | THR | A | 32 | 59.849 | 64.549 | -7.503 | 1.00 | 7.69  | O |
| ATOM | 256 | CB  | THR | A | 32 | 59.646 | 67.885 | -7.237 | 1.00 | 8.16  | C |
| ATOM | 257 | OG1 | THR | A | 32 | 59.569 | 67.515 | -5.842 | 1.00 | 8.19  | O |
| ATOM | 258 | CG2 | THR | A | 32 | 58.914 | 69.212 | -7.370 | 1.00 | 8.81  | C |
| ATOM | 259 | N   | GLU | A | 33 | 61.155 | 65.868 | -8.861 | 1.00 | 8.03  | N |
| ATOM | 260 | CA  | GLU | A | 33 | 62.303 | 64.921 | -8.924 | 1.00 | 8.40  | C |
| ATOM | 261 | C   | GLU | A | 33 | 63.566 | 65.730 | -9.100 | 1.00 | 7.99  | C |
| ATOM | 262 | O   | GLU | A | 33 | 63.578 | 66.650 | -9.949 | 1.00 | 8.75  | O |
| ATOM | 263 | CB  | GLU | A | 33 | 62.096 | 63.857 | -9.962 | 1.00 | 8.41  | C |
| ATOM | 264 | CG  | GLU | A | 33 | 63.382 | 63.017 | -10.282 | 1.00 | 9.83 | C |

Figure 6F

```
ATOM    265  CD   GLU A  33      63.078  61.833 -11.199  1.00 11.04           C
ATOM    266  OE1  GLU A  33      61.935  61.561 -11.616  1.00 12.71           O
ATOM    267  OE2  GLU A  33      64.090  61.140 -11.563  1.00 12.87           O
ATOM    268  N    GLY A  34      64.620  65.462  -8.339  1.00  8.64           N
ATOM    269  CA   GLY A  34      65.806  66.261  -8.451  1.00  9.33           C
ATOM    270  C    GLY A  34      65.514  67.729  -8.235  1.00  9.27           C
ATOM    271  O    GLY A  34      64.733  68.054  -7.361  1.00  9.88           O
ATOM    272  N    THR A  35      66.166  68.617  -9.042  1.00 10.45           N
ATOM    273  CA   THR A  35      65.884  70.091  -8.985  1.00 11.61           C
ATOM    274  C    THR A  35      65.428  70.537 -10.344  1.00 10.50           C
ATOM    275  O    THR A  35      65.403  71.751 -10.571  1.00 12.74           O
ATOM    276  CB   THR A  35      67.050  70.910  -8.499  1.00 14.11           C
ATOM    277  OG1  THR A  35      68.088  70.721  -9.469  1.00 17.47           O
ATOM    278  CG2  THR A  35      67.504  70.495  -7.098  1.00 15.95           C
ATOM    279  N    THR A  36      65.031  69.659 -11.248  1.00 10.56           N
ATOM    280  CA   THR A  36      64.638  70.030 -12.610  1.00 10.84           C
ATOM    281  C    THR A  36      63.337  69.440 -13.069  1.00 10.02           C
ATOM    282  O    THR A  36      62.860  69.810 -14.164  1.00 11.69           O
ATOM    283  CB   THR A  36      65.734  69.544 -13.614  1.00 14.27           C
ATOM    284  OG1  THR A  36      65.972  68.132 -13.394  1.00 18.68           O
ATOM    285  CG2  THR A  36      67.007  70.208 -13.386  1.00 14.24           C
ATOM    286  N    PHE A  37      62.713  68.489 -12.388  1.00  8.31           N
ATOM    287  CA   PHE A  37      61.522  67.825 -12.834  1.00  8.29           C
ATOM    288  C    PHE A  37      60.305  68.305 -11.963  1.00  7.94           C
ATOM    289  O    PHE A  37      60.361  68.060 -10.688  1.00  8.28           O
ATOM    290  CB   PHE A  37      61.701  66.278 -12.686  1.00  8.53           C
ATOM    291  CG   PHE A  37      60.563  65.432 -13.132  1.00  8.21           C
ATOM    292  CD1  PHE A  37      59.421  65.297 -12.366  1.00  8.63           C
ATOM    293  CD2  PHE A  37      60.616  64.726 -14.319  1.00  9.40           C
ATOM    294  CE1  PHE A  37      58.396  64.491 -12.754  1.00 10.26           C
ATOM    295  CE2  PHE A  37      59.606  63.899 -14.740  1.00 10.70           C
ATOM    296  CZ   PHE A  37      58.456  63.790 -14.000  1.00 10.11           C
ATOM    297  N    LYS A  38      59.287  68.793 -12.602  1.00  8.29           N
ATOM    298  CA   LYS A  38      57.997  69.034 -11.968  1.00  8.93           C
ATOM    299  C    LYS A  38      56.992  68.183 -12.684  1.00  9.42           C
ATOM    300  O    LYS A  38      56.937  68.223 -13.970  1.00  9.23           O
ATOM    301  CB   LYS A  38      57.583  70.514 -12.032  1.00 10.78           C
ATOM    302  CG   LYS A  38      58.503  71.386 -11.282  1.00 12.80           C
ATOM    303  CD   LYS A  38      58.201  72.872 -11.390  1.00 15.66           C
ATOM    304  CE   LYS A  38      59.365  73.752 -10.958  1.00 17.50           C
ATOM    305  NZ   LYS A  38      58.902  75.226 -10.967  1.00 21.11           N
ATOM    306  N    SER A  39      56.149  67.405 -12.036  1.00  9.85           N
ATOM    307  CA   SER A  39      55.181  66.602 -12.705  1.00  9.58           C
ATOM    308  C    SER A  39      54.119  67.453 -13.368  1.00 11.30           C
ATOM    309  O    SER A  39      53.433  68.263 -12.736  1.00 11.78           O
ATOM    310  CB   SER A  39      54.456  65.665 -11.706  1.00 10.00           C
ATOM    311  OG   SER A  39      53.377  65.029 -12.406  1.00 10.74           O
ATOM    312  N   ASER A  40      53.962  67.232 -14.671  0.50 12.53           N
ATOM    313  CA  ASER A  40      52.919  67.883 -15.449  0.50 14.89           C
ATOM    314  C   ASER A  40      51.514  67.620 -14.930  0.50 14.99           C
ATOM    315  O   ASER A  40      50.632  68.492 -15.133  0.50 17.47           O
ATOM    316  CB  ASER A  40      53.036  67.513 -16.952  0.50 15.44           C
ATOM    317  OG  ASER A  40      54.361  67.827 -17.384  0.50 20.11           O
```

Figure 6G

| | | | | | | | | | | |
|---|---|---|---|---|---|---|---|---|---|---|
| ATOM | 318 | N | ALA | A | 41 | 51.280 | 66.476 | -14.289 | 1.00 12.70 | N |
| ATOM | 319 | CA | ALA | A | 41 | 49.982 | 66.046 | -13.829 | 1.00 12.26 | C |
| ATOM | 320 | C | ALA | A | 41 | 49.666 | 66.521 | -12.416 | 1.00 11.43 | C |
| ATOM | 321 | O | ALA | A | 41 | 48.529 | 66.371 | -11.953 | 1.00 12.05 | O |
| ATOM | 322 | CB | ALA | A | 41 | 49.872 | 64.528 | -13.888 | 1.00 13.05 | C |
| ATOM | 323 | N | PHE | A | 42 | 50.618 | 67.045 | -11.671 | 1.00 10.49 | N |
| ATOM | 324 | CA | PHE | A | 42 | 50.443 | 67.257 | -10.214 | 1.00 9.59 | C |
| ATOM | 325 | C | PHE | A | 42 | 49.239 | 68.120 | -9.941 | 1.00 11.41 | C |
| ATOM | 326 | O | PHE | A | 42 | 48.420 | 67.813 | -9.068 | 1.00 11.27 | O |
| ATOM | 327 | CB | PHE | A | 42 | 51.681 | 67.912 | -9.603 | 1.00 10.98 | C |
| ATOM | 328 | CG | PHE | A | 42 | 51.522 | 68.233 | -8.130 | 1.00 10.34 | C |
| ATOM | 329 | CD1 | PHE | A | 42 | 51.701 | 67.285 | -7.160 | 1.00 11.18 | C |
| ATOM | 330 | CD2 | PHE | A | 42 | 51.145 | 69.510 | -7.719 | 1.00 13.14 | C |
| ATOM | 331 | CE1 | PHE | A | 42 | 51.492 | 67.596 | -5.817 | 1.00 13.91 | C |
| ATOM | 332 | CE2 | PHE | A | 42 | 50.936 | 69.819 | -6.411 | 1.00 13.48 | C |
| ATOM | 333 | CZ | PHE | A | 42 | 51.092 | 68.874 | -5.494 | 1.00 13.70 | C |
| ATOM | 334 | N | SER | A | 43 | 49.127 | 69.256 | -10.633 | 1.00 13.53 | N |
| ATOM | 335 | CA | SER | A | 43 | 47.997 | 70.142 | -10.322 | 1.00 14.92 | C |
| ATOM | 336 | C | SER | A | 43 | 46.624 | 69.521 | -10.540 | 1.00 13.71 | C |
| ATOM | 337 | O | SER | A | 43 | 45.781 | 69.583 | -9.632 | 1.00 15.47 | O |
| ATOM | 338 | CB | SER | A | 43 | 48.103 | 71.449 | -11.166 | 1.00 19.52 | C |
| ATOM | 339 | OG | SER | A | 43 | 49.222 | 72.180 | -10.707 | 1.00 27.08 | O |
| ATOM | 340 | N | ARG | A | 44 | 46.420 | 68.872 | -11.641 | 1.00 14.34 | N |
| ATOM | 341 | CA | ARG | A | 44 | 45.188 | 68.224 | -11.908 | 1.00 14.39 | C |
| ATOM | 342 | C | ARG | A | 44 | 44.879 | 67.216 | -10.809 | 1.00 12.69 | C |
| ATOM | 343 | O | ARG | A | 44 | 43.722 | 67.019 | -10.369 | 1.00 13.11 | O |
| ATOM | 344 | CB | ARG | A | 44 | 45.201 | 67.548 | -13.309 | 1.00 17.32 | C |
| ATOM | 345 | CG | ARG | A | 44 | 43.963 | 66.837 | -13.715 | 1.00 26.99 | C |
| ATOM | 346 | CD | ARG | A | 44 | 44.270 | 66.143 | -15.064 | 1.00 28.55 | C |
| ATOM | 347 | NE | ARG | A | 44 | 45.125 | 64.951 | -14.966 | 1.00 28.03 | N |
| ATOM | 348 | CZ | ARG | A | 44 | 46.316 | 64.697 | -15.495 | 1.00 25.87 | C |
| ATOM | 349 | NH1 | ARG | A | 44 | 47.036 | 65.597 | -16.196 | 1.00 34.97 | N |
| ATOM | 350 | NH2 | ARG | A | 44 | 46.795 | 63.452 | -15.193 | 1.00 23.94 | N |
| ATOM | 351 | N | GLN | A | 45 | 45.907 | 66.412 | -10.474 | 1.00 11.98 | N |
| ATOM | 352 | CA | GLN | A | 45 | 45.676 | 65.276 | -9.541 | 1.00 10.58 | C |
| ATOM | 353 | C | GLN | A | 45 | 45.412 | 65.786 | -8.120 | 1.00 10.24 | C |
| ATOM | 354 | O | GLN | A | 45 | 44.532 | 65.282 | -7.451 | 1.00 10.44 | O |
| ATOM | 355 | CB | GLN | A | 45 | 46.968 | 64.421 | -9.615 | 1.00 10.20 | C |
| ATOM | 356 | CG | GLN | A | 45 | 47.025 | 63.669 | -10.921 | 1.00 10.26 | C |
| ATOM | 357 | CD | GLN | A | 45 | 48.355 | 62.882 | -11.125 | 1.00 10.50 | C |
| ATOM | 358 | OE1 | GLN | A | 45 | 49.374 | 63.303 | -10.607 | 1.00 11.51 | O |
| ATOM | 359 | NE2 | GLN | A | 45 | 48.336 | 61.804 | -11.881 | 1.00 11.82 | N |
| ATOM | 360 | N | TYR | A | 46 | 46.177 | 66.756 | -7.693 | 1.00 9.68 | N |
| ATOM | 361 | CA | TYR | A | 46 | 46.029 | 67.242 | -6.343 | 1.00 10.74 | C |
| ATOM | 362 | C | TYR | A | 46 | 44.729 | 67.984 | -6.153 | 1.00 13.00 | C |
| ATOM | 363 | O | TYR | A | 46 | 44.033 | 67.815 | -5.133 | 1.00 12.53 | O |
| ATOM | 364 | CB | TYR | A | 46 | 47.218 | 68.113 | -5.975 | 1.00 13.28 | C |
| ATOM | 365 | CG | TYR | A | 46 | 47.588 | 68.288 | -4.522 | 1.00 12.16 | C |
| ATOM | 366 | CD1 | TYR | A | 46 | 48.513 | 67.480 | -3.834 | 1.00 14.68 | C |
| ATOM | 367 | CD2 | TYR | A | 46 | 47.131 | 69.386 | -3.826 | 1.00 15.86 | C |
| ATOM | 368 | CE1 | TYR | A | 46 | 48.891 | 67.729 | -2.491 | 1.00 13.30 | C |
| ATOM | 369 | CE2 | TYR | A | 46 | 47.530 | 69.692 | -2.538 | 1.00 17.31 | C |
| ATOM | 370 | CZ | TYR | A | 46 | 48.434 | 68.888 | -1.881 | 1.00 14.36 | C |

Figure 6H

| ATOM | 371 | OH  | TYR | A | 46 | 48.872 | 69.220 | -0.585 | 1.00 | 16.96 | O |
|------|-----|-----|-----|---|----|--------|--------|--------|------|-------|---|
| ATOM | 372 | N   | THR | A | 47 | 44.294 | 68.671 | -7.222 | 1.00 | 13.41 | N |
| ATOM | 373 | CA  | THR | A | 47 | 42.979 | 69.342 | -7.107 | 1.00 | 14.05 | C |
| ATOM | 374 | C   | THR | A | 47 | 41.861 | 68.331 | -7.133 | 1.00 | 13.35 | C |
| ATOM | 375 | O   | THR | A | 47 | 40.874 | 68.438 | -6.361 | 1.00 | 13.78 | O |
| ATOM | 376 | CB  | THR | A | 47 | 42.809 | 70.361 | -8.274 | 1.00 | 16.18 | C |
| ATOM | 377 | OG1 | THR | A | 47 | 43.801 | 71.395 | -8.081 | 1.00 | 19.42 | O |
| ATOM | 378 | CG2 | THR | A | 47 | 41.382 | 70.993 | -8.245 | 1.00 | 17.40 | C |
| ATOM | 379 | N   | GLY | A | 48 | 41.938 | 67.307 | -7.992 | 1.00 | 13.17 | N |
| ATOM | 380 | CA  | GLY | A | 48 | 40.923 | 66.258 | -8.042 | 1.00 | 12.41 | C |
| ATOM | 381 | C   | GLY | A | 48 | 40.774 | 65.502 | -6.729 | 1.00 | 12.70 | C |
| ATOM | 382 | O   | GLY | A | 48 | 39.671 | 65.185 | -6.266 | 1.00 | 12.69 | O |
| ATOM | 383 | N   | ALA | A | 49 | 41.917 | 65.174 | -6.110 | 1.00 | 10.75 | N |
| ATOM | 384 | CA  | ALA | A | 49 | 41.896 | 64.561 | -4.815 | 1.00 | 10.58 | C |
| ATOM | 385 | C   | ALA | A | 49 | 41.183 | 65.451 | -3.793 | 1.00 | 10.40 | C |
| ATOM | 386 | O   | ALA | A | 49 | 40.333 | 65.007 | -3.033 | 1.00 | 11.39 | O |
| ATOM | 387 | CB  | ALA | A | 49 | 43.319 | 64.230 | -4.352 | 1.00 | 10.62 | C |
| ATOM | 388 | N   | THR | A | 50 | 41.562 | 66.728 | -3.803 | 1.00 | 11.17 | N |
| ATOM | 389 | CA  | THR | A | 50 | 41.002 | 67.675 | -2.807 | 1.00 | 11.82 | C |
| ATOM | 390 | C   | THR | A | 50 | 39.476 | 67.809 | -2.948 | 1.00 | 11.99 | C |
| ATOM | 391 | O   | THR | A | 50 | 38.783 | 67.725 | -1.934 | 1.00 | 12.56 | O |
| ATOM | 392 | CB  | THR | A | 50 | 41.651 | 69.042 | -3.024 | 1.00 | 12.51 | C |
| ATOM | 393 | OG1 | THR | A | 50 | 43.055 | 68.971 | -2.897 | 1.00 | 12.48 | O |
| ATOM | 394 | CG2 | THR | A | 50 | 41.140 | 70.091 | -2.003 | 1.00 | 13.54 | C |
| ATOM | 395 | N   | GLN | A | 51 | 38.981 | 67.889 | -4.170 | 1.00 | 11.41 | N |
| ATOM | 396 | CA  | GLN | A | 51 | 37.578 | 68.138 | -4.451 | 1.00 | 12.92 | C |
| ATOM | 397 | C   | GLN | A | 51 | 36.759 | 66.932 | -4.273 | 1.00 | 13.68 | C |
| ATOM | 398 | O   | GLN | A | 51 | 35.521 | 67.063 | -4.280 | 1.00 | 16.91 | O |
| ATOM | 399 | CB  | GLN | A | 51 | 37.460 | 68.681 | -5.875 | 1.00 | 14.43 | C |
| ATOM | 400 | CG  | GLN | A | 51 | 37.952 | 70.110 | -6.048 | 1.00 | 15.58 | C |
| ATOM | 401 | CD  | GLN | A | 51 | 38.029 | 70.579 | -7.542 | 1.00 | 17.76 | C |
| ATOM | 402 | OE1 | GLN | A | 51 | 37.966 | 69.736 | -8.486 | 1.00 | 20.81 | O |
| ATOM | 403 | NE2 | GLN | A | 51 | 38.159 | 71.876 | -7.775 | 1.00 | 16.97 | N |
| ATOM | 404 | N   | ASN | A | 52 | 37.327 | 65.705 | -4.102 | 1.00 | 13.02 | N |
| ATOM | 405 | CA  | ASN | A | 52 | 36.614 | 64.491 | -3.958 | 1.00 | 12.89 | C |
| ATOM | 406 | C   | ASN | A | 52 | 36.798 | 63.806 | -2.579 | 1.00 | 12.65 | C |
| ATOM | 407 | O   | ASN | A | 52 | 36.557 | 62.658 | -2.416 | 1.00 | 14.41 | O |
| ATOM | 408 | CB  | ASN | A | 52 | 36.873 | 63.546 | -5.140 | 1.00 | 13.03 | C |
| ATOM | 409 | CG  | ASN | A | 52 | 36.279 | 64.053 | -6.392 | 1.00 | 13.74 | C |
| ATOM | 410 | OD1 | ASN | A | 52 | 35.033 | 63.896 | -6.528 | 1.00 | 15.81 | O |
| ATOM | 411 | ND2 | ASN | A | 52 | 37.048 | 64.728 | -7.209 | 1.00 | 13.49 | N |
| ATOM | 412 | N   | GLY | A | 53 | 37.217 | 64.572 | -1.608 | 1.00 | 12.97 | N |
| ATOM | 413 | CA  | GLY | A | 53 | 37.214 | 64.181 | -0.208 | 1.00 | 14.24 | C |
| ATOM | 414 | C   | GLY | A | 53 | 38.449 | 63.450 |  0.319 | 1.00 | 12.69 | C |
| ATOM | 415 | O   | GLY | A | 53 | 38.432 | 62.875 |  1.418 | 1.00 | 13.69 | O |
| ATOM | 416 | N   | PHE | A | 54 | 39.530 | 63.411 | -0.477 | 1.00 | 11.36 | N |
| ATOM | 417 | CA  | PHE | A | 54 | 40.763 | 62.714 | -0.049 | 1.00 | 10.23 | C |
| ATOM | 418 | C   | PHE | A | 54 | 41.595 | 63.478 |  0.904 | 1.00 | 10.21 | C |
| ATOM | 419 | O   | PHE | A | 54 | 41.666 | 64.722 |  0.845 | 1.00 | 11.35 | O |
| ATOM | 420 | CB  | PHE | A | 54 | 41.597 | 62.343 | -1.300 | 1.00 | 10.42 | C |
| ATOM | 421 | CG  | PHE | A | 54 | 41.154 | 61.146 | -2.004 | 1.00 |  9.27 | C |
| ATOM | 422 | CD1 | PHE | A | 54 | 40.114 | 61.141 | -2.980 | 1.00 | 10.98 | C |
| ATOM | 423 | CD2 | PHE | A | 54 | 41.689 | 59.918 | -1.658 | 1.00 |  9.96 | C |

Figure 6I

```
ATOM    424  CE1 PHE A  54      39.670  59.988  -3.515  1.00 11.65           C
ATOM    425  CE2 PHE A  54      41.273  58.774  -2.198  1.00 10.85           C
ATOM    426  CZ  PHE A  54      40.214  58.768  -3.095  1.00 11.71           C
ATOM    427  N   ILE A  55      42.268  62.750   1.811  1.00 10.66           N
ATOM    428  CA  ILE A  55      43.455  63.198   2.456  1.00  9.81           C
ATOM    429  C   ILE A  55      44.617  62.960   1.428  1.00  9.43           C
ATOM    430  O   ILE A  55      44.603  61.884   0.778  1.00 10.35           O
ATOM    431  CB  ILE A  55      43.690  62.478   3.775  1.00 10.15           C
ATOM    432  CG1 ILE A  55      42.563  62.795   4.768  1.00 10.78           C
ATOM    433  CG2 ILE A  55      45.068  62.662   4.339  1.00 10.81           C
ATOM    434  CD1 ILE A  55      42.526  61.905   6.001  1.00 13.46           C
ATOM    435  N   ARG A  56      45.465  63.910   1.221  1.00  8.57           N
ATOM    436  CA  ARG A  56      46.534  63.782   0.176  1.00  8.89           C
ATOM    437  C   ARG A  56      47.782  64.321   0.606  1.00  8.31           C
ATOM    438  O   ARG A  56      47.876  65.214   1.463  1.00  9.60           O
ATOM    439  CB  ARG A  56      46.003  64.366  -1.180  1.00  9.99           C
ATOM    440  CG  ARG A  56      45.898  65.862  -1.164  1.00 10.71           C
ATOM    441  CD  ARG A  56      44.544  66.392  -0.619  1.00 11.99           C
ATOM    442  NE  ARG A  56      44.419  67.858  -0.810  1.00 12.28           N
ATOM    443  CZ  ARG A  56      44.984  68.769  -0.089  1.00 12.95           C
ATOM    444  NH1 ARG A  56      45.689  68.469   1.015  1.00 15.22           N
ATOM    445  NH2 ARG A  56      44.859  70.065  -0.454  1.00 15.44           N
ATOM    446  N   GLY A  57      48.839  63.809  -0.015  1.00  8.65           N
ATOM    447  CA  GLY A  57      50.142  64.312   0.122  1.00  8.60           C
ATOM    448  C   GLY A  57      50.926  64.282  -1.202  1.00  7.17           C
ATOM    449  O   GLY A  57      50.463  63.681  -2.175  1.00  8.31           O
ATOM    450  N   ALA A  58      52.077  64.871  -1.231  1.00  7.08           N
ATOM    451  CA  ALA A  58      52.975  64.892  -2.381  1.00  7.20           C
ATOM    452  C   ALA A  58      54.197  64.068  -2.082  1.00  6.30           C
ATOM    453  O   ALA A  58      54.594  63.918  -0.903  1.00  7.74           O
ATOM    454  CB  ALA A  58      53.341  66.359  -2.665  1.00  7.44           C
ATOM    455  N   TYR A  59      54.920  63.670  -3.121  1.00  7.40           N
ATOM    456  CA  TYR A  59      56.224  63.016  -2.954  1.00  7.03           C
ATOM    457  C   TYR A  59      57.260  63.549  -3.940  1.00  6.98           C
ATOM    458  O   TYR A  59      56.939  64.110  -5.032  1.00  7.63           O
ATOM    459  CB  TYR A  59      56.116  61.480  -2.956  1.00  6.99           C
ATOM    460  CG  TYR A  59      55.866  60.785  -4.257  1.00  7.40           C
ATOM    461  CD1 TYR A  59      56.927  60.434  -5.097  1.00  8.03           C
ATOM    462  CD2 TYR A  59      54.600  60.367  -4.642  1.00  8.44           C
ATOM    463  CE1 TYR A  59      56.703  59.715  -6.242  1.00  9.40           C
ATOM    464  CE2 TYR A  59      54.368  59.643  -5.832  1.00  8.72           C
ATOM    465  CZ  TYR A  59      55.436  59.293  -6.599  1.00  9.24           C
ATOM    466  OH  TYR A  59      55.278  58.555  -7.768  1.00 10.37           O
ATOM    467  N   HIS A  60      58.492  63.403  -3.523  1.00  7.37           N
ATOM    468  CA  HIS A  60      59.683  63.847  -4.241  1.00  7.12           C
ATOM    469  C   HIS A  60      60.552  62.654  -4.561  1.00  7.27           C
ATOM    470  O   HIS A  60      60.915  61.897  -3.631  1.00  7.70           O
ATOM    471  CB  HIS A  60      60.496  64.780  -3.304  1.00  7.33           C
ATOM    472  CG  HIS A  60      61.765  65.224  -3.987  1.00  7.71           C
ATOM    473  ND1 HIS A  60      63.031  64.786  -3.800  1.00  9.42           N
ATOM    474  CD2 HIS A  60      61.807  66.224  -4.949  1.00  5.89           C
ATOM    475  CE1 HIS A  60      63.852  65.474  -4.644  1.00  6.33           C
ATOM    476  NE2 HIS A  60      63.075  66.329  -5.333  1.00  9.96           N
```

Figure 6J

| ATOM | 477 | N | PHE | A | 61 | 60.941 | 62.471 | -5.838 | 1.00 | 7.07 | N |
|------|-----|-----|------|---|-----|--------|--------|--------|------|-------|---|
| ATOM | 478 | CA | PHE | A | 61 | 61.919 | 61.380 | -6.196 | 1.00 | 7.73 | C |
| ATOM | 479 | C | PHE | A | 61 | 63.313 | 61.917 | -5.990 | 1.00 | 8.06 | C |
| ATOM | 480 | O | PHE | A | 61 | 63.806 | 62.840 | -6.730 | 1.00 | 8.29 | O |
| ATOM | 481 | CB | PHE | A | 61 | 61.653 | 60.892 | -7.605 | 1.00 | 8.46 | C |
| ATOM | 482 | CG | PHE | A | 61 | 62.409 | 59.595 | -7.885 | 1.00 | 9.48 | C |
| ATOM | 483 | CD1 | PHE | A | 61 | 63.697 | 59.600 | -8.288 | 1.00 | 9.86 | C |
| ATOM | 484 | CD2 | PHE | A | 61 | 61.808 | 58.377 | -7.727 | 1.00 | 11.77 | C |
| ATOM | 485 | CE1 | PHE | A | 61 | 64.427 | 58.372 | -8.499 | 1.00 | 11.94 | C |
| ATOM | 486 | CE2 | PHE | A | 61 | 62.502 | 57.172 | -7.957 | 1.00 | 14.50 | C |
| ATOM | 487 | CZ | PHE | A | 61 | 63.793 | 57.190 | -8.354 | 1.00 | 13.51 | C |
| ATOM | 488 | N | ALA | A | 62 | 64.031 | 61.405 | -5.027 | 1.00 | 7.50 | N |
| ATOM | 489 | CA | ALA | A | 62 | 65.368 | 61.827 | -4.701 | 1.00 | 7.69 | C |
| ATOM | 490 | C | ALA | A | 62 | 66.375 | 61.550 | -5.821 | 1.00 | 7.43 | C |
| ATOM | 491 | O | ALA | A | 62 | 66.386 | 60.441 | -6.406 | 1.00 | 8.44 | O |
| ATOM | 492 | CB | ALA | A | 62 | 65.860 | 61.137 | -3.434 | 1.00 | 8.22 | C |
| ATOM | 493 | N | GLN | A | 63 | 67.273 | 62.489 | -6.048 | 1.00 | 7.84 | N |
| ATOM | 494 | CA | GLN | A | 63 | 68.416 | 62.316 | -6.955 | 1.00 | 8.62 | C |
| ATOM | 495 | C | GLN | A | 63 | 69.675 | 62.734 | -6.225 | 1.00 | 8.31 | C |
| ATOM | 496 | O | GLN | A | 63 | 70.136 | 63.896 | -6.332 | 1.00 | 9.41 | O |
| ATOM | 497 | CB | GLN | A | 63 | 68.203 | 63.093 | -8.255 | 1.00 | 8.63 | C |
| ATOM | 498 | CG | GLN | A | 63 | 67.154 | 62.493 | -9.170 | 1.00 | 9.33 | C |
| ATOM | 499 | CD | GLN | A | 63 | 67.639 | 61.242 | -9.873 | 1.00 | 10.45 | C |
| ATOM | 500 | OE1 | GLN | A | 63 | 68.806 | 60.810 | -9.717 | 1.00 | 11.19 | O |
| ATOM | 501 | NE2 | GLN | A | 63 | 66.771 | 60.645 | -10.638 | 1.00 | 10.88 | N |
| ATOM | 502 | N | PRO | A | 64 | 70.231 | 61.866 | -5.327 | 1.00 | 8.85 | N |
| ATOM | 503 | CA | PRO | A | 64 | 71.231 | 62.330 | -4.420 | 1.00 | 9.41 | C |
| ATOM | 504 | C | PRO | A | 64 | 72.537 | 62.793 | -5.002 | 1.00 | 10.50 | C |
| ATOM | 505 | O | PRO | A | 64 | 73.287 | 63.475 | -4.306 | 1.00 | 12.39 | O |
| ATOM | 506 | CB | PRO | A | 64 | 71.455 | 61.132 | -3.482 | 1.00 | 9.98 | C |
| ATOM | 507 | CG | PRO | A | 64 | 70.084 | 60.427 | -3.471 | 1.00 | 10.74 | C |
| ATOM | 508 | CD | PRO | A | 64 | 69.707 | 60.540 | -4.924 | 1.00 | 8.09 | C |
| ATOM | 509 | N | ALA | A | 65 | 72.847 | 62.402 | -6.219 | 1.00 | 10.10 | N |
| ATOM | 510 | CA | ALA | A | 65 | 74.089 | 62.879 | -6.860 | 1.00 | 12.06 | C |
| ATOM | 511 | C | ALA | A | 65 | 73.875 | 64.199 | -7.558 | 1.00 | 12.89 | C |
| ATOM | 512 | O | ALA | A | 65 | 74.882 | 64.803 | -7.956 | 1.00 | 14.94 | O |
| ATOM | 513 | CB | ALA | A | 65 | 74.605 | 61.838 | -7.843 | 1.00 | 12.78 | C |
| ATOM | 514 | N | ALA | A | 66 | 72.676 | 64.694 | -7.721 | 1.00 | 12.07 | N |
| ATOM | 515 | CA | ALA | A | 66 | 72.405 | 65.878 | -8.562 | 1.00 | 13.09 | C |
| ATOM | 516 | C | ALA | A | 66 | 72.550 | 67.168 | -7.837 | 1.00 | 12.42 | C |
| ATOM | 517 | O | ALA | A | 66 | 72.813 | 68.242 | -8.477 | 1.00 | 16.34 | O |
| ATOM | 518 | CB | ALA | A | 66 | 71.040 | 65.752 | -9.214 | 1.00 | 13.65 | C |
| ATOM | 519 | N | ASER | A | 67 | 72.330 | 67.190 | -6.523 | 0.50 | 11.82 | N |
| ATOM | 520 | CA | ASER | A | 67 | 72.331 | 68.432 | -5.685 | 0.50 | 12.07 | C |
| ATOM | 521 | C | ASER | A | 67 | 72.345 | 68.041 | -4.250 | 0.50 | 12.63 | C |
| ATOM | 522 | O | ASER | A | 67 | 72.215 | 66.848 | -3.953 | 0.50 | 13.69 | O |
| ATOM | 523 | CB | ASER | A | 67 | 71.077 | 69.297 | -5.864 | 0.50 | 12.18 | C |
| ATOM | 524 | OG | ASER | A | 67 | 69.993 | 68.703 | -5.109 | 0.50 | 10.79 | O |
| ATOM | 525 | N | SER | A | 68 | 72.365 | 68.995 | -3.367 | 1.00 | 12.46 | N |
| ATOM | 526 | CA | SER | A | 68 | 72.256 | 68.701 | -1.943 | 1.00 | 12.29 | C |
| ATOM | 527 | C | SER | A | 68 | 70.806 | 68.252 | -1.604 | 1.00 | 10.64 | C |
| ATOM | 528 | O | SER | A | 68 | 69.893 | 68.537 | -2.242 | 1.00 | 10.44 | O |
| ATOM | 529 | CB | SER | A | 68 | 72.637 | 69.937 | -1.126 | 1.00 | 12.11 | C |

Figure 6K

| ATOM | 530 | OG | SER | A | 68 | 71.660 | 70.955 | -1.274 | 1.00 | 12.58 | O |
|------|-----|----|-----|---|----|--------|--------|--------|------|-------|---|
| ATOM | 531 | N | GLY | A | 69 | 70.718 | 67.665 | -0.426 | 1.00 | 10.53 | N |
| ATOM | 532 | CA | GLY | A | 69 | 69.422 | 67.280 | 0.159 | 1.00 | 10.03 | C |
| ATOM | 533 | C | GLY | A | 69 | 68.597 | 68.530 | 0.430 | 1.00 | 9.69 | C |
| ATOM | 534 | O | GLY | A | 69 | 67.391 | 68.575 | 0.228 | 1.00 | 9.99 | O |
| ATOM | 535 | N | ALA | A | 70 | 69.278 | 69.583 | 0.950 | 1.00 | 10.62 | N |
| ATOM | 536 | CA | ALA | A | 70 | 68.593 | 70.834 | 1.246 | 1.00 | 10.71 | C |
| ATOM | 537 | C | ALA | A | 70 | 67.978 | 71.458 | 0.005 | 1.00 | 9.81 | C |
| ATOM | 538 | O | ALA | A | 70 | 66.871 | 71.945 | 0.005 | 1.00 | 10.60 | O |
| ATOM | 539 | CB | ALA | A | 70 | 69.532 | 71.841 | 1.903 | 1.00 | 11.75 | C |
| ATOM | 540 | N | ALA | A | 71 | 68.752 | 71.464 | -1.107 | 1.00 | 11.21 | N |
| ATOM | 541 | CA | ALA | A | 71 | 68.252 | 72.058 | -2.377 | 1.00 | 9.99 | C |
| ATOM | 542 | C | ALA | A | 71 | 66.961 | 71.342 | -2.826 | 1.00 | 9.58 | C |
| ATOM | 543 | O | ALA | A | 71 | 66.033 | 71.923 | -3.336 | 1.00 | 9.64 | O |
| ATOM | 544 | CB | ALA | A | 71 | 69.344 | 71.975 | -3.445 | 1.00 | 11.87 | C |
| ATOM | 545 | N | GLN | A | 72 | 66.959 | 69.984 | -2.702 | 1.00 | 8.82 | N |
| ATOM | 546 | CA | GLN | A | 72 | 65.807 | 69.221 | -3.134 | 1.00 | 7.95 | C |
| ATOM | 547 | C | GLN | A | 72 | 64.612 | 69.414 | -2.198 | 1.00 | 8.37 | C |
| ATOM | 548 | O | GLN | A | 72 | 63.495 | 69.416 | -2.647 | 1.00 | 8.69 | O |
| ATOM | 549 | CB | GLN | A | 72 | 66.215 | 67.762 | -3.360 | 1.00 | 8.44 | C |
| ATOM | 550 | CG | GLN | A | 72 | 66.941 | 67.634 | -4.725 | 1.00 | 8.49 | C |
| ATOM | 551 | CD | GLN | A | 72 | 67.419 | 66.267 | -5.096 | 1.00 | 8.50 | C |
| ATOM | 552 | OE1 | GLN | A | 72 | 66.699 | 65.238 | -5.012 | 1.00 | 8.67 | O |
| ATOM | 553 | NE2 | GLN | A | 72 | 68.639 | 66.212 | -5.600 | 1.00 | 8.56 | N |
| ATOM | 554 | N | ALA | A | 73 | 64.873 | 69.514 | -0.899 | 1.00 | 8.14 | N |
| ATOM | 555 | CA | ALA | A | 73 | 63.762 | 69.801 | 0.048 | 1.00 | 8.54 | C |
| ATOM | 556 | C | ALA | A | 73 | 63.072 | 71.122 | -0.307 | 1.00 | 9.19 | C |
| ATOM | 557 | O | ALA | A | 73 | 61.864 | 71.249 | -0.280 | 1.00 | 9.52 | O |
| ATOM | 558 | CB | ALA | A | 73 | 64.227 | 69.753 | 1.483 | 1.00 | 9.22 | C |
| ATOM | 559 | N | AARG | A | 74 | 63.946 | 72.136 | -0.555 | 0.25 | 9.52 | N |
| ATOM | 560 | CA | AARG | A | 74 | 63.524 | 73.494 | -0.944 | 0.25 | 10.04 | C |
| ATOM | 561 | C | AARG | A | 74 | 62.648 | 73.411 | -2.252 | 0.25 | 9.46 | C |
| ATOM | 562 | O | AARG | A | 74 | 61.561 | 73.976 | -2.326 | 0.25 | 10.40 | O |
| ATOM | 563 | CB | AARG | A | 74 | 64.741 | 74.503 | -1.104 | 0.25 | 10.43 | C |
| ATOM | 564 | CG | AARG | A | 74 | 65.611 | 74.930 | 0.119 | 0.25 | 10.76 | C |
| ATOM | 565 | CD | AARG | A | 74 | 66.880 | 75.785 | -0.324 | 0.25 | 10.41 | C |
| ATOM | 566 | NE | AARG | A | 74 | 67.968 | 75.710 | 0.602 | 0.25 | 10.51 | N |
| ATOM | 567 | CZ | AARG | A | 74 | 69.232 | 75.390 | 0.351 | 0.25 | 12.61 | C |
| ATOM | 568 | NH1 | AARG | A | 74 | 69.668 | 75.022 | -0.830 | 0.25 | 13.39 | N |
| ATOM | 569 | NH2 | AARG | A | 74 | 70.076 | 75.494 | 1.324 | 0.25 | 14.84 | N |
| ATOM | 570 | N | TYR | A | 75 | 63.109 | 72.693 | -3.284 | 1.00 | 9.11 | N |
| ATOM | 571 | CA | TYR | A | 75 | 62.435 | 72.577 | -4.550 | 1.00 | 9.25 | C |
| ATOM | 572 | C | TYR | A | 75 | 61.096 | 71.861 | -4.422 | 1.00 | 9.01 | C |
| ATOM | 573 | O | TYR | A | 75 | 60.084 | 72.266 | -4.991 | 1.00 | 9.17 | O |
| ATOM | 574 | CB | TYR | A | 75 | 63.344 | 71.842 | -5.559 | 1.00 | 10.49 | C |
| ATOM | 575 | CG | TYR | A | 75 | 62.884 | 71.775 | -6.986 | 1.00 | 10.09 | C |
| ATOM | 576 | CD1 | TYR | A | 75 | 62.961 | 72.916 | -7.838 | 1.00 | 12.15 | C |
| ATOM | 577 | CD2 | TYR | A | 75 | 62.446 | 70.571 | -7.583 | 1.00 | 10.31 | C |
| ATOM | 578 | CE1 | TYR | A | 75 | 62.594 | 72.834 | -9.170 | 1.00 | 11.74 | C |
| ATOM | 579 | CE2 | TYR | A | 75 | 62.099 | 70.496 | -8.900 | 1.00 | 11.50 | C |
| ATOM | 580 | CZ | TYR | A | 75 | 62.207 | 71.633 | -9.701 | 1.00 | 10.99 | C |
| ATOM | 581 | OH | TYR | A | 75 | 61.881 | 71.455 | -11.025 | 1.00 | 13.76 | O |
| ATOM | 582 | N | PHE | A | 76 | 61.094 | 70.746 | -3.671 | 1.00 | 9.00 | N |

Figure 6L

| ATOM | 583 | CA | PHE | A | 76 | 59.869 | 70.019 | -3.403 | 1.00 | 8.68 | C |
|------|-----|-----|-----|---|----|--------|--------|--------|------|------|---|
| ATOM | 584 | C | PHE | A | 76 | 58.807 | 70.920 | -2.679 | 1.00 | 8.88 | C |
| ATOM | 585 | O | PHE | A | 76 | 57.688 | 70.967 | -3.070 | 1.00 | 9.01 | O |
| ATOM | 586 | CB | PHE | A | 76 | 60.233 | 68.785 | -2.558 | 1.00 | 9.06 | C |
| ATOM | 587 | CG | PHE | A | 76 | 59.069 | 67.938 | -2.067 | 1.00 | 7.94 | C |
| ATOM | 588 | CD1 | PHE | A | 76 | 58.095 | 67.489 | -2.907 | 1.00 | 8.10 | C |
| ATOM | 589 | CD2 | PHE | A | 76 | 59.045 | 67.597 | -0.748 | 1.00 | 9.01 | C |
| ATOM | 590 | CE1 | PHE | A | 76 | 57.101 | 66.664 | -2.442 | 1.00 | 7.55 | C |
| ATOM | 591 | CE2 | PHE | A | 76 | 58.051 | 66.728 | -0.235 | 1.00 | 8.28 | C |
| ATOM | 592 | CZ | PHE | A | 76 | 57.072 | 66.271 | -1.079 | 1.00 | 8.68 | C |
| ATOM | 593 | N | ALA | A | 77 | 59.273 | 71.512 | -1.576 | 1.00 | 8.86 | N |
| ATOM | 594 | CA | ALA | A | 77 | 58.339 | 72.280 | -0.748 | 1.00 | 10.42 | C |
| ATOM | 595 | C | ALA | A | 77 | 57.760 | 73.481 | -1.521 | 1.00 | 11.18 | C |
| ATOM | 596 | O | ALA | A | 77 | 56.623 | 73.937 | -1.206 | 1.00 | 12.43 | O |
| ATOM | 597 | CB | ALA | A | 77 | 58.994 | 72.765 | 0.538 | 1.00 | 11.12 | C |
| ATOM | 598 | N | SER | A | 78 | 58.479 | 74.025 | -2.486 | 1.00 | 11.58 | N |
| ATOM | 599 | CA | SER | A | 78 | 58.012 | 75.143 | -3.280 | 1.00 | 11.77 | C |
| ATOM | 600 | C | SER | A | 78 | 57.156 | 74.776 | -4.430 | 1.00 | 11.86 | C |
| ATOM | 601 | O | SER | A | 78 | 56.580 | 75.649 | -5.116 | 1.00 | 13.37 | O |
| ATOM | 602 | CB | SER | A | 78 | 59.183 | 75.980 | -3.789 | 1.00 | 14.90 | C |
| ATOM | 603 | OG | SER | A | 78 | 59.903 | 76.593 | -2.778 | 1.00 | 17.91 | O |
| ATOM | 604 | N | ASN | A | 79 | 57.054 | 73.491 | -4.795 | 1.00 | 10.84 | N |
| ATOM | 605 | CA | ASN | A | 79 | 56.418 | 73.005 | -5.998 | 1.00 | 10.87 | C |
| ATOM | 606 | C | ASN | A | 79 | 55.456 | 71.859 | -5.693 | 1.00 | 10.31 | C |
| ATOM | 607 | O | ASN | A | 79 | 55.312 | 70.932 | -6.463 | 1.00 | 11.79 | O |
| ATOM | 608 | CB | ASN | A | 79 | 57.413 | 72.619 | -7.074 | 1.00 | 11.12 | C |
| ATOM | 609 | CG | ASN | A | 79 | 58.224 | 73.856 | -7.519 | 1.00 | 11.45 | C |
| ATOM | 610 | OD1 | ASN | A | 79 | 59.404 | 74.043 | -7.167 | 1.00 | 13.66 | O |
| ATOM | 611 | ND2 | ASN | A | 79 | 57.566 | 74.683 | -8.290 | 1.00 | 11.51 | N |
| ATOM | 612 | N | GLY | A | 80 | 54.730 | 71.939 | -4.578 | 1.00 | 11.80 | N |
| ATOM | 613 | CA | GLY | A | 80 | 53.642 | 71.032 | -4.256 | 1.00 | 11.06 | C |
| ATOM | 614 | C | GLY | A | 80 | 53.775 | 70.281 | -2.950 | 1.00 | 10.57 | C |
| ATOM | 615 | O | GLY | A | 80 | 52.776 | 69.758 | -2.464 | 1.00 | 10.67 | O |
| ATOM | 616 | N | GLY | A | 81 | 54.966 | 70.300 | -2.367 | 1.00 | 9.97 | N |
| ATOM | 617 | CA | GLY | A | 81 | 55.275 | 69.538 | -1.131 | 1.00 | 10.72 | C |
| ATOM | 618 | C | GLY | A | 81 | 55.041 | 70.271 | 0.176 | 1.00 | 11.35 | C |
| ATOM | 619 | O | GLY | A | 81 | 55.501 | 69.810 | 1.226 | 1.00 | 13.00 | O |
| ATOM | 620 | N | GLY | A | 82 | 54.374 | 71.410 | 0.136 | 1.00 | 10.83 | N |
| ATOM | 621 | CA | GLY | A | 82 | 54.131 | 72.164 | 1.366 | 1.00 | 12.82 | C |
| ATOM | 622 | C | GLY | A | 82 | 53.120 | 71.480 | 2.264 | 1.00 | 11.72 | C |
| ATOM | 623 | O | GLY | A | 82 | 52.377 | 70.583 | 1.857 | 1.00 | 13.80 | O |
| ATOM | 624 | N | TRP | A | 83 | 53.066 | 71.870 | 3.519 | 1.00 | 12.35 | N |
| ATOM | 625 | CA | TRP | A | 83 | 52.143 | 71.357 | 4.499 | 1.00 | 11.33 | C |
| ATOM | 626 | C | TRP | A | 83 | 51.465 | 72.489 | 5.297 | 1.00 | 13.26 | C |
| ATOM | 627 | O | TRP | A | 83 | 52.144 | 73.445 | 5.632 | 1.00 | 16.36 | O |
| ATOM | 628 | CB | TRP | A | 83 | 52.811 | 70.335 | 5.450 | 1.00 | 11.33 | C |
| ATOM | 629 | CG | TRP | A | 83 | 51.907 | 69.733 | 6.470 | 1.00 | 11.71 | C |
| ATOM | 630 | CD1 | TRP | A | 83 | 51.127 | 68.653 | 6.360 | 1.00 | 10.86 | C |
| ATOM | 631 | CD2 | TRP | A | 83 | 51.597 | 70.270 | 7.765 | 1.00 | 11.48 | C |
| ATOM | 632 | NE1 | TRP | A | 83 | 50.364 | 68.462 | 7.451 | 1.00 | 10.78 | N |
| ATOM | 633 | CE2 | TRP | A | 83 | 50.611 | 69.445 | 8.359 | 1.00 | 11.43 | C |
| ATOM | 634 | CE3 | TRP | A | 83 | 52.024 | 71.393 | 8.466 | 1.00 | 12.40 | C |
| ATOM | 635 | CZ2 | TRP | A | 83 | 50.111 | 69.687 | 9.653 | 1.00 | 11.74 | C |

Figure 6M

| ATOM | 636 | CZ3 | TRP | A | 83 | 51.502 | 71.654 | 9.751 | 1.00 | 12.34 | C |
|------|-----|-----|-----|---|----|--------|--------|-------|------|-------|---|
| ATOM | 637 | CH2 | TRP | A | 83 | 50.545 | 70.848 | 10.322 | 1.00 | 12.45 | C |
| ATOM | 638 | N | SER | A | 84 | 50.232 | 72.318 | 5.611 | 1.00 | 13.04 | N |
| ATOM | 639 | CA | SER | A | 84 | 49.470 | 73.144 | 6.579 | 1.00 | 14.80 | C |
| ATOM | 640 | C | SER | A | 84 | 48.511 | 72.216 | 7.289 | 1.00 | 14.24 | C |
| ATOM | 641 | O | SER | A | 84 | 48.124 | 71.162 | 6.790 | 1.00 | 12.43 | O |
| ATOM | 642 | CB | SER | A | 84 | 48.757 | 74.292 | 5.865 | 1.00 | 16.01 | C |
| ATOM | 643 | OG | SER | A | 84 | 47.704 | 73.769 | 5.171 | 1.00 | 18.96 | O |
| ATOM | 644 | N | LYS | A | 85 | 48.028 | 72.695 | 8.475 | 1.00 | 14.99 | N |
| ATOM | 645 | CA | LYS | A | 85 | 47.088 | 72.001 | 9.286 | 1.00 | 14.95 | C |
| ATOM | 646 | C | LYS | A | 85 | 45.670 | 72.216 | 8.849 | 1.00 | 15.79 | C |
| ATOM | 647 | O | LYS | A | 85 | 44.868 | 72.781 | 9.636 | 1.00 | 19.35 | O |
| ATOM | 648 | CB | LYS | A | 85 | 47.328 | 72.386 | 10.786 | 1.00 | 17.68 | C |
| ATOM | 649 | CG | LYS | A | 85 | 46.766 | 71.395 | 11.759 | 1.00 | 18.39 | C |
| ATOM | 650 | CD | LYS | A | 85 | 46.989 | 71.817 | 13.189 | 1.00 | 21.96 | C |
| ATOM | 651 | CE | LYS | A | 85 | 46.481 | 70.749 | 14.123 | 1.00 | 26.50 | C |
| ATOM | 652 | NZ | LYS | A | 85 | 47.253 | 71.037 | 15.362 | 1.00 | 36.47 | N |
| ATOM | 653 | N | ASP | A | 86 | 45.258 | 71.813 | 7.671 | 1.00 | 16.01 | N |
| ATOM | 654 | CA | ASP | A | 86 | 43.936 | 71.863 | 7.178 | 1.00 | 16.15 | C |
| ATOM | 655 | C | ASP | A | 86 | 43.169 | 70.593 | 7.412 | 1.00 | 16.81 | C |
| ATOM | 656 | O | ASP | A | 86 | 42.010 | 70.481 | 6.957 | 1.00 | 20.25 | O |
| ATOM | 657 | CB | ASP | A | 86 | 43.921 | 72.350 | 5.761 | 1.00 | 17.29 | C |
| ATOM | 658 | CG | ASP | A | 86 | 44.610 | 71.426 | 4.772 | 1.00 | 18.54 | C |
| ATOM | 659 | OD1 | ASP | A | 86 | 45.129 | 70.333 | 5.143 | 1.00 | 14.42 | O |
| ATOM | 660 | OD2 | ASP | A | 86 | 44.605 | 71.815 | 3.582 | 1.00 | 20.76 | O |
| ATOM | 661 | N | GLY | A | 87 | 43.744 | 69.565 | 8.018 | 1.00 | 16.40 | N |
| ATOM | 662 | CA | GLY | A | 87 | 43.092 | 68.312 | 8.262 | 1.00 | 17.50 | C |
| ATOM | 663 | C | GLY | A | 87 | 43.147 | 67.287 | 7.065 | 1.00 | 14.41 | C |
| ATOM | 664 | O | GLY | A | 87 | 42.744 | 66.141 | 7.235 | 1.00 | 15.93 | O |
| ATOM | 665 | N | ILE | A | 88 | 43.630 | 67.715 | 5.905 | 1.00 | 14.08 | N |
| ATOM | 666 | CA | ILE | A | 88 | 43.624 | 66.887 | 4.681 | 1.00 | 11.59 | C |
| ATOM | 667 | C | ILE | A | 88 | 45.013 | 66.787 | 4.025 | 1.00 | 10.89 | C |
| ATOM | 668 | O | ILE | A | 88 | 45.088 | 66.248 | 2.923 | 1.00 | 10.83 | O |
| ATOM | 669 | CB | ILE | A | 88 | 42.541 | 67.321 | 3.662 | 1.00 | 14.22 | C |
| ATOM | 670 | CG1 | ILE | A | 88 | 42.777 | 68.743 | 3.166 | 1.00 | 14.30 | C |
| ATOM | 671 | CG2 | ILE | A | 88 | 41.201 | 67.170 | 4.312 | 1.00 | 16.90 | C |
| ATOM | 672 | CD1 | ILE | A | 88 | 42.012 | 69.106 | 1.941 | 1.00 | 17.67 | C |
| ATOM | 673 | N | THR | A | 89 | 46.068 | 67.242 | 4.678 | 1.00 | 9.63 | N |
| ATOM | 674 | CA | THR | A | 89 | 47.355 | 67.231 | 4.043 | 1.00 | 10.03 | C |
| ATOM | 675 | C | THR | A | 89 | 48.290 | 66.353 | 4.817 | 1.00 | 8.75 | C |
| ATOM | 676 | O | THR | A | 89 | 48.544 | 66.561 | 6.033 | 1.00 | 10.00 | O |
| ATOM | 677 | CB | THR | A | 89 | 47.978 | 68.650 | 3.909 | 1.00 | 10.40 | C |
| ATOM | 678 | OG1 | THR | A | 89 | 47.004 | 69.537 | 3.406 | 1.00 | 12.80 | O |
| ATOM | 679 | CG2 | THR | A | 89 | 49.186 | 68.659 | 3.004 | 1.00 | 10.97 | C |
| ATOM | 680 | N | LEU | A | 90 | 48.865 | 65.344 | 4.178 | 1.00 | 8.28 | N |
| ATOM | 681 | CA | LEU | A | 90 | 49.882 | 64.496 | 4.766 | 1.00 | 8.25 | C |
| ATOM | 682 | C | LEU | A | 90 | 51.215 | 65.155 | 4.686 | 1.00 | 8.41 | C |
| ATOM | 683 | O | LEU | A | 90 | 51.454 | 65.939 | 3.722 | 1.00 | 9.95 | O |
| ATOM | 684 | CB | LEU | A | 90 | 49.941 | 63.169 | 4.039 | 1.00 | 9.35 | C |
| ATOM | 685 | CG | LEU | A | 90 | 48.684 | 62.310 | 4.242 | 1.00 | 10.23 | C |
| ATOM | 686 | CD1 | LEU | A | 90 | 48.639 | 61.159 | 3.253 | 1.00 | 12.43 | C |
| ATOM | 687 | CD2 | LEU | A | 90 | 48.559 | 61.794 | 5.637 | 1.00 | 11.63 | C |
| ATOM | 688 | N | PRO | A | 91 | 52.145 | 64.896 | 5.593 | 1.00 | 8.62 | N |

Figure 6N

```
ATOM    689  CA   PRO A  91      53.528  65.325   5.367  1.00  9.85       C
ATOM    690  C    PRO A  91      54.055  64.798   4.030  1.00  8.64       C
ATOM    691  O    PRO A  91      53.732  63.637   3.655  1.00  8.77       O
ATOM    692  CB   PRO A  91      54.313  64.717   6.552  1.00 10.34       C
ATOM    693  CG   PRO A  91      53.315  64.363   7.519  1.00 14.04       C
ATOM    694  CD   PRO A  91      52.048  64.041   6.795  1.00 10.87       C
ATOM    695  N    GLY A  92      54.837  65.581   3.338  1.00  8.17       N
ATOM    696  CA   GLY A  92      55.427  65.098   2.083  1.00  8.23       C
ATOM    697  C    GLY A  92      56.326  63.932   2.297  1.00  7.12       C
ATOM    698  O    GLY A  92      56.919  63.772   3.347  1.00  8.26       O
ATOM    699  N    ALA A  93      56.473  63.139   1.223  1.00  7.26       N
ATOM    700  CA   ALA A  93      57.296  61.907   1.240  1.00  6.96       C
ATOM    701  C    ALA A  93      58.540  62.066   0.382  1.00  7.06       C
ATOM    702  O    ALA A  93      58.493  62.578  -0.754  1.00  7.85       O
ATOM    703  CB   ALA A  93      56.478  60.722   0.838  1.00  7.38       C
ATOM    704  N    LEU A  94      59.650  61.591   0.929  1.00  6.95       N
ATOM    705  CA   LEU A  94      60.928  61.455   0.227  1.00  7.38       C
ATOM    706  C    LEU A  94      60.996  60.034  -0.354  1.00  7.73       C
ATOM    707  O    LEU A  94      61.103  59.039   0.403  1.00  7.82       O
ATOM    708  CB   LEU A  94      62.093  61.670   1.182  1.00  7.34       C
ATOM    709  CG   LEU A  94      63.468  61.482   0.561  1.00  8.17       C
ATOM    710  CD1  LEU A  94      63.781  62.470  -0.553  1.00  9.13       C
ATOM    711  CD2  LEU A  94      64.551  61.492   1.656  1.00  9.66       C
ATOM    712  N    ASP A  95      60.886  59.888  -1.671  1.00  7.48       N
ATOM    713  CA   ASP A  95      61.039  58.579  -2.356  1.00  7.68       C
ATOM    714  C    ASP A  95      62.458  58.389  -2.688  1.00  8.07       C
ATOM    715  O    ASP A  95      63.031  59.020  -3.618  1.00  7.87       O
ATOM    716  CB   ASP A  95      60.108  58.629  -3.582  1.00  8.60       C
ATOM    717  CG   ASP A  95      60.150  57.407  -4.445  1.00  9.41       C
ATOM    718  OD1  ASP A  95      61.120  56.607  -4.340  1.00 10.64       O
ATOM    719  OD2  ASP A  95      59.227  57.220  -5.262  1.00 13.82       O
ATOM    720  N   AILE A  96      63.138  57.586  -1.864  0.50  7.67       N
ATOM    721  CA  AILE A  96      64.564  57.351  -1.968  0.50  8.73       C
ATOM    722  C   AILE A  96      64.766  55.855  -2.183  0.50  8.99       C
ATOM    723  O   AILE A  96      64.504  54.980  -1.319  0.50  9.10       O
ATOM    724  CB  AILE A  96      65.271  57.946  -0.724  0.50  9.21       C
ATOM    725  CG1 AILE A  96      66.779  57.722  -0.615  0.50 10.37       C
ATOM    726  CG2 AILE A  96      64.747  57.482   0.628  0.50  9.70       C
ATOM    727  CD1 AILE A  96      67.560  58.453  -1.690  0.50  9.27       C
ATOM    728  N    GLU A  97      65.168  55.514  -3.399  1.00  9.36       N
ATOM    729  CA   GLU A  97      65.139  54.145  -3.862  1.00 10.45       C
ATOM    730  C    GLU A  97      66.149  53.955  -5.015  1.00  9.77       C
ATOM    731  O    GLU A  97      66.906  54.845  -5.340  1.00  9.44       O
ATOM    732  CB   GLU A  97      63.749  53.794  -4.325  1.00 12.48       C
ATOM    733  CG   GLU A  97      63.291  54.540  -5.533  1.00 13.18       C
ATOM    734  CD   GLU A  97      61.975  54.070  -6.077  1.00 14.89       C
ATOM    735  OE1  GLU A  97      61.998  53.030  -6.839  1.00 19.54       O
ATOM    736  OE2  GLU A  97      60.942  54.617  -5.821  1.00 12.80       O
ATOM    737  N    TYR A  98      66.149  52.741  -5.569  1.00 10.39       N
ATOM    738  CA   TYR A  98      67.091  52.397  -6.627  1.00 12.01       C
ATOM    739  C    TYR A  98      67.276  53.433  -7.670  1.00 12.50       C
ATOM    740  O    TYR A  98      66.271  53.888  -8.306  1.00 14.68       O
ATOM    741  CB   TYR A  98      66.617  51.141  -7.364  1.00 16.65       C
```

Figure 6O

```
ATOM    742  CG  TYR A  98      66.208  50.115  -6.445  1.00 17.77           C
ATOM    743  CD1 TYR A  98      67.124  49.226  -5.891  1.00 19.15           C
ATOM    744  CD2 TYR A  98      64.875  49.981  -6.089  1.00 18.63           C
ATOM    745  CE1 TYR A  98      66.712  48.258  -4.960  1.00 16.76           C
ATOM    746  CE2 TYR A  98      64.463  49.064  -5.169  1.00 18.78           C
ATOM    747  CZ  TYR A  98      65.402  48.174  -4.607  1.00 19.88           C
ATOM    748  OH  TYR A  98      64.930  47.290  -3.720  1.00 19.97           O
ATOM    749  N   ASN A  99      68.494  53.729  -8.014  1.00 11.97           N
ATOM    750  CA  ASN A  99      68.776  54.605  -9.131  1.00 12.55           C
ATOM    751  C   ASN A  99      68.311  54.029 -10.474  1.00 12.72           C
ATOM    752  O   ASN A  99      68.726  53.014 -10.854  1.00 12.92           O
ATOM    753  CB  ASN A  99      70.285  54.824  -9.147  1.00 11.83           C
ATOM    754  CG  ASN A  99      70.766  55.807 -10.153  1.00 11.60           C
ATOM    755  OD1 ASN A  99      69.898  56.454 -10.861  1.00 12.34           O
ATOM    756  ND2 ASN A  99      71.963  56.011 -10.239  1.00 10.95           N
ATOM    757  N   PRO A 100      67.296  54.639 -11.108  1.00 15.65           N
ATOM    758  CA  PRO A 100      66.918  54.121 -12.458  1.00 15.08           C
ATOM    759  C   PRO A 100      67.981  54.353 -13.521  1.00 13.33           C
ATOM    760  O   PRO A 100      67.742  53.769 -14.582  1.00 15.23           O
ATOM    761  CB  PRO A 100      65.674  54.910 -12.803  1.00 18.14           C
ATOM    762  CG  PRO A 100      66.009  56.229 -12.290  1.00 22.90           C
ATOM    763  CD  PRO A 100      66.676  55.941 -10.862  1.00 18.86           C
ATOM    764  N   ASN A 101      69.032  55.088 -13.343  1.00 12.02           N
ATOM    765  CA  ASN A 101      69.949  55.313 -14.321  1.00 12.72           C
ATOM    766  C   ASN A 101      71.367  55.419 -13.726  1.00 15.62           C
ATOM    767  O   ASN A 101      71.873  56.520 -13.516  1.00 17.93           O
ATOM    768  CB  ASN A 101      69.475  56.709 -14.858  1.00 18.85           C
ATOM    769  CG  ASN A 101      70.385  57.293 -15.865  1.00 17.73           C
ATOM    770  OD1 ASN A 101      71.098  56.545 -16.623  1.00 20.16           O
ATOM    771  ND2 ASN A 101      70.362  58.656 -15.995  1.00 19.41           N
ATOM    772  N   GLY A 102      71.905  54.303 -13.309  1.00 12.57           N
ATOM    773  CA  GLY A 102      73.278  54.223 -12.866  1.00 13.26           C
ATOM    774  C   GLY A 102      73.404  53.304 -11.631  1.00 11.80           C
ATOM    775  O   GLY A 102      72.579  52.493 -11.360  1.00 12.62           O
ATOM    776  N   ALA A 103      74.474  53.515 -10.888  1.00 12.41           N
ATOM    777  CA  ALA A 103      74.773  52.678  -9.700  1.00 11.68           C
ATOM    778  C   ALA A 103      73.623  52.803  -8.654  1.00 10.44           C
ATOM    779  O   ALA A 103      73.120  53.915  -8.442  1.00 11.37           O
ATOM    780  CB  ALA A 103      76.022  53.098  -9.136  1.00 13.80           C
ATOM    781  N   THR A 104      73.297  51.695  -8.031  1.00 10.31           N
ATOM    782  CA  THR A 104      72.172  51.571  -7.118  1.00 11.19           C
ATOM    783  C   THR A 104      72.136  52.713  -6.121  1.00 10.01           C
ATOM    784  O   THR A 104      71.041  53.315  -5.879  1.00  9.67           O
ATOM    785  CB  THR A 104      72.290  50.224  -6.322  1.00 12.71           C
ATOM    786  OG1 THR A 104      72.292  49.156  -7.295  1.00 16.30           O
ATOM    787  CG2 THR A 104      71.213  50.017  -5.299  1.00 14.79           C
ATOM    788  N   CYS A 105      73.274  53.063  -5.552  1.00  9.25           N
ATOM    789  CA  CYS A 105      73.389  54.035  -4.460  1.00 10.50           C
ATOM    790  C   CYS A 105      73.922  55.406  -4.909  1.00  9.74           C
ATOM    791  O   CYS A 105      74.329  56.201  -4.107  1.00 10.10           O
ATOM    792  CB  CYS A 105      74.210  53.485  -3.286  1.00 11.41           C
ATOM    793  SG  CYS A 105      73.668  51.873  -2.630  1.00 10.45           S
ATOM    794  N   TYR A 106      73.844  55.674  -6.256  1.00  9.49           N
```

Figure 6P

```
ATOM    795  CA   TYR A 106      74.035  57.001  -6.851  1.00 10.00      C
ATOM    796  C    TYR A 106      75.438  57.441  -6.732  1.00 11.56      C
ATOM    797  O    TYR A 106      75.758  58.631  -6.894  1.00 14.32      O
ATOM    798  CB   TYR A 106      73.039  58.071  -6.258  1.00 10.81      C
ATOM    799  CG   TYR A 106      71.590  57.764  -6.435  1.00  9.35      C
ATOM    800  CD1  TYR A 106      70.906  57.041  -5.542  1.00  9.32      C
ATOM    801  CD2  TYR A 106      70.863  58.253  -7.551  1.00  9.87      C
ATOM    802  CE1  TYR A 106      69.586  56.769  -5.680  1.00  9.87      C
ATOM    803  CE2  TYR A 106      69.606  58.035  -7.720  1.00 10.96      C
ATOM    804  CZ   TYR A 106      68.872  57.261  -6.801  1.00 10.72      C
ATOM    805  OH   TYR A 106      67.530  57.019  -6.996  1.00 10.26      O
ATOM    806  N    GLY A 107      76.385  56.554  -6.391  1.00 11.03      N
ATOM    807  CA   GLY A 107      77.768  56.968  -6.220  1.00 12.59      C
ATOM    808  C    GLY A 107      78.190  57.500  -4.857  1.00 11.20      C
ATOM    809  O    GLY A 107      79.286  58.018  -4.646  1.00 14.43      O
ATOM    810  N    LEU A 108      77.245  57.526  -3.883  1.00 10.39      N
ATOM    811  CA   LEU A 108      77.508  57.986  -2.537  1.00  9.99      C
ATOM    812  C    LEU A 108      77.920  56.876  -1.604  1.00  9.21      C
ATOM    813  O    LEU A 108      77.282  55.742  -1.704  1.00  9.80      O
ATOM    814  CB   LEU A 108      76.247  58.685  -1.955  1.00  9.30      C
ATOM    815  CG   LEU A 108      75.989  60.110  -2.420  1.00 10.75      C
ATOM    816  CD1  LEU A 108      75.524  60.291  -3.813  1.00 15.28      C
ATOM    817  CD2  LEU A 108      74.931  60.803  -1.539  1.00 11.39      C
ATOM    818  N    SER A 109      78.815  57.109  -0.676  1.00  8.87      N
ATOM    819  CA   SER A 109      79.074  56.135   0.359  1.00  9.15      C
ATOM    820  C    SER A 109      77.829  56.057   1.297  1.00  7.80      C
ATOM    821  O    SER A 109      76.972  56.914   1.285  1.00  8.60      O
ATOM    822  CB   SER A 109      80.252  56.543   1.186  1.00 10.32      C
ATOM    823  OG   SER A 109      79.984  57.755   1.911  1.00 10.88      O
ATOM    824  N    GLN A 110      77.810  55.028   2.137  1.00  7.95      N
ATOM    825  CA   GLN A 110      76.715  54.903   3.123  1.00  7.58      C
ATOM    826  C    GLN A 110      76.658  56.143   3.994  1.00  8.71      C
ATOM    827  O    GLN A 110      75.552  56.684   4.261  1.00  8.84      O
ATOM    828  CB   GLN A 110      76.921  53.651   3.941  1.00  7.60      C
ATOM    829  CG   GLN A 110      76.760  52.393   3.115  1.00  8.40      C
ATOM    830  CD   GLN A 110      77.021  51.082   3.855  1.00  9.00      C
ATOM    831  OE1  GLN A 110      77.699  51.100   4.920  1.00 10.48      O
ATOM    832  NE2  GLN A 110      76.608  49.967   3.350  1.00  8.64      N
ATOM    833  N    SER A 111      77.802  56.618   4.503  1.00  8.60      N
ATOM    834  CA   SER A 111      77.792  57.817   5.335  1.00  9.61      C
ATOM    835  C    SER A 111      77.354  59.029   4.621  1.00  9.15      C
ATOM    836  O    SER A 111      76.634  59.863   5.192  1.00  9.47      O
ATOM    837  CB   SER A 111      79.162  57.973   6.040  1.00 12.91      C
ATOM    838  OG   SER A 111      80.169  58.111   5.150  1.00 19.00      O
ATOM    839  N    ALA A 112      77.808  59.221   3.389  1.00  9.14      N
ATOM    840  CA   ALA A 112      77.399  60.368   2.593  1.00  9.79      C
ATOM    841  C    ALA A 112      75.901  60.343   2.346  1.00  9.22      C
ATOM    842  O    ALA A 112      75.233  61.401   2.317  1.00  8.94      O
ATOM    843  CB   ALA A 112      78.192  60.462   1.308  1.00 10.13      C
ATOM    844  N    MET A 113      75.361  59.143   2.111  1.00  8.20      N
ATOM    845  CA   MET A 113      73.885  59.048   1.848  1.00  8.63      C
ATOM    846  C    MET A 113      73.092  59.415   3.117  1.00  7.61      C
ATOM    847  O    MET A 113      72.093  60.123   3.031  1.00  8.51      O
```

Figure 6Q

```
ATOM    848  CB   MET A 113      73.552  57.619   1.390  1.00  7.57      C
ATOM    849  CG   MET A 113      72.082  57.459   0.964  1.00  7.91      C
ATOM    850  SD   MET A 113      71.579  58.481  -0.421  1.00  9.00      S
ATOM    851  CE   MET A 113      72.337  57.570  -1.790  1.00  9.78      C
ATOM    852  N    VAL A 114      73.503  58.943   4.266  1.00  8.04      N
ATOM    853  CA   VAL A 114      72.868  59.331   5.538  1.00  8.49      C
ATOM    854  C    VAL A 114      72.925  60.837   5.710  1.00  8.02      C
ATOM    855  O    VAL A 114      71.888  61.463   6.057  1.00  8.75      O
ATOM    856  CB   VAL A 114      73.441  58.578   6.736  1.00  9.15      C
ATOM    857  CG1  VAL A 114      72.924  59.133   8.059  1.00 10.10      C
ATOM    858  CG2  VAL A 114      73.169  57.078   6.657  1.00  9.71      C
ATOM    859  N    ASN A 115      74.066  61.441   5.440  1.00  8.59      N
ATOM    860  CA   ASN A 115      74.141  62.876   5.553  1.00  9.24      C
ATOM    861  C    ASN A 115      73.242  63.620   4.611  1.00  8.73      C
ATOM    862  O    ASN A 115      72.671  64.669   4.918  1.00  9.44      O
ATOM    863  CB   ASN A 115      75.605  63.368   5.441  1.00 10.80      C
ATOM    864  CG   ASN A 115      76.477  62.881   6.557  1.00 13.66      C
ATOM    865  OD1  ASN A 115      76.051  62.579   7.624  1.00 16.56      O
ATOM    866  ND2  ASN A 115      77.785  62.800   6.252  1.00 17.62      N
ATOM    867  N    TRP A 116      73.128  63.135   3.350  1.00  8.90      N
ATOM    868  CA   TRP A 116      72.249  63.711   2.358  1.00  8.54      C
ATOM    869  C    TRP A 116      70.783  63.662   2.807  1.00  8.75      C
ATOM    870  O    TRP A 116      70.060  64.662   2.748  1.00  8.80      O
ATOM    871  CB   TRP A 116      72.424  63.016   0.985  1.00  8.29      C
ATOM    872  CG   TRP A 116      71.742  63.646  -0.153  1.00  9.22      C
ATOM    873  CD1  TRP A 116      72.373  64.440  -1.092  1.00 10.31      C
ATOM    874  CD2  TRP A 116      70.393  63.560  -0.562  1.00  9.03      C
ATOM    875  NE1  TRP A 116      71.430  64.909  -1.980  1.00  9.79      N
ATOM    876  CE2  TRP A 116      70.207  64.423  -1.673  1.00  9.29      C
ATOM    877  CE3  TRP A 116      69.254  62.913  -0.064  1.00  9.14      C
ATOM    878  CZ2  TRP A 116      68.987  64.609  -2.306  1.00  9.93      C
ATOM    879  CZ3  TRP A 116      68.058  63.131  -0.674  1.00  9.73      C
ATOM    880  CH2  TRP A 116      67.927  63.939  -1.809  1.00 10.03      C
ATOM    881  N    ILE A 117      70.352  62.482   3.261  1.00  8.73      N
ATOM    882  CA   ILE A 117      68.968  62.340   3.765  1.00  8.12      C
ATOM    883  C    ILE A 117      68.754  63.248   4.992  1.00  8.10      C
ATOM    884  O    ILE A 117      67.700  63.892   5.036  1.00  8.83      O
ATOM    885  CB   ILE A 117      68.676  60.863   4.048  1.00  8.65      C
ATOM    886  CG1  ILE A 117      68.797  60.016   2.767  1.00  8.78      C
ATOM    887  CG2  ILE A 117      67.266  60.728   4.679  1.00  9.28      C
ATOM    888  CD1  ILE A 117      68.858  58.495   3.031  1.00  9.31      C
ATOM    889  N    GLU A 118      69.709  63.338   5.892  1.00  8.67      N
ATOM    890  CA   GLU A 118      69.583  64.235   7.049  1.00  8.77      C
ATOM    891  C    GLU A 118      69.370  65.639   6.581  1.00  9.08      C
ATOM    892  O    GLU A 118      68.543  66.398   7.151  1.00 10.18      O
ATOM    893  CB   GLU A 118      70.809  64.066   7.944  1.00  9.38      C
ATOM    894  CG   GLU A 118      70.802  64.938   9.212  1.00 12.22      C
ATOM    895  CD   GLU A 118      69.749  64.507  10.171  1.00 12.30      C
ATOM    896  OE1  GLU A 118      69.614  63.321  10.515  1.00 13.71      O
ATOM    897  OE2  GLU A 118      69.061  65.433  10.725  1.00 17.08      O
ATOM    898  N    ASP A 119      70.122  66.104   5.585  1.00  9.58      N
ATOM    899  CA   ASP A 119      69.987  67.442   5.043  1.00 10.53      C
ATOM    900  C    ASP A 119      68.602  67.668   4.468  1.00  9.55      C
```

Figure 6R

| | | | | | | | | | | |
|---|---|---|---|---|---|---|---|---|---|---|
| ATOM | 901 | O | ASP | A | 119 | 67.975 | 68.735 | 4.705 | 1.00 | 10.25 | O |
| ATOM | 902 | CB | ASP | A | 119 | 71.144 | 67.684 | 4.016 | 1.00 | 10.87 | C |
| ATOM | 903 | CG | ASP | A | 119 | 71.413 | 69.172 | 3.624 | 1.00 | 12.17 | C |
| ATOM | 904 | OD1 | ASP | A | 119 | 71.115 | 70.035 | 4.516 | 1.00 | 14.59 | O |
| ATOM | 905 | OD2 | ASP | A | 119 | 71.856 | 69.391 | 2.504 | 1.00 | 12.68 | O |
| ATOM | 906 | N | PHE | A | 120 | 68.066 | 66.737 | 3.707 | 1.00 | 8.85 | N |
| ATOM | 907 | CA | PHE | A | 120 | 66.721 | 66.836 | 3.185 | 1.00 | 8.22 | C |
| ATOM | 908 | C | PHE | A | 120 | 65.704 | 66.925 | 4.321 | 1.00 | 8.37 | C |
| ATOM | 909 | O | PHE | A | 120 | 64.844 | 67.786 | 4.346 | 1.00 | 8.31 | O |
| ATOM | 910 | CB | PHE | A | 120 | 66.402 | 65.636 | 2.245 | 1.00 | 8.22 | C |
| ATOM | 911 | CG | PHE | A | 120 | 65.041 | 65.751 | 1.572 | 1.00 | 8.32 | C |
| ATOM | 912 | CD1 | PHE | A | 120 | 63.862 | 65.423 | 2.290 | 1.00 | 8.64 | C |
| ATOM | 913 | CD2 | PHE | A | 120 | 64.916 | 66.175 | 0.276 | 1.00 | 9.11 | C |
| ATOM | 914 | CE1 | PHE | A | 120 | 62.645 | 65.620 | 1.711 | 1.00 | 9.54 | C |
| ATOM | 915 | CE2 | PHE | A | 120 | 63.672 | 66.323 | -0.327 | 1.00 | 9.92 | C |
| ATOM | 916 | CZ | PHE | A | 120 | 62.543 | 66.032 | 0.389 | 1.00 | 9.92 | C |
| ATOM | 917 | N | AVAL | A | 121 | 65.762 | 65.958 | 5.258 | 0.50 | 9.46 | N |
| ATOM | 918 | CA | AVAL | A | 121 | 64.701 | 65.905 | 6.268 | 0.50 | 9.79 | C |
| ATOM | 919 | C | AVAL | A | 121 | 64.713 | 67.123 | 7.213 | 0.50 | 9.73 | C |
| ATOM | 920 | O | AVAL | A | 121 | 63.670 | 67.650 | 7.559 | 0.50 | 9.67 | O |
| ATOM | 921 | CB | AVAL | A | 121 | 64.571 | 64.556 | 7.024 | 0.50 | 11.08 | C |
| ATOM | 922 | CG1 | AVAL | A | 121 | 64.992 | 63.355 | 6.213 | 0.50 | 12.21 | C |
| ATOM | 923 | CG2 | AVAL | A | 121 | 65.579 | 64.456 | 8.127 | 0.50 | 11.83 | C |
| ATOM | 924 | N | THR | A | 122 | 65.902 | 67.544 | 7.606 | 1.00 | 9.71 | N |
| ATOM | 925 | CA | THR | A | 122 | 66.015 | 68.744 | 8.484 | 1.00 | 11.38 | C |
| ATOM | 926 | C | THR | A | 122 | 65.606 | 69.977 | 7.770 | 1.00 | 10.39 | C |
| ATOM | 927 | O | THR | A | 122 | 64.872 | 70.837 | 8.341 | 1.00 | 11.71 | O |
| ATOM | 928 | CB | THR | A | 122 | 67.459 | 68.854 | 9.046 | 1.00 | 14.29 | C |
| ATOM | 929 | OG1 | THR | A | 122 | 67.737 | 67.751 | 9.912 | 1.00 | 18.37 | O |
| ATOM | 930 | CG2 | THR | A | 122 | 67.608 | 70.113 | 9.885 | 1.00 | 16.34 | C |
| ATOM | 931 | N | THR | A | 123 | 65.918 | 70.172 | 6.505 | 1.00 | 10.23 | N |
| ATOM | 932 | CA | THR | A | 123 | 65.466 | 71.308 | 5.735 | 1.00 | 10.48 | C |
| ATOM | 933 | C | THR | A | 123 | 63.964 | 71.291 | 5.591 | 1.00 | 10.11 | C |
| ATOM | 934 | O | THR | A | 123 | 63.303 | 72.336 | 5.735 | 1.00 | 10.51 | O |
| ATOM | 935 | CB | THR | A | 123 | 66.217 | 71.359 | 4.395 | 1.00 | 10.14 | C |
| ATOM | 936 | OG1 | THR | A | 123 | 67.662 | 71.459 | 4.616 | 1.00 | 11.42 | O |
| ATOM | 937 | CG2 | THR | A | 123 | 65.754 | 72.540 | 3.585 | 1.00 | 11.46 | C |
| ATOM | 938 | N | TYR | A | 124 | 63.379 | 70.173 | 5.180 | 1.00 | 10.12 | N |
| ATOM | 939 | CA | TYR | A | 124 | 61.956 | 70.070 | 5.018 | 1.00 | 9.13 | C |
| ATOM | 940 | C | TYR | A | 124 | 61.198 | 70.415 | 6.349 | 1.00 | 9.03 | C |
| ATOM | 941 | O | TYR | A | 124 | 60.199 | 71.112 | 6.304 | 1.00 | 9.86 | O |
| ATOM | 942 | CB | TYR | A | 124 | 61.574 | 68.631 | 4.546 | 1.00 | 9.40 | C |
| ATOM | 943 | CG | TYR | A | 124 | 60.113 | 68.484 | 4.180 | 1.00 | 8.91 | C |
| ATOM | 944 | CD1 | TYR | A | 124 | 59.614 | 68.889 | 2.943 | 1.00 | 9.63 | C |
| ATOM | 945 | CD2 | TYR | A | 124 | 59.216 | 68.013 | 5.103 | 1.00 | 8.82 | C |
| ATOM | 946 | CE1 | TYR | A | 124 | 58.289 | 68.867 | 2.655 | 1.00 | 9.97 | C |
| ATOM | 947 | CE2 | TYR | A | 124 | 57.860 | 67.964 | 4.827 | 1.00 | 9.19 | C |
| ATOM | 948 | CZ | TYR | A | 124 | 57.387 | 68.373 | 3.588 | 1.00 | 9.03 | C |
| ATOM | 949 | OH | TYR | A | 124 | 56.012 | 68.290 | 3.361 | 1.00 | 9.94 | O |
| ATOM | 950 | N | HIS | A | 125 | 61.651 | 69.859 | 7.411 | 1.00 | 9.44 | N |
| ATOM | 951 | CA | HIS | A | 125 | 61.058 | 70.142 | 8.761 | 1.00 | 10.58 | C |
| ATOM | 952 | C | HIS | A | 125 | 61.170 | 71.644 | 9.055 | 1.00 | 11.81 | C |
| ATOM | 953 | O | HIS | A | 125 | 60.218 | 72.249 | 9.621 | 1.00 | 12.74 | O |

Figure 6S

```
ATOM    954  CB  HIS A 125      61.688  69.226   9.786  1.00 11.51           C
ATOM    955  CG  HIS A 125      61.239  69.507  11.188  1.00 12.78           C
ATOM    956  ND1 HIS A 125      61.898  70.422  11.990  1.00 15.33           N
ATOM    957  CD2 HIS A 125      60.284  68.922  11.930  1.00 12.80           C
ATOM    958  CE1 HIS A 125      61.311  70.382  13.179  1.00 16.12           C
ATOM    959  NE2 HIS A 125      60.322  69.510  13.176  1.00 14.84           N
ATOM    960  N   GLY A 126      62.298  72.277   8.736  1.00 11.41           N
ATOM    961  CA  GLY A 126      62.458  73.722   9.004  1.00 11.57           C
ATOM    962  C   GLY A 126      61.480  74.515   8.205  1.00 12.31           C
ATOM    963  O   GLY A 126      61.026  75.598   8.638  1.00 14.25           O
ATOM    964  N   ILE A 127      61.083  74.119   7.024  1.00 12.46           N
ATOM    965  CA  ILE A 127      60.117  74.815   6.207  1.00 12.54           C
ATOM    966  C   ILE A 127      58.717  74.566   6.641  1.00 12.68           C
ATOM    967  O   ILE A 127      57.905  75.503   6.743  1.00 14.70           O
ATOM    968  CB  ILE A 127      60.275  74.412   4.705  1.00 13.53           C
ATOM    969  CG1 ILE A 127      61.669  74.809   4.163  1.00 13.85           C
ATOM    970  CG2 ILE A 127      59.184  75.008   3.826  1.00 14.90           C
ATOM    971  CD1 ILE A 127      62.022  74.089   2.871  1.00 14.58           C
ATOM    972  N   THR A 128      58.339  73.306   6.889  1.00 12.52           N
ATOM    973  CA  THR A 128      56.946  72.946   7.045  1.00 12.24           C
ATOM    974  C   THR A 128      56.505  72.709   8.488  1.00 13.19           C
ATOM    975  O   THR A 128      55.254  72.617   8.668  1.00 13.85           O
ATOM    976  CB  THR A 128      56.665  71.626   6.249  1.00 12.84           C
ATOM    977  OG1 THR A 128      57.303  70.520   6.883  1.00 11.04           O
ATOM    978  CG2 THR A 128      57.048  71.724   4.816  1.00 12.42           C
ATOM    979  N   SER A 129      57.401  72.443   9.416  1.00 11.97           N
ATOM    980  CA  SER A 129      57.175  71.982  10.761  1.00 13.64           C
ATOM    981  C   SER A 129      56.949  70.464  10.895  1.00 12.90           C
ATOM    982  O   SER A 129      56.785  69.948  12.004  1.00 14.05           O
ATOM    983  CB  SER A 129      56.053  72.720  11.539  1.00 14.54           C
ATOM    984  OG  SER A 129      54.765  72.223  11.190  1.00 16.89           O
ATOM    985  N   ARG A 130      56.991  69.730   9.762  1.00 10.94           N
ATOM    986  CA  ARG A 130      56.762  68.306   9.769  1.00 10.71           C
ATOM    987  C   ARG A 130      58.030  67.565   9.330  1.00 10.16           C
ATOM    988  O   ARG A 130      58.689  67.989   8.356  1.00 10.37           O
ATOM    989  CB  ARG A 130      55.607  67.874   8.845  1.00 10.59           C
ATOM    990  CG  ARG A 130      54.279  68.550   9.134  1.00 11.26           C
ATOM    991  CD  ARG A 130      53.784  68.290  10.538  1.00 12.79           C
ATOM    992  NE  ARG A 130      53.631  66.867  10.835  1.00 12.36           N
ATOM    993  CZ  ARG A 130      52.550  66.140  10.549  1.00 12.83           C
ATOM    994  NH1 ARG A 130      51.444  66.604   9.972  1.00 11.32           N
ATOM    995  NH2 ARG A 130      52.538  64.860  10.914  1.00 14.28           N
ATOM    996  N   TRP A 131      58.264  66.447   9.946  1.00  9.44           N
ATOM    997  CA  TRP A 131      59.262  65.490   9.431  1.00  8.88           C
ATOM    998  C   TRP A 131      58.610  64.823   8.210  1.00  9.12           C
ATOM    999  O   TRP A 131      57.472  64.395   8.285  1.00  9.54           O
ATOM   1000  CB  TRP A 131      59.613  64.438  10.478  1.00 10.04           C
ATOM   1001  CG  TRP A 131      60.284  65.038  11.712  1.00 10.34           C
ATOM   1002  CD1 TRP A 131      59.733  65.107  12.962  1.00 11.76           C
ATOM   1003  CD2 TRP A 131      61.531  65.707  11.785  1.00 10.87           C
ATOM   1004  NE1 TRP A 131      60.588  65.767  13.809  1.00 13.72           N
ATOM   1005  CE2 TRP A 131      61.707  66.165  13.130  1.00 12.63           C
ATOM   1006  CE3 TRP A 131      62.574  65.953  10.854  1.00 12.39           C
```

Figure 6T

| | | | | | | | | | | |
|---|---|---|---|---|---|---|---|---|---|---|
| ATOM | 1007 | CZ2 | TRP | A | 131 | 62.873 | 66.899 | 13.544 | 1.00 15.27 | C |
| ATOM | 1008 | CZ3 | TRP | A | 131 | 63.674 | 66.709 | 11.274 | 1.00 14.83 | C |
| ATOM | 1009 | CH2 | TRP | A | 131 | 63.822 | 67.124 | 12.606 | 1.00 15.77 | C |
| ATOM | 1010 | N | PRO | A | 132 | 59.344 | 64.618 | 7.125 | 1.00 8.23 | N |
| ATOM | 1011 | CA | PRO | A | 132 | 58.778 | 63.955 | 5.927 | 1.00 7.68 | C |
| ATOM | 1012 | C | PRO | A | 132 | 58.664 | 62.461 | 6.180 | 1.00 7.58 | C |
| ATOM | 1013 | O | PRO | A | 132 | 59.403 | 61.865 | 6.998 | 1.00 8.41 | O |
| ATOM | 1014 | CB | PRO | A | 132 | 59.788 | 64.254 | 4.822 | 1.00 8.62 | C |
| ATOM | 1015 | CG | PRO | A | 132 | 61.077 | 64.386 | 5.556 | 1.00 8.76 | C |
| ATOM | 1016 | CD | PRO | A | 132 | 60.782 | 64.989 | 6.921 | 1.00 8.46 | C |
| ATOM | 1017 | N | VAL | A | 133 | 57.744 | 61.824 | 5.451 | 1.00 7.38 | N |
| ATOM | 1018 | CA | VAL | A | 133 | 57.689 | 60.382 | 5.332 | 1.00 6.94 | C |
| ATOM | 1019 | C | VAL | A | 133 | 58.882 | 59.913 | 4.508 | 1.00 6.61 | C |
| ATOM | 1020 | O | VAL | A | 133 | 59.257 | 60.610 | 3.526 | 1.00 8.50 | O |
| ATOM | 1021 | CB | VAL | A | 133 | 56.351 | 60.015 | 4.688 | 1.00 7.75 | C |
| ATOM | 1022 | CG1 | VAL | A | 133 | 56.276 | 58.556 | 4.287 | 1.00 8.23 | C |
| ATOM | 1023 | CG2 | VAL | A | 133 | 55.216 | 60.382 | 5.622 | 1.00 8.86 | C |
| ATOM | 1024 | N | ILE | A | 134 | 59.494 | 58.781 | 4.799 | 1.00 6.68 | N |
| ATOM | 1025 | CA | ILE | A | 134 | 60.532 | 58.179 | 3.972 | 1.00 6.71 | C |
| ATOM | 1026 | C | ILE | A | 134 | 59.951 | 56.964 | 3.295 | 1.00 6.93 | C |
| ATOM | 1027 | O | ILE | A | 134 | 59.496 | 55.999 | 3.980 | 1.00 7.12 | O |
| ATOM | 1028 | CB | ILE | A | 134 | 61.777 | 57.810 | 4.778 | 1.00 7.98 | C |
| ATOM | 1029 | CG1 | ILE | A | 134 | 62.516 | 59.087 | 5.219 | 1.00 8.90 | C |
| ATOM | 1030 | CG2 | ILE | A | 134 | 62.734 | 56.867 | 3.967 | 1.00 9.20 | C |
| ATOM | 1031 | CD1 | ILE | A | 134 | 63.671 | 58.875 | 6.138 | 1.00 9.68 | C |
| ATOM | 1032 | N | TYR | A | 135 | 59.917 | 56.952 | 1.964 | 1.00 6.56 | N |
| ATOM | 1033 | CA | TYR | A | 135 | 59.539 | 55.804 | 1.120 | 1.00 6.92 | C |
| ATOM | 1034 | C | TYR | A | 135 | 60.800 | 55.142 | 0.611 | 1.00 6.99 | C |
| ATOM | 1035 | O | TYR | A | 135 | 61.690 | 55.781 | 0.012 | 1.00 7.70 | O |
| ATOM | 1036 | CB | TYR | A | 135 | 58.701 | 56.276 | -0.077 | 1.00 7.76 | C |
| ATOM | 1037 | CG | TYR | A | 135 | 58.477 | 55.173 | -1.131 | 1.00 7.38 | C |
| ATOM | 1038 | CD1 | TYR | A | 135 | 59.415 | 54.959 | -2.122 | 1.00 8.41 | C |
| ATOM | 1039 | CD2 | TYR | A | 135 | 57.369 | 54.378 | -1.110 | 1.00 8.41 | C |
| ATOM | 1040 | CE1 | TYR | A | 135 | 59.198 | 53.975 | -3.136 | 1.00 9.21 | C |
| ATOM | 1041 | CE2 | TYR | A | 135 | 57.125 | 53.445 | -2.100 | 1.00 8.26 | C |
| ATOM | 1042 | CZ | TYR | A | 135 | 58.054 | 53.217 | -3.103 | 1.00 7.91 | C |
| ATOM | 1043 | OH | TYR | A | 135 | 57.872 | 52.270 | -4.109 | 1.00 9.54 | O |
| ATOM | 1044 | N | THR | A | 136 | 60.912 | 53.858 | 0.876 | 1.00 6.49 | N |
| ATOM | 1045 | CA | THR | A | 136 | 62.069 | 53.075 | 0.440 | 1.00 6.83 | C |
| ATOM | 1046 | C | THR | A | 136 | 61.738 | 51.610 | 0.432 | 1.00 6.62 | C |
| ATOM | 1047 | O | THR | A | 136 | 60.628 | 51.182 | 0.745 | 1.00 7.62 | O |
| ATOM | 1048 | CB | THR | A | 136 | 63.285 | 53.386 | 1.350 | 1.00 7.97 | C |
| ATOM | 1049 | OG1 | THR | A | 136 | 64.519 | 52.978 | 0.707 | 1.00 8.30 | O |
| ATOM | 1050 | CG2 | THR | A | 136 | 63.210 | 52.792 | 2.746 | 1.00 8.09 | C |
| ATOM | 1051 | N | THR | A | 137 | 62.757 | 50.771 | 0.106 | 1.00 7.48 | N |
| ATOM | 1052 | CA | THR | A | 137 | 62.734 | 49.326 | 0.272 | 1.00 7.21 | C |
| ATOM | 1053 | C | THR | A | 137 | 63.764 | 48.939 | 1.274 | 1.00 7.67 | C |
| ATOM | 1054 | O | THR | A | 137 | 64.814 | 49.601 | 1.396 | 1.00 7.95 | O |
| ATOM | 1055 | CB | THR | A | 137 | 62.922 | 48.525 | -1.024 | 1.00 8.63 | C |
| ATOM | 1056 | OG1 | THR | A | 137 | 64.268 | 48.686 | -1.443 | 1.00 9.97 | O |
| ATOM | 1057 | CG2 | THR | A | 137 | 61.921 | 48.980 | -2.122 | 1.00 10.50 | C |
| ATOM | 1058 | N | THR | A | 138 | 63.576 | 47.820 | 1.983 | 1.00 7.47 | N |
| ATOM | 1059 | CA | THR | A | 138 | 64.583 | 47.402 | 2.967 | 1.00 8.57 | C |

Figure 6U

| | | | | | | | | | | |
|---|---|---|---|---|---|---|---|---|---|---|
| ATOM | 1060 | C | THR | A | 138 | 65.897 | 47.063 | 2.271 | 1.00 | 8.48 | C |
| ATOM | 1061 | O | THR | A | 138 | 66.964 | 47.414 | 2.830 | 1.00 | 8.95 | O |
| ATOM | 1062 | CB | THR | A | 138 | 64.065 | 46.280 | 3.826 | 1.00 | 8.38 | C |
| ATOM | 1063 | OG1 | THR | A | 138 | 62.916 | 46.734 | 4.491 | 1.00 | 9.26 | O |
| ATOM | 1064 | CG2 | THR | A | 138 | 65.082 | 45.788 | 4.856 | 1.00 | 9.62 | C |
| ATOM | 1065 | N | ASP | A | 139 | 65.848 | 46.465 | 1.131 | 1.00 | 8.54 | N |
| ATOM | 1066 | CA | ASP | A | 139 | 67.118 | 46.092 | 0.490 | 1.00 | 10.12 | C |
| ATOM | 1067 | C | ASP | A | 139 | 67.896 | 47.364 | 0.098 | 1.00 | 9.94 | C |
| ATOM | 1068 | O | ASP | A | 139 | 69.150 | 47.396 | 0.254 | 1.00 | 10.41 | O |
| ATOM | 1069 | CB | ASP | A | 139 | 66.823 | 45.289 | -0.790 | 1.00 | 14.63 | C |
| ATOM | 1070 | CG | ASP | A | 139 | 66.244 | 43.916 | -0.561 | 1.00 | 18.33 | C |
| ATOM | 1071 | OD1 | ASP | A | 139 | 66.517 | 43.410 | 0.538 | 1.00 | 23.27 | O |
| ATOM | 1072 | OD2 | ASP | A | 139 | 65.589 | 43.443 | -1.552 | 1.00 | 24.60 | O |
| ATOM | 1073 | N | TRP | A | 140 | 67.247 | 48.356 | -0.491 | 1.00 | 8.66 | N |
| ATOM | 1074 | CA | TRP | A | 140 | 67.967 | 49.571 | -0.890 | 1.00 | 8.35 | C |
| ATOM | 1075 | C | TRP | A | 140 | 68.510 | 50.232 | 0.364 | 1.00 | 7.65 | C |
| ATOM | 1076 | O | TRP | A | 140 | 69.678 | 50.686 | 0.405 | 1.00 | 8.16 | O |
| ATOM | 1077 | CB | TRP | A | 140 | 67.022 | 50.529 | -1.700 | 1.00 | 8.69 | C |
| ATOM | 1078 | CG | TRP | A | 140 | 67.802 | 51.715 | -2.215 | 1.00 | 8.94 | C |
| ATOM | 1079 | CD1 | TRP | A | 140 | 68.398 | 51.786 | -3.461 | 1.00 | 9.42 | C |
| ATOM | 1080 | CD2 | TRP | A | 140 | 68.129 | 52.960 | -1.537 | 1.00 | 8.00 | C |
| ATOM | 1081 | NE1 | TRP | A | 140 | 69.032 | 52.991 | -3.594 | 1.00 | 9.29 | N |
| ATOM | 1082 | CE2 | TRP | A | 140 | 68.933 | 53.724 | -2.422 | 1.00 | 7.92 | C |
| ATOM | 1083 | CE3 | TRP | A | 140 | 67.856 | 53.473 | -0.255 | 1.00 | 7.84 | C |
| ATOM | 1084 | CZ2 | TRP | A | 140 | 69.451 | 54.933 | -2.091 | 1.00 | 8.67 | C |
| ATOM | 1085 | CZ3 | TRP | A | 140 | 68.388 | 54.667 | 0.098 | 1.00 | 8.42 | C |
| ATOM | 1086 | CH2 | TRP | A | 140 | 69.201 | 55.418 | -0.821 | 1.00 | 8.52 | C |
| ATOM | 1087 | N | TRP | A | 141 | 67.686 | 50.366 | 1.377 | 1.00 | 7.82 | N |
| ATOM | 1088 | CA | TRP | A | 141 | 68.090 | 51.078 | 2.601 | 1.00 | 7.33 | C |
| ATOM | 1089 | C | TRP | A | 141 | 69.286 | 50.382 | 3.285 | 1.00 | 6.82 | C |
| ATOM | 1090 | O | TRP | A | 141 | 70.229 | 51.002 | 3.748 | 1.00 | 7.73 | O |
| ATOM | 1091 | CB | TRP | A | 141 | 66.908 | 51.109 | 3.581 | 1.00 | 7.11 | C |
| ATOM | 1092 | CG | TRP | A | 141 | 67.115 | 52.042 | 4.728 | 1.00 | 7.72 | C |
| ATOM | 1093 | CD1 | TRP | A | 141 | 67.533 | 51.755 | 6.031 | 1.00 | 7.83 | C |
| ATOM | 1094 | CD2 | TRP | A | 141 | 66.965 | 53.443 | 4.704 | 1.00 | 6.56 | C |
| ATOM | 1095 | NE1 | TRP | A | 141 | 67.602 | 52.865 | 6.760 | 1.00 | 7.80 | N |
| ATOM | 1096 | CE2 | TRP | A | 141 | 67.290 | 53.935 | 5.996 | 1.00 | 6.97 | C |
| ATOM | 1097 | CE3 | TRP | A | 141 | 66.572 | 54.345 | 3.741 | 1.00 | 7.06 | C |
| ATOM | 1098 | CZ2 | TRP | A | 141 | 67.224 | 55.249 | 6.300 | 1.00 | 8.00 | C |
| ATOM | 1099 | CZ3 | TRP | A | 141 | 66.520 | 55.652 | 4.038 | 1.00 | 7.96 | C |
| ATOM | 1100 | CH2 | TRP | A | 141 | 66.818 | 56.117 | 5.325 | 1.00 | 7.62 | C |
| ATOM | 1101 | N | THR | A | 142 | 69.265 | 49.050 | 3.247 | 1.00 | 7.39 | N |
| ATOM | 1102 | CA | THR | A | 142 | 70.350 | 48.286 | 3.901 | 1.00 | 8.14 | C |
| ATOM | 1103 | C | THR | A | 142 | 71.668 | 48.507 | 3.156 | 1.00 | 8.17 | C |
| ATOM | 1104 | O | THR | A | 142 | 72.698 | 48.887 | 3.801 | 1.00 | 8.63 | O |
| ATOM | 1105 | CB | THR | A | 142 | 69.951 | 46.821 | 3.957 | 1.00 | 8.43 | C |
| ATOM | 1106 | OG1 | THR | A | 142 | 68.790 | 46.668 | 4.795 | 1.00 | 9.41 | O |
| ATOM | 1107 | CG2 | THR | A | 142 | 71.070 | 45.956 | 4.560 | 1.00 | 9.86 | C |
| ATOM | 1108 | N | AGLN | A | 143 | 71.693 | 48.444 | 1.832 | 0.50 | 9.27 | N |
| ATOM | 1109 | CA | AGLN | A | 143 | 72.973 | 48.615 | 1.159 | 0.50 | 10.79 | C |
| ATOM | 1110 | C | AGLN | A | 143 | 73.413 | 50.088 | 1.067 | 0.50 | 9.53 | C |
| ATOM | 1111 | O | AGLN | A | 143 | 74.593 | 50.432 | 1.188 | 0.50 | 10.97 | O |
| ATOM | 1112 | CB | AGLN | A | 143 | 72.912 | 47.844 | -0.130 | 0.50 | 14.10 | C |

Figure 6V

```
ATOM   1113  CG  AGLN A 143      73.316  48.615  -1.314  0.50 16.88    C
ATOM   1114  CD  AGLN A 143      73.552  47.829  -2.587  0.50 14.74    C
ATOM   1115  OE1 AGLN A 143      74.335  48.269  -3.420  0.50 16.26    O
ATOM   1116  NE2 AGLN A 143      72.839  46.724  -2.794  0.50 11.84    N
ATOM   1117  N    CYS A 144      72.461  50.992   0.878  1.00  7.66    N
ATOM   1118  CA   CYS A 144      72.846  52.345   0.586  1.00  7.76    C
ATOM   1119  C    CYS A 144      73.069  53.220   1.798  1.00  7.70    C
ATOM   1120  O    CYS A 144      73.740  54.251   1.732  1.00  9.47    O
ATOM   1121  CB   CYS A 144      71.927  53.008  -0.459  1.00  7.71    C
ATOM   1122  SG   CYS A 144      71.792  52.160  -2.007  1.00  9.72    S
ATOM   1123  N    THR A 145      72.447  52.882   2.942  1.00  7.57    N
ATOM   1124  CA   THR A 145      72.617  53.623   4.157  1.00  7.94    C
ATOM   1125  C    THR A 145      73.407  52.881   5.204  1.00  8.83    C
ATOM   1126  O    THR A 145      73.609  53.378   6.330  1.00  9.32    O
ATOM   1127  CB   THR A 145      71.334  54.193   4.781  1.00  8.11    C
ATOM   1128  OG1  THR A 145      70.596  53.130   5.416  1.00  8.01    O
ATOM   1129  CG2  THR A 145      70.459  54.900   3.756  1.00  8.69    C
ATOM   1130  N    GLY A 146      73.755  51.621   4.962  1.00  9.09    N
ATOM   1131  CA   GLY A 146      74.297  50.777   6.019  1.00  8.91    C
ATOM   1132  C    GLY A 146      73.187  50.362   6.994  1.00  9.60    C
ATOM   1133  O    GLY A 146      73.489  50.083   8.190  1.00 11.18    O
ATOM   1134  N    ASN A 147      71.955  50.352   6.536  1.00  9.50    N
ATOM   1135  CA   ASN A 147      70.827  50.086   7.402  1.00  8.82    C
ATOM   1136  C    ASN A 147      70.738  51.048   8.567  1.00  8.59    C
ATOM   1137  O    ASN A 147      70.702  50.627   9.762  1.00 10.07    O
ATOM   1138  CB   ASN A 147      70.735  48.606   7.833  1.00  8.94    C
ATOM   1139  CG   ASN A 147      69.297  48.147   8.061  1.00  9.13    C
ATOM   1140  OD1  ASN A 147      68.328  48.862   7.823  1.00  9.32    O
ATOM   1141  ND2  ASN A 147      69.170  46.924   8.534  1.00 10.40    N
ATOM   1142  N    SER A 148      70.722  52.329   8.275  1.00  8.22    N
ATOM   1143  CA   SER A 148      70.748  53.331   9.312  1.00  9.16    C
ATOM   1144  C    SER A 148      69.428  53.486  10.059  1.00  7.72    C
ATOM   1145  O    SER A 148      68.355  53.561   9.438  1.00  8.80    O
ATOM   1146  CB   SER A 148      71.059  54.714   8.669  1.00 10.29    C
ATOM   1147  OG   SER A 148      71.070  55.715   9.623  1.00 10.25    O
ATOM   1148  N    ASN A 149      69.528  53.603  11.383  1.00  7.82    N
ATOM   1149  CA   ASN A 149      68.345  53.940  12.216  1.00  8.52    C
ATOM   1150  C    ASN A 149      68.249  55.388  12.503  1.00  8.47    C
ATOM   1151  O    ASN A 149      67.396  55.761  13.366  1.00  9.50    O
ATOM   1152  CB   ASN A 149      68.340  53.102  13.496  1.00  8.53    C
ATOM   1153  CG   ASN A 149      69.595  53.301  14.334  1.00  8.72    C
ATOM   1154  OD1  ASN A 149      70.345  54.218  14.149  1.00  9.62    O
ATOM   1155  ND2  ASN A 149      69.763  52.393  15.331  1.00  9.48    N
ATOM   1156  N    ARG A 150      68.956  56.273  11.812  1.00  9.14    N
ATOM   1157  CA   ARG A 150      68.995  57.666  12.132  1.00  9.87    C
ATOM   1158  C    ARG A 150      67.665  58.436  12.083  1.00 10.12    C
ATOM   1159  O    ARG A 150      67.516  59.452  12.770  1.00 10.54    O
ATOM   1160  CB   ARG A 150      70.005  58.372  11.176  1.00 12.81    C
ATOM   1161  CG   ARG A 150      70.094  59.809  11.483  1.00 17.89    C
ATOM   1162  CD   ARG A 150      70.991  60.511  10.736  1.00 27.57    C
ATOM   1163  NE   ARG A 150      72.183  60.272  11.381  1.00 30.26    N
ATOM   1164  CZ   ARG A 150      73.019  61.229  11.506  1.00 29.85    C
ATOM   1165  NH1  ARG A 150      72.599  62.385  11.112  1.00 26.18    N
```

Figure 6W

```
ATOM   1166  NH2  ARG A 150    74.228  60.972  11.904  1.00  24.41    N
ATOM   1167  N    PHE A 151    66.727  57.975  11.234  1.00   8.94    N
ATOM   1168  CA   PHE A 151    65.511  58.699  10.942  1.00   9.20    C
ATOM   1169  C    PHE A 151    64.316  58.046  11.592  1.00   9.78    C
ATOM   1170  O    PHE A 151    63.206  58.629  11.487  1.00  10.61    O
ATOM   1171  CB   PHE A 151    65.318  58.834   9.394  1.00   9.54    C
ATOM   1172  CG   PHE A 151    66.549  59.379   8.730  1.00   8.97    C
ATOM   1173  CD1  PHE A 151    66.962  60.676   8.930  1.00   9.62    C
ATOM   1174  CD2  PHE A 151    67.395  58.554   8.064  1.00  10.03    C
ATOM   1175  CE1  PHE A 151    68.177  61.087   8.425  1.00  11.75    C
ATOM   1176  CE2  PHE A 151    68.612  58.988   7.570  1.00  11.10    C
ATOM   1177  CZ   PHE A 151    68.989  60.246   7.734  1.00  11.24    C
ATOM   1178  N    ALA A 152    64.446  56.924  12.216  1.00   9.12    N
ATOM   1179  CA   ALA A 152    63.303  56.122  12.653  1.00  10.60    C
ATOM   1180  C    ALA A 152    62.451  56.794  13.716  1.00  10.88    C
ATOM   1181  O    ALA A 152    61.282  56.398  13.820  1.00  14.19    O
ATOM   1182  CB   ALA A 152    63.765  54.770  13.117  1.00  12.67    C
ATOM   1183  N    ASN A 153    63.002  57.683  14.492  1.00   9.62    N
ATOM   1184  CA   ASN A 153    62.207  58.355  15.571  1.00  10.68    C
ATOM   1185  C    ASN A 153    61.743  59.711  15.129  1.00  10.51    C
ATOM   1186  O    ASN A 153    61.183  60.499  15.944  1.00  12.66    O
ATOM   1187  CB   ASN A 153    62.963  58.309  16.915  1.00  12.44    C
ATOM   1188  CG   ASN A 153    63.022  56.856  17.500  1.00  13.49    C
ATOM   1189  OD1  ASN A 153    62.043  56.431  18.122  1.00  17.87    O
ATOM   1190  ND2  ASN A 153    64.009  56.095  17.257  1.00  15.95    N
ATOM   1191  N    ARG A 154    61.844  60.072  13.840  1.00   9.21    N
ATOM   1192  CA   ARG A 154    61.306  61.260  13.287  1.00  10.27    C
ATOM   1193  C    ARG A 154    60.346  61.001  12.128  1.00   9.25    C
ATOM   1194  O    ARG A 154    59.260  61.571  12.057  1.00  10.51    O
ATOM   1195  CB   ARG A 154    62.407  62.252  12.858  1.00  10.77    C
ATOM   1196  CG   ARG A 154    63.126  62.870  14.059  1.00  11.16    C
ATOM   1197  CD   ARG A 154    64.319  63.706  13.595  1.00  12.25    C
ATOM   1198  NE   ARG A 154    65.378  62.841  13.090  1.00  10.50    N
ATOM   1199  CZ   ARG A 154    66.431  63.233  12.360  1.00  12.16    C
ATOM   1200  NH1  ARG A 154    66.593  64.510  12.096  1.00  12.15    N
ATOM   1201  NH2  ARG A 154    67.383  62.386  12.052  1.00  11.85    N
ATOM   1202  N    CYS A 155    60.821  60.285  11.119  1.00   8.58    N
ATOM   1203  CA   CYS A 155    60.159  60.147   9.835  1.00   8.25    C
ATOM   1204  C    CYS A 155    59.308  58.880   9.830  1.00   8.71    C
ATOM   1205  O    CYS A 155    59.844  57.783  10.008  1.00   9.78    O
ATOM   1206  CB   CYS A 155    61.200  60.012   8.737  1.00   9.18    C
ATOM   1207  SG   CYS A 155    62.277  61.473   8.622  1.00  10.10    S
ATOM   1208  N    PRO A 156    57.982  59.004   9.520  1.00   7.59    N
ATOM   1209  CA   PRO A 156    57.171  57.776   9.323  1.00   7.63    C
ATOM   1210  C    PRO A 156    57.740  56.961   8.141  1.00   7.08    C
ATOM   1211  O    PRO A 156    58.209  57.549   7.155  1.00   8.52    O
ATOM   1212  CB   PRO A 156    55.799  58.326   9.005  1.00   9.24    C
ATOM   1213  CG   PRO A 156    55.772  59.736   9.551  1.00   9.64    C
ATOM   1214  CD   PRO A 156    57.200  60.233   9.381  1.00   8.70    C
ATOM   1215  N    LEU A 157    57.655  55.646   8.223  1.00   7.48    N
ATOM   1216  CA   LEU A 157    58.126  54.741   7.164  1.00   6.89    C
ATOM   1217  C    LEU A 157    57.026  54.382   6.206  1.00   6.26    C
ATOM   1218  O    LEU A 157    55.948  53.904   6.626  1.00   7.26    O
```

Figure 6X

| | | | | | | | | | |
|---|---|---|---|---|---|---|---|---|---|
| ATOM | 1219 | CB  | LEU | A | 157 | 58.696 | 53.491 |  7.799 | 1.00  6.90 | C |
| ATOM | 1220 | CG  | LEU | A | 157 | 59.187 | 52.421 |  6.824 | 1.00  7.83 | C |
| ATOM | 1221 | CD1 | LEU | A | 157 | 60.389 | 52.941 |  6.000 | 1.00  8.27 | C |
| ATOM | 1222 | CD2 | LEU | A | 157 | 59.550 | 51.157 |  7.544 | 1.00  8.16 | C |
| ATOM | 1223 | N   | TRP | A | 158 | 57.286 | 54.580 |  4.908 | 1.00  6.49 | N |
| ATOM | 1224 | CA  | TRP | A | 158 | 56.466 | 54.080 |  3.802 | 1.00  6.34 | C |
| ATOM | 1225 | C   | TRP | A | 158 | 57.290 | 53.006 |  3.112 | 1.00  6.40 | C |
| ATOM | 1226 | O   | TRP | A | 158 | 58.234 | 53.312 |  2.375 | 1.00  7.33 | O |
| ATOM | 1227 | CB  | TRP | A | 158 | 56.068 | 55.233 |  2.902 | 1.00  6.66 | C |
| ATOM | 1228 | CG  | TRP | A | 158 | 55.190 | 54.925 |  1.733 | 1.00  6.59 | C |
| ATOM | 1229 | CD1 | TRP | A | 158 | 54.599 | 53.725 |  1.392 | 1.00  6.90 | C |
| ATOM | 1230 | CD2 | TRP | A | 158 | 54.777 | 55.881 |  0.750 | 1.00  6.88 | C |
| ATOM | 1231 | NE1 | TRP | A | 158 | 53.859 | 53.893 |  0.250 | 1.00  7.46 | N |
| ATOM | 1232 | CE2 | TRP | A | 158 | 53.964 | 55.189 | -0.150 | 1.00  6.74 | C |
| ATOM | 1233 | CE3 | TRP | A | 158 | 55.099 | 57.218 |  0.486 | 1.00  7.30 | C |
| ATOM | 1234 | CZ2 | TRP | A | 158 | 53.498 | 55.823 | -1.351 | 1.00  7.99 | C |
| ATOM | 1235 | CZ3 | TRP | A | 158 | 54.625 | 57.810 | -0.639 | 1.00  8.48 | C |
| ATOM | 1236 | CH2 | TRP | A | 158 | 53.784 | 57.105 | -1.530 | 1.00  8.40 | C |
| ATOM | 1237 | N   | ILE | A | 159 | 57.010 | 51.729 |  3.427 | 1.00  6.44 | N |
| ATOM | 1238 | CA  | ILE | A | 159 | 57.780 | 50.624 |  2.931 | 1.00  6.68 | C |
| ATOM | 1239 | C   | ILE | A | 159 | 57.152 | 50.030 |  1.686 | 1.00  6.52 | C |
| ATOM | 1240 | O   | ILE | A | 159 | 55.949 | 49.858 |  1.633 | 1.00  6.82 | O |
| ATOM | 1241 | CB  | ILE | A | 159 | 57.999 | 49.575 |  4.060 | 1.00  7.44 | C |
| ATOM | 1242 | CG1 | ILE | A | 159 | 59.088 | 48.568 |  3.749 | 1.00  9.07 | C |
| ATOM | 1243 | CG2 | ILE | A | 159 | 56.674 | 48.854 |  4.442 | 1.00  8.52 | C |
| ATOM | 1244 | CD1 | ILE | A | 159 | 60.462 | 49.157 |  3.713 | 1.00 10.33 | C |
| ATOM | 1245 | N   | ALA | A | 160 | 57.973 | 49.648 |  0.707 | 1.00  6.90 | N |
| ATOM | 1246 | CA  | ALA | A | 160 | 57.491 | 48.996 | -0.507 | 1.00  6.93 | C |
| ATOM | 1247 | C   | ALA | A | 160 | 57.891 | 47.536 | -0.503 | 1.00  7.44 | C |
| ATOM | 1248 | O   | ALA | A | 160 | 59.114 | 47.234 | -0.415 | 1.00  7.83 | O |
| ATOM | 1249 | CB  | ALA | A | 160 | 57.957 | 49.663 | -1.770 | 1.00  7.55 | C |
| ATOM | 1250 | N   | ARG | A | 161 | 56.971 | 46.633 | -0.681 | 1.00  7.07 | N |
| ATOM | 1251 | CA  | ARG | A | 161 | 57.228 | 45.182 | -0.876 | 1.00  7.64 | C |
| ATOM | 1252 | C   | ARG | A | 161 | 55.983 | 44.552 | -1.476 | 1.00  7.38 | C |
| ATOM | 1253 | O   | ARG | A | 161 | 54.926 | 44.551 | -0.851 | 1.00  7.18 | O |
| ATOM | 1254 | CB  | ARG | A | 161 | 57.653 | 44.446 |  0.426 | 1.00 11.16 | C |
| ATOM | 1255 | CG  | ARG | A | 161 | 57.996 | 42.952 | -0.048 | 1.00 14.52 | C |
| ATOM | 1256 | CD  | ARG | A | 161 | 59.288 | 42.073 |  0.020 | 1.00 24.94 | C |
| ATOM | 1257 | NE  | ARG | A | 161 | 58.613 | 40.938 |  0.630 | 1.00 20.34 | N |
| ATOM | 1258 | CZ  | ARG | A | 161 | 58.679 | 39.746 |  1.150 | 1.00 16.04 | C |
| ATOM | 1259 | NH1 | ARG | A | 161 | 59.148 | 38.679 |  0.549 | 1.00 16.05 | N |
| ATOM | 1260 | NH2 | ARG | A | 161 | 57.833 | 39.613 |  2.161 | 1.00 13.84 | N |
| ATOM | 1261 | N   | TYR | A | 162 | 56.119 | 44.000 | -2.682 | 1.00  8.12 | N |
| ATOM | 1262 | CA  | TYR | A | 162 | 54.983 | 43.506 | -3.402 | 1.00  8.21 | C |
| ATOM | 1263 | C   | TYR | A | 162 | 54.855 | 41.986 | -3.156 | 1.00  8.93 | C |
| ATOM | 1264 | O   | TYR | A | 162 | 55.403 | 41.152 | -3.889 | 1.00 10.04 | O |
| ATOM | 1265 | CB  | TYR | A | 162 | 55.088 | 43.818 | -4.902 | 1.00  7.99 | C |
| ATOM | 1266 | CG  | TYR | A | 162 | 55.204 | 45.268 | -5.248 | 1.00  7.52 | C |
| ATOM | 1267 | CD1 | TYR | A | 162 | 54.938 | 46.288 | -4.332 | 1.00  7.57 | C |
| ATOM | 1268 | CD2 | TYR | A | 162 | 55.684 | 45.666 | -6.502 | 1.00  9.27 | C |
| ATOM | 1269 | CE1 | TYR | A | 162 | 55.107 | 47.628 | -4.631 | 1.00  8.40 | C |
| ATOM | 1270 | CE2 | TYR | A | 162 | 55.824 | 47.025 | -6.812 | 1.00  9.38 | C |
| ATOM | 1271 | CZ  | TYR | A | 162 | 55.548 | 47.985 | -5.863 | 1.00  8.85 | C |

Figure 6Y

```
ATOM   1272  OH   TYR A 162      55.737  49.326  -6.217  1.00 10.83           O
ATOM   1273  N    ALA A 163      54.227  41.622  -2.043  1.00  8.15           N
ATOM   1274  CA   ALA A 163      54.183  40.282  -1.516  1.00  8.27           C
ATOM   1275  C    ALA A 163      52.980  40.193  -0.543  1.00  8.13           C
ATOM   1276  O    ALA A 163      52.344  41.159  -0.207  1.00  8.47           O
ATOM   1277  CB   ALA A 163      55.493  39.965  -0.777  1.00  9.16           C
ATOM   1278  N    SER A 164      52.721  38.965  -0.080  1.00  8.68           N
ATOM   1279  CA   SER A 164      51.592  38.716   0.806  1.00  7.85           C
ATOM   1280  C    SER A 164      51.825  39.183   2.243  1.00  8.63           C
ATOM   1281  O    SER A 164      50.897  39.277   3.049  1.00  9.04           O
ATOM   1282  CB   SER A 164      51.249  37.204   0.799  1.00  9.72           C
ATOM   1283  OG   SER A 164      52.337  36.471   1.284  1.00  9.90           O
ATOM   1284  N    SER A 165      53.070  39.535   2.600  1.00  8.88           N
ATOM   1285  CA   SER A 165      53.404  40.129   3.902  1.00  9.17           C
ATOM   1286  C    SER A 165      54.514  41.118   3.656  1.00  8.98           C
ATOM   1287  O    SER A 165      55.255  41.083   2.656  1.00  9.75           O
ATOM   1288  CB   SER A 165      53.842  39.054   4.942  1.00 12.90           C
ATOM   1289  OG   SER A 165      54.912  38.405   4.555  1.00 15.18           O
ATOM   1290  N   AVAL A 166      54.629  42.037   4.612  0.50  8.77           N
ATOM   1291  CA  AVAL A 166      55.534  43.181   4.447  0.50  9.54           C
ATOM   1292  C   AVAL A 166      57.000  42.831   4.522  0.50 10.75           C
ATOM   1293  O   AVAL A 166      57.773  43.606   3.860  0.50 12.11           O
ATOM   1294  CB  AVAL A 166      55.128  44.287   5.416  0.50  8.19           C
ATOM   1295  CG1 AVAL A 166      55.552  43.990   6.845  0.50  8.43           C
ATOM   1296  CG2 AVAL A 166      55.707  45.620   4.988  0.50  7.62           C
ATOM   1297  N    GLY A 167      57.390  41.725   5.168  1.00 12.46           N
ATOM   1298  CA   GLY A 167      58.759  41.276   5.308  1.00 14.46           C
ATOM   1299  C    GLY A 167      59.561  42.132   6.335  1.00 13.77           C
ATOM   1300  O    GLY A 167      59.065  42.864   7.135  1.00 13.29           O
ATOM   1301  N    THR A 168      60.856  41.993   6.254  1.00 13.21           N
ATOM   1302  CA   THR A 168      61.802  42.705   7.112  1.00 13.24           C
ATOM   1303  C    THR A 168      61.705  44.244   6.971  1.00  9.41           C
ATOM   1304  O    THR A 168      61.718  44.700   5.854  1.00 10.41           O
ATOM   1305  CB   THR A 168      63.247  42.293   6.731  1.00 17.02           C
ATOM   1306  OG1  THR A 168      63.348  40.839   6.618  1.00 21.31           O
ATOM   1307  CG2  THR A 168      64.316  42.899   7.626  1.00 16.56           C
ATOM   1308  N    LEU A 169      61.674  44.967   8.053  1.00 10.02           N
ATOM   1309  CA   LEU A 169      61.696  46.472   8.038  1.00  9.92           C
ATOM   1310  C    LEU A 169      63.142  46.991   8.199  1.00  9.72           C
ATOM   1311  O    LEU A 169      63.971  46.249   8.806  1.00 10.04           O
ATOM   1312  CB   LEU A 169      60.813  47.079   9.151  1.00 11.30           C
ATOM   1313  CG   LEU A 169      59.293  46.687   9.101  1.00 11.70           C
ATOM   1314  CD1  LEU A 169      58.578  47.410  10.210  1.00 14.19           C
ATOM   1315  CD2  LEU A 169      58.688  47.077   7.787  1.00 12.13           C
ATOM   1316  N    PRO A 170      63.430  48.172   7.745  1.00  9.14           N
ATOM   1317  CA   PRO A 170      64.754  48.771   7.988  1.00 10.04           C
ATOM   1318  C    PRO A 170      64.960  48.963   9.445  1.00  9.71           C
ATOM   1319  O    PRO A 170      64.016  49.198  10.258  1.00 10.63           O
ATOM   1320  CB   PRO A 170      64.699  50.062   7.202  1.00 10.89           C
ATOM   1321  CG   PRO A 170      63.530  49.957   6.271  1.00 11.93           C
ATOM   1322  CD   PRO A 170      62.545  49.071   6.946  1.00 10.87           C
ATOM   1323  N    ASN A 171      66.228  48.999   9.806  1.00  9.70           N
ATOM   1324  CA   ASN A 171      66.669  49.204  11.197  1.00 10.74           C
```

Figure 6Z

| | | | | | | | | | | |
|---|---|---|---|---|---|---|---|---|---|---|
| ATOM | 1325 | C | ASN | A | 171 | 66.103 | 50.420 | 11.847 | 1.00 10.33 | C |
| ATOM | 1326 | O | ASN | A | 171 | 66.118 | 51.533 | 11.337 | 1.00 12.60 | O |
| ATOM | 1327 | CB | ASN | A | 171 | 68.227 | 49.284 | 11.178 | 1.00 11.62 | C |
| ATOM | 1328 | CG | ASN | A | 171 | 68.890 | 49.260 | 12.525 | 1.00 11.64 | C |
| ATOM | 1329 | OD1 | ASN | A | 171 | 68.348 | 48.691 | 13.479 | 1.00 13.55 | O |
| ATOM | 1330 | ND2 | ASN | A | 171 | 70.004 | 49.926 | 12.624 | 1.00 10.94 | N |
| ATOM | 1331 | N | GLY | A | 172 | 65.528 | 50.210 | 13.065 | 1.00 11.34 | N |
| ATOM | 1332 | CA | GLY | A | 172 | 65.016 | 51.262 | 13.880 | 1.00 11.48 | C |
| ATOM | 1333 | C | GLY | A | 172 | 63.554 | 51.419 | 13.853 | 1.00 10.15 | C |
| ATOM | 1334 | O | GLY | A | 172 | 62.960 | 51.958 | 14.802 | 1.00 12.67 | O |
| ATOM | 1335 | N | TRP | A | 173 | 62.887 | 51.061 | 12.746 | 1.00 10.63 | N |
| ATOM | 1336 | CA | TRP | A | 173 | 61.461 | 51.236 | 12.661 | 1.00 10.59 | C |
| ATOM | 1337 | C | TRP | A | 173 | 60.768 | 49.998 | 13.232 | 1.00 11.55 | C |
| ATOM | 1338 | O | TRP | A | 173 | 60.910 | 48.979 | 12.720 | 1.00 14.79 | O |
| ATOM | 1339 | CB | TRP | A | 173 | 60.983 | 51.522 | 11.247 | 1.00 9.71 | C |
| ATOM | 1340 | CG | TRP | A | 173 | 61.137 | 52.904 | 10.763 | 1.00 9.75 | C |
| ATOM | 1341 | CD1 | TRP | A | 173 | 60.311 | 53.978 | 11.033 | 1.00 9.20 | C |
| ATOM | 1342 | CD2 | TRP | A | 173 | 62.119 | 53.413 | 9.862 | 1.00 10.01 | C |
| ATOM | 1343 | NE1 | TRP | A | 173 | 60.688 | 55.081 | 10.372 | 1.00 9.35 | N |
| ATOM | 1344 | CE2 | TRP | A | 173 | 61.789 | 54.777 | 9.627 | 1.00 9.12 | C |
| ATOM | 1345 | CE3 | TRP | A | 173 | 63.225 | 52.869 | 9.215 | 1.00 10.16 | C |
| ATOM | 1346 | CZ2 | TRP | A | 173 | 62.522 | 55.550 | 8.723 | 1.00 10.17 | C |
| ATOM | 1347 | CZ3 | TRP | A | 173 | 63.928 | 53.652 | 8.339 | 1.00 10.89 | C |
| ATOM | 1348 | CH2 | TRP | A | 173 | 63.577 | 54.973 | 8.102 | 1.00 10.55 | C |
| ATOM | 1349 | N | GLY | A | 174 | 59.988 | 50.201 | 14.299 | 1.00 12.50 | N |
| ATOM | 1350 | CA | GLY | A | 174 | 59.205 | 49.082 | 14.913 | 1.00 14.09 | C |
| ATOM | 1351 | C | GLY | A | 174 | 57.992 | 48.728 | 14.034 | 1.00 12.53 | C |
| ATOM | 1352 | O | GLY | A | 174 | 57.648 | 47.578 | 14.031 | 1.00 13.52 | O |
| ATOM | 1353 | N | PHE | A | 175 | 57.451 | 49.701 | 13.256 | 1.00 11.87 | N |
| ATOM | 1354 | CA | PHE | A | 175 | 56.250 | 49.480 | 12.455 | 1.00 10.90 | C |
| ATOM | 1355 | C | PHE | A | 175 | 56.347 | 50.310 | 11.196 | 1.00 9.24 | C |
| ATOM | 1356 | O | PHE | A | 175 | 56.949 | 51.389 | 11.235 | 1.00 11.32 | O |
| ATOM | 1357 | CB | PHE | A | 175 | 54.986 | 49.969 | 13.228 | 1.00 13.68 | C |
| ATOM | 1358 | CG | PHE | A | 175 | 54.850 | 49.467 | 14.592 | 1.00 17.07 | C |
| ATOM | 1359 | CD1 | PHE | A | 175 | 54.292 | 48.286 | 14.791 | 1.00 19.93 | C |
| ATOM | 1360 | CD2 | PHE | A | 175 | 55.370 | 50.184 | 15.635 | 1.00 18.63 | C |
| ATOM | 1361 | CE1 | PHE | A | 175 | 54.204 | 47.742 | 16.106 | 1.00 21.75 | C |
| ATOM | 1362 | CE2 | PHE | A | 175 | 55.278 | 49.711 | 16.964 | 1.00 23.00 | C |
| ATOM | 1363 | CZ | PHE | A | 175 | 54.701 | 48.481 | 17.191 | 1.00 22.98 | C |
| ATOM | 1364 | N | TYR | A | 176 | 55.688 | 49.899 | 10.126 | 1.00 9.12 | N |
| ATOM | 1365 | CA | TYR | A | 176 | 55.482 | 50.778 | 8.946 | 1.00 8.30 | C |
| ATOM | 1366 | C | TYR | A | 176 | 54.295 | 51.699 | 9.302 | 1.00 7.30 | C |
| ATOM | 1367 | O | TYR | A | 176 | 53.379 | 51.370 | 10.081 | 1.00 8.52 | O |
| ATOM | 1368 | CB | TYR | A | 176 | 55.285 | 50.039 | 7.644 | 1.00 9.38 | C |
| ATOM | 1369 | CG | TYR | A | 176 | 54.009 | 49.216 | 7.537 | 1.00 10.20 | C |
| ATOM | 1370 | CD1 | TYR | A | 176 | 52.830 | 49.779 | 7.177 | 1.00 10.70 | C |
| ATOM | 1371 | CD2 | TYR | A | 176 | 54.037 | 47.860 | 7.757 | 1.00 13.14 | C |
| ATOM | 1372 | CE1 | TYR | A | 176 | 51.654 | 49.040 | 7.067 | 1.00 12.14 | C |
| ATOM | 1373 | CE2 | TYR | A | 176 | 52.856 | 47.122 | 7.666 | 1.00 16.11 | C |
| ATOM | 1374 | CZ | TYR | A | 176 | 51.726 | 47.753 | 7.315 | 1.00 14.00 | C |
| ATOM | 1375 | OH | TYR | A | 176 | 50.589 | 46.919 | 7.222 | 1.00 20.16 | O |
| ATOM | 1376 | N | THR | A | 177 | 54.291 | 52.874 | 8.692 | 1.00 7.60 | N |
| ATOM | 1377 | CA | THR | A | 177 | 53.117 | 53.789 | 8.650 | 1.00 7.06 | C |

Figure 6AA

```
ATOM   1378  C    THR A 177      52.300  53.504   7.395  1.00   7.51           C
ATOM   1379  O    THR A 177      51.054  53.421   7.465  1.00   7.70           O
ATOM   1380  CB   THR A 177      53.544  55.243   8.784  1.00   7.48           C
ATOM   1381  OG1  THR A 177      54.183  55.407  10.075  1.00   9.04           O
ATOM   1382  CG2  THR A 177      52.402  56.179   8.710  1.00   8.24           C
ATOM   1383  N    PHE A 178      52.953  53.436   6.217  1.00   6.45           N
ATOM   1384  CA   PHE A 178      52.341  53.017   4.988  1.00   6.80           C
ATOM   1385  C    PHE A 178      53.070  51.855   4.408  1.00   7.00           C
ATOM   1386  O    PHE A 178      54.297  51.738   4.555  1.00   6.88           O
ATOM   1387  CB   PHE A 178      52.309  54.159   3.916  1.00   7.21           C
ATOM   1388  CG   PHE A 178      51.620  55.432   4.359  1.00   7.27           C
ATOM   1389  CD1  PHE A 178      50.256  55.546   4.204  1.00   7.79           C
ATOM   1390  CD2  PHE A 178      52.316  56.510   4.854  1.00   8.41           C
ATOM   1391  CE1  PHE A 178      49.631  56.753   4.599  1.00   8.66           C
ATOM   1392  CE2  PHE A 178      51.649  57.683   5.184  1.00   8.92           C
ATOM   1393  CZ   PHE A 178      50.353  57.793   5.073  1.00   8.63           C
ATOM   1394  N    TRP A 179      52.365  50.935   3.688  1.00   6.17           N
ATOM   1395  CA   TRP A 179      52.929  49.816   2.980  1.00   6.36           C
ATOM   1396  C    TRP A 179      52.382  49.808   1.568  1.00   6.69           C
ATOM   1397  O    TRP A 179      51.165  49.697   1.329  1.00   6.44           O
ATOM   1398  CB   TRP A 179      52.566  48.503   3.661  1.00   6.82           C
ATOM   1399  CG   TRP A 179      52.955  47.232   2.949  1.00   6.55           C
ATOM   1400  CD1  TRP A 179      53.937  47.069   2.040  1.00   6.41           C
ATOM   1401  CD2  TRP A 179      52.317  45.975   3.109  1.00   8.05           C
ATOM   1402  NE1  TRP A 179      53.942  45.743   1.585  1.00   7.23           N
ATOM   1403  CE2  TRP A 179      52.928  45.079   2.198  1.00   7.26           C
ATOM   1404  CE3  TRP A 179      51.235  45.533   3.881  1.00   8.81           C
ATOM   1405  CZ2  TRP A 179      52.558  43.732   2.085  1.00   8.97           C
ATOM   1406  CZ3  TRP A 179      50.838  44.177   3.703  1.00   9.56           C
ATOM   1407  CH2  TRP A 179      51.482  43.322   2.817  1.00   9.98           C
ATOM   1408  N    GLN A 180      53.278  50.006   0.584  1.00   6.00           N
ATOM   1409  CA   GLN A 180      52.971  49.854  -0.845  1.00   6.10           C
ATOM   1410  C    GLN A 180      53.133  48.402  -1.210  1.00   6.73           C
ATOM   1411  O    GLN A 180      54.222  47.834  -1.234  1.00   6.86           O
ATOM   1412  CB   GLN A 180      53.929  50.716  -1.687  1.00   6.67           C
ATOM   1413  CG   GLN A 180      53.363  50.921  -3.123  1.00   7.13           C
ATOM   1414  CD   GLN A 180      54.416  51.718  -3.949  1.00   7.63           C
ATOM   1415  OE1  GLN A 180      54.211  52.939  -4.165  1.00  10.06           O
ATOM   1416  NE2  GLN A 180      55.494  51.140  -4.249  1.00   6.69           N
ATOM   1417  N    TYR A 181      51.975  47.712  -1.473  1.00   6.71           N
ATOM   1418  CA   TYR A 181      51.921  46.249  -1.616  1.00   7.80           C
ATOM   1419  C    TYR A 181      51.712  45.817  -3.030  1.00   7.74           C
ATOM   1420  O    TYR A 181      51.853  44.599  -3.273  1.00   8.31           O
ATOM   1421  CB   TYR A 181      50.911  45.655  -0.610  1.00   8.76           C
ATOM   1422  CG   TYR A 181      49.480  46.025  -0.854  1.00   9.45           C
ATOM   1423  CD1  TYR A 181      48.943  47.142  -0.310  1.00   9.52           C
ATOM   1424  CD2  TYR A 181      48.620  45.199  -1.584  1.00  10.91           C
ATOM   1425  CE1  TYR A 181      47.614  47.549  -0.474  1.00  10.25           C
ATOM   1426  CE2  TYR A 181      47.289  45.564  -1.776  1.00  12.17           C
ATOM   1427  CZ   TYR A 181      46.804  46.698  -1.221  1.00  12.20           C
ATOM   1428  OH   TYR A 181      45.452  47.072  -1.389  1.00  14.26           O
ATOM   1429  N    ASN A 182      51.408  46.689  -3.981  1.00   7.33           N
ATOM   1430  CA   ASN A 182      51.450  46.382  -5.408  1.00   7.90           C
```

Figure 6AB

```
ATOM   1431  C    ASN A 182      51.615  47.632  -6.190  1.00   7.49           C
ATOM   1432  O    ASN A 182      51.474  48.772  -5.673  1.00   7.74           O
ATOM   1433  CB   ASN A 182      50.249  45.509  -5.851  1.00   8.26           C
ATOM   1434  CG   ASN A 182      48.934  46.233  -5.948  1.00   7.94           C
ATOM   1435  OD1  ASN A 182      48.824  47.393  -6.384  1.00   8.24           O
ATOM   1436  ND2  ASN A 182      47.899  45.520  -5.540  1.00  11.05           N
ATOM   1437  N    ASP A 183      51.949  47.462  -7.481  1.00   8.23           N
ATOM   1438  CA   ASP A 183      52.020  48.523  -8.433  1.00   8.47           C
ATOM   1439  C    ASP A 183      50.913  48.441  -9.453  1.00   8.65           C
ATOM   1440  O    ASP A 183      51.068  48.810 -10.636  1.00  10.80           O
ATOM   1441  CB   ASP A 183      53.396  48.535  -9.178  1.00  10.41           C
ATOM   1442  CG   ASP A 183      53.727  47.244  -9.899  1.00  13.30           C
ATOM   1443  OD1  ASP A 183      52.995  46.317  -9.884  1.00  14.47           O
ATOM   1444  OD2  ASP A 183      54.877  47.310 -10.471  1.00  17.15           O
ATOM   1445  N    LYS A 184      49.744  47.981  -9.021  1.00   9.23           N
ATOM   1446  CA   LYS A 184      48.592  47.699  -9.880  1.00   9.58           C
ATOM   1447  C    LYS A 184      47.300  48.201  -9.315  1.00   9.73           C
ATOM   1448  O    LYS A 184      46.306  47.476  -9.234  1.00  11.04           O
ATOM   1449  CB   LYS A 184      48.485  46.223 -10.210  1.00  13.16           C
ATOM   1450  CG   LYS A 184      49.740  45.580 -10.781  1.00  19.34           C
ATOM   1451  CD   LYS A 184      49.664  44.027 -10.706  1.00  28.70           C
ATOM   1452  CE   LYS A 184      48.509  43.440 -11.542  1.00  41.22           C
ATOM   1453  NZ   LYS A 184      48.302  41.938 -11.590  1.00  45.49           N
ATOM   1454  N    TYR A 185      47.257  49.419  -8.827  1.00   9.07           N
ATOM   1455  CA   TYR A 185      46.011  50.018  -8.446  1.00   9.69           C
ATOM   1456  C    TYR A 185      45.069  49.926  -9.675  1.00   9.31           C
ATOM   1457  O    TYR A 185      45.508  50.233 -10.806  1.00  10.58           O
ATOM   1458  CB   TYR A 185      46.230  51.498  -8.038  1.00  10.36           C
ATOM   1459  CG   TYR A 185      44.956  52.124  -7.529  1.00   9.99           C
ATOM   1460  CD1  TYR A 185      44.398  51.737  -6.346  1.00  10.62           C
ATOM   1461  CD2  TYR A 185      44.250  53.084  -8.256  1.00  10.54           C
ATOM   1462  CE1  TYR A 185      43.209  52.270  -5.856  1.00  12.78           C
ATOM   1463  CE2  TYR A 185      43.060  53.619  -7.811  1.00  12.38           C
ATOM   1464  CZ   TYR A 185      42.527  53.202  -6.650  1.00  12.47           C
ATOM   1465  OH   TYR A 185      41.327  53.806  -6.187  1.00  13.72           O
ATOM   1466  N    PRO A 186      43.752  49.611  -9.495  1.00  11.49           N
ATOM   1467  CA   PRO A 186      42.920  49.334 -10.684  1.00  14.07           C
ATOM   1468  C    PRO A 186      42.821  50.448 -11.726  1.00  13.26           C
ATOM   1469  O    PRO A 186      42.700  50.165 -12.914  1.00  15.98           O
ATOM   1470  CB   PRO A 186      41.536  48.995 -10.085  1.00  17.71           C
ATOM   1471  CG   PRO A 186      41.843  48.528  -8.724  1.00  19.79           C
ATOM   1472  CD   PRO A 186      43.075  49.272  -8.236  1.00  13.91           C
ATOM   1473  N    GLN A 187      42.805  51.701 -11.335  1.00  11.15           N
ATOM   1474  CA   GLN A 187      42.775  52.850 -12.234  1.00  11.00           C
ATOM   1475  C    GLN A 187      44.118  53.269 -12.736  1.00  10.32           C
ATOM   1476  O    GLN A 187      44.231  54.297 -13.469  1.00  10.71           O
ATOM   1477  CB   GLN A 187      42.069  54.045 -11.593  1.00  10.60           C
ATOM   1478  CG   GLN A 187      40.650  53.829 -11.195  1.00  12.08           C
ATOM   1479  CD   GLN A 187      39.927  55.099 -10.953  1.00  11.42           C
ATOM   1480  OE1  GLN A 187      40.005  56.003 -11.795  1.00  12.87           O
ATOM   1481  NE2  GLN A 187      39.212  55.203  -9.839  1.00  11.74           N
ATOM   1482  N    GLY A 188      45.184  52.643 -12.284  1.00   9.98           N
ATOM   1483  CA   GLY A 188      46.535  53.041 -12.565  1.00  10.05           C
```

Figure 6AC

```
ATOM   1484  C    GLY A 188      47.208  53.598 -11.311  1.00  9.45           C
ATOM   1485  O    GLY A 188      46.582  54.334 -10.565  1.00  9.93           O
ATOM   1486  N    GLY A 189      48.451  53.243 -11.087  1.00  8.73           N
ATOM   1487  CA   GLY A 189      49.240  53.656  -9.907  1.00  8.57           C
ATOM   1488  C    GLY A 189      49.484  52.471  -8.973  1.00  7.37           C
ATOM   1489  O    GLY A 189      49.376  51.291  -9.375  1.00  8.36           O
ATOM   1490  N    ASP A 190      49.900  52.788  -7.757  1.00  8.00           N
ATOM   1491  CA   ASP A 190      50.283  51.749  -6.763  1.00  7.41           C
ATOM   1492  C    ASP A 190      49.331  51.716  -5.614  1.00  6.96           C
ATOM   1493  O    ASP A 190      48.703  52.764  -5.333  1.00  8.20           O
ATOM   1494  CB   ASP A 190      51.712  52.080  -6.230  1.00  8.03           C
ATOM   1495  CG   ASP A 190      52.688  52.329  -7.321  1.00  9.94           C
ATOM   1496  OD1  ASP A 190      52.871  51.537  -8.212  1.00 12.53           O
ATOM   1497  OD2  ASP A 190      53.313  53.508  -7.331  1.00 12.54           O
ATOM   1498  N    SER A 191      49.182  50.576  -4.980  1.00  6.60           N
ATOM   1499  CA   SER A 191      48.241  50.389  -3.887  1.00  7.29           C
ATOM   1500  C    SER A 191      48.954  50.423  -2.539  1.00  6.67           C
ATOM   1501  O    SER A 191      50.008  49.786  -2.375  1.00  6.82           O
ATOM   1502  CB   SER A 191      47.512  49.068  -4.024  1.00  7.69           C
ATOM   1503  OG   SER A 191      46.860  48.949  -5.284  1.00  8.91           O
ATOM   1504  N    ASN A 192      48.354  51.091  -1.558  1.00  6.40           N
ATOM   1505  CA   ASN A 192      48.928  51.245  -0.196  1.00  6.69           C
ATOM   1506  C    ASN A 192      47.937  50.892   0.867  1.00  6.96           C
ATOM   1507  O    ASN A 192      46.704  51.118   0.778  1.00  7.83           O
ATOM   1508  CB   ASN A 192      49.358  52.697   0.027  1.00  7.65           C
ATOM   1509  CG   ASN A 192      50.411  53.131  -0.928  1.00  6.92           C
ATOM   1510  OD1  ASN A 192      51.522  52.656  -0.955  1.00  7.75           O
ATOM   1511  ND2  ASN A 192      50.061  54.143  -1.767  1.00  9.80           N
ATOM   1512  N    TRP A 193      48.461  50.456   2.004  1.00  7.35           N
ATOM   1513  CA   TRP A 193      47.767  50.442   3.306  1.00  7.07           C
ATOM   1514  C    TRP A 193      48.357  51.501   4.230  1.00  7.17           C
ATOM   1515  O    TRP A 193      49.601  51.621   4.316  1.00  8.16           O
ATOM   1516  CB   TRP A 193      47.930  49.079   3.978  1.00  7.75           C
ATOM   1517  CG   TRP A 193      47.214  47.971   3.389  1.00  9.37           C
ATOM   1518  CD1  TRP A 193      47.761  46.821   2.865  1.00 12.13           C
ATOM   1519  CD2  TRP A 193      45.814  47.890   3.244  1.00 10.95           C
ATOM   1520  NE1  TRP A 193      46.763  46.027   2.376  1.00 14.80           N
ATOM   1521  CE2  TRP A 193      45.562  46.624   2.574  1.00 12.79           C
ATOM   1522  CE3  TRP A 193      44.756  48.667   3.686  1.00 11.10           C
ATOM   1523  CZ2  TRP A 193      44.241  46.183   2.352  1.00 18.46           C
ATOM   1524  CZ3  TRP A 193      43.421  48.233   3.405  1.00 13.88           C
ATOM   1525  CH2  TRP A 193      43.234  47.004   2.711  1.00 15.40           C
ATOM   1526  N    PHE A 194      47.507  52.182   4.982  1.00  6.79           N
ATOM   1527  CA   PHE A 194      47.885  52.941   6.167  1.00  7.26           C
ATOM   1528  C    PHE A 194      47.675  52.069   7.375  1.00  7.54           C
ATOM   1529  O    PHE A 194      46.563  51.501   7.572  1.00  8.32           O
ATOM   1530  CB   PHE A 194      47.056  54.228   6.281  1.00  8.09           C
ATOM   1531  CG   PHE A 194      47.231  54.909   7.610  1.00  7.24           C
ATOM   1532  CD1  PHE A 194      48.371  55.592   7.884  1.00  8.02           C
ATOM   1533  CD2  PHE A 194      46.229  54.837   8.566  1.00  7.43           C
ATOM   1534  CE1  PHE A 194      48.558  56.220   9.127  1.00  8.63           C
ATOM   1535  CE2  PHE A 194      46.395  55.471   9.805  1.00  8.66           C
ATOM   1536  CZ   PHE A 194      47.543  56.145  10.082  1.00  8.42           C
```

Figure 6AD

```
ATOM   1537  N    ASN A 195      48.686  51.998   8.231  1.00   7.88           N
ATOM   1538  CA   ASN A 195      48.669  51.100   9.391  1.00   9.52           C
ATOM   1539  C    ASN A 195      47.984  51.743  10.587  1.00   9.29           C
ATOM   1540  O    ASN A 195      48.627  52.172  11.556  1.00  12.58           O
ATOM   1541  CB   ASN A 195      50.142  50.789   9.746  1.00  10.38           C
ATOM   1542  CG   ASN A 195      50.285  49.580  10.614  1.00  11.58           C
ATOM   1543  OD1  ASN A 195      49.281  48.941  11.061  1.00  14.71           O
ATOM   1544  ND2  ASN A 195      51.518  49.238  10.933  1.00  12.69           N
ATOM   1545  N    GLY A 196      46.682  51.848  10.527  1.00   9.81           N
ATOM   1546  CA   GLY A 196      45.872  52.399  11.610  1.00   9.60           C
ATOM   1547  C    GLY A 196      44.515  52.734  11.105  1.00  10.19           C
ATOM   1548  O    GLY A 196      44.157  52.567   9.909  1.00  10.19           O
ATOM   1549  N    ASP A 197      43.647  53.154  12.055  1.00  10.60           N
ATOM   1550  CA   ASP A 197      42.248  53.498  11.691  1.00  10.54           C
ATOM   1551  C    ASP A 197      42.147  54.956  11.176  1.00  11.06           C
ATOM   1552  O    ASP A 197      43.133  55.712  11.091  1.00  10.63           O
ATOM   1553  CB   ASP A 197      41.306  53.247  12.926  1.00  11.49           C
ATOM   1554  CG   ASP A 197      41.575  54.081  14.083  1.00  14.06           C
ATOM   1555  OD1  ASP A 197      42.169  55.149  14.080  1.00  14.18           O
ATOM   1556  OD2  ASP A 197      41.116  53.622  15.239  1.00  16.55           O
ATOM   1557  N    ALA A 198      40.912  55.387  10.807  1.00  10.79           N
ATOM   1558  CA   ALA A 198      40.708  56.675  10.245  1.00  11.15           C
ATOM   1559  C    ALA A 198      41.171  57.821  11.121  1.00  10.52           C
ATOM   1560  O    ALA A 198      41.656  58.887  10.694  1.00  11.59           O
ATOM   1561  CB   ALA A 198      39.246  56.848   9.814  1.00  12.22           C
ATOM   1562  N    SER A 199      40.920  57.678  12.449  1.00  11.04           N
ATOM   1563  CA   SER A 199      41.335  58.645  13.407  1.00  11.12           C
ATOM   1564  C    SER A 199      42.852  58.840  13.444  1.00  10.69           C
ATOM   1565  O    SER A 199      43.352  59.923  13.569  1.00  10.29           O
ATOM   1566  CB   SER A 199      40.714  58.332  14.767  1.00  12.41           C
ATOM   1567  OG   SER A 199      41.162  59.194  15.740  1.00  14.69           O
ATOM   1568  N    ARG A 200      43.561  57.730  13.392  1.00  10.83           N
ATOM   1569  CA   ARG A 200      45.044  57.793  13.371  1.00  11.14           C
ATOM   1570  C    ARG A 200      45.558  58.453  12.047  1.00   9.88           C
ATOM   1571  O    ARG A 200      46.533  59.158  12.060  1.00   9.99           O
ATOM   1572  CB   ARG A 200      45.703  56.410  13.575  1.00  12.14           C
ATOM   1573  CG   ARG A 200      47.199  56.364  13.824  1.00  26.57           C
ATOM   1574  CD   ARG A 200      47.908  54.989  13.821  1.00  36.82           C
ATOM   1575  NE   ARG A 200      47.298  53.997  14.731  1.00  49.33           N
ATOM   1576  CZ   ARG A 200      47.678  52.715  14.871  1.00  48.20           C
ATOM   1577  NH1  ARG A 200      48.699  52.200  14.186  1.00  52.47           N
ATOM   1578  NH2  ARG A 200      47.030  51.944  15.723  1.00  43.45           N
ATOM   1579  N    LEU A 201      44.842  58.222  10.939  1.00   8.93           N
ATOM   1580  CA   LEU A 201      45.222  58.878   9.673  1.00   8.97           C
ATOM   1581  C    LEU A 201      45.018  60.381   9.751  1.00   9.31           C
ATOM   1582  O    LEU A 201      45.889  61.191   9.374  1.00  10.10           O
ATOM   1583  CB   LEU A 201      44.431  58.260   8.530  1.00   9.95           C
ATOM   1584  CG   LEU A 201      44.761  58.849   7.150  1.00   9.95           C
ATOM   1585  CD1  LEU A 201      46.239  58.619   6.786  1.00  10.73           C
ATOM   1586  CD2  LEU A 201      43.885  58.204   6.132  1.00  11.41           C
ATOM   1587  N    ARG A 202      43.891  60.823  10.368  1.00  10.01           N
ATOM   1588  CA   ARG A 202      43.675  62.248  10.588  1.00  10.87           C
ATOM   1589  C    ARG A 202      44.732  62.779  11.521  1.00  10.44           C
```

Figure 6AE

```
ATOM   1590  O    ARG A 202    45.225  63.919  11.350  1.00 11.02    O
ATOM   1591  CB   ARG A 202    42.287  62.561  11.132  1.00 12.31    C
ATOM   1592  CG   ARG A 202    41.210  62.401  10.130  1.00 12.95    C
ATOM   1593  CD   ARG A 202    39.812  62.815  10.642  1.00 12.62    C
ATOM   1594  NE   ARG A 202    39.296  61.984  11.725  1.00 13.10    N
ATOM   1595  CZ   ARG A 202    38.573  60.909  11.559  1.00 12.94    C
ATOM   1596  NH1  ARG A 202    38.260  60.461  10.346  1.00 15.56    N
ATOM   1597  NH2  ARG A 202    38.135  60.254  12.642  1.00 14.72    N
ATOM   1598  N    ALA A 203    45.146  62.068  12.547  1.00 10.66    N
ATOM   1599  CA   ALA A 203    46.176  62.492  13.457  1.00 11.61    C
ATOM   1600  C    ALA A 203    47.520  62.751  12.723  1.00 10.39    C
ATOM   1601  O    ALA A 203    48.260  63.667  13.017  1.00 12.24    O
ATOM   1602  CB   ALA A 203    46.406  61.538  14.653  1.00 12.32    C
ATOM   1603  N    LEU A 204    47.851  61.873  11.776  1.00 10.20    N
ATOM   1604  CA   LEU A 204    49.062  62.058  10.967  1.00  9.80    C
ATOM   1605  C    LEU A 204    48.978  63.313  10.128  1.00  9.40    C
ATOM   1606  O    LEU A 204    49.929  64.100   9.995  1.00 10.59    O
ATOM   1607  CB   LEU A 204    49.292  60.770  10.110  1.00  9.49    C
ATOM   1608  CG   LEU A 204    50.559  60.891   9.214  1.00 10.94    C
ATOM   1609  CD1  LEU A 204    51.823  60.990  10.047  1.00 11.83    C
ATOM   1610  CD2  LEU A 204    50.639  59.662   8.324  1.00 11.42    C
ATOM   1611  N    ALA A 205    47.841  63.542   9.493  1.00  9.80    N
ATOM   1612  CA   ALA A 205    47.642  64.760   8.704  1.00 10.22    C
ATOM   1613  C    ALA A 205    47.745  66.046   9.548  1.00 10.88    C
ATOM   1614  O    ALA A 205    48.361  67.019   9.176  1.00 11.53    O
ATOM   1615  CB   ALA A 205    46.291  64.744   8.012  1.00 10.87    C
ATOM   1616  N    ASN A 206    47.226  65.967  10.769  1.00 11.39    N
ATOM   1617  CA   ASN A 206    47.225  67.136  11.703  1.00 12.74    C
ATOM   1618  C    ASN A 206    48.565  67.403  12.303  1.00 12.44    C
ATOM   1619  O    ASN A 206    48.908  68.572  12.573  1.00 14.36    O
ATOM   1620  CB   ASN A 206    46.185  66.901  12.831  1.00 13.57    C
ATOM   1621  CG   ASN A 206    44.749  66.946  12.355  1.00 14.72    C
ATOM   1622  OD1  ASN A 206    44.436  67.598  11.389  1.00 18.79    O
ATOM   1623  ND2  ASN A 206    43.859  66.396  13.149  1.00 17.10    N
ATOM   1624  N    GLY A 207    49.302  66.373  12.631  1.00 13.63    N
ATOM   1625  CA   GLY A 207    50.447  66.543  13.501  1.00 15.43    C
ATOM   1626  C    GLY A 207    50.099  66.928  14.948  1.00 18.08    C
ATOM   1627  O'   GLY A 207    48.920  66.875  15.319  1.00 19.04    O
ATOM   1628  O''  GLY A 207    50.815  67.305  15.875  0.00 18.08    O
TER
```

POLYPEPTIDES HAVING LYSOZYME ACTIVITY AND POLYNUCLEOTIDES ENCODING SAME

CROSS-REFERENCE TO RELATED APPLICATIONS

This application is a divisional of U.S. application Ser. No. 15/606,031 filed on May 26, 2017, now U.S. Pat. No. 10,119,130, which is a divisional of U.S. application Ser. No. 14/360,529 filed on May 23, 2014, now U.S. Pat. No. 9,701,952, which is a 35 U.S.C. 371 national application of international application no. PCT/DK2012/073483 filed Nov. 23, 2012, which claims priority or the benefit under 35 U.S.C. 119 of European application no. 11190690.5 filed Nov. 25, 2011 and U.S. provisional application No. 61/564,372 filed Nov. 29, 2011. The content of each application is fully incorporated herein by reference.

REFERENCE TO A SEQUENCE LISTING

This application contains a Sequence Listing in computer readable form, which is incorporated herein by reference.

REFERENCE TO ATOMIC COORDINATES

This application sets forth in FIG. 6, the atomic coordinates of the three-dimensional structure of the *Acremonium alkalophilum* CBS114.92 lysozyme.

BACKGROUND OF THE INVENTION

Field of the Invention

The present invention relates to polypeptides having lysozyme activity, catalytic domains, and polynucleotides encoding the polypeptides and catalytic domains. The invention also relates to nucleic acid constructs, vectors, and host cells comprising the polynucleotides as well as methods of producing and using the polypeptides and catalytic domains.

Description of the Related Art

Lysozyme is a O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse resulting from osmotic pressure.

Lysozyme occurs in many organisms such as viruses, plants, insects, birds, reptiles and mammals. In mammals, Lysozyme has been isolated from nasal secretions, saliva, tears, intestines, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide.

There is an increasing interest in the potential of lysozyme enzymes as antimicrobial agents. For example, lysozyme activity has been shown against pathogens such as *Streptococcus pneumoniae, Bacillus anthracis, Enterococcus faecium, Bacillus stearothermophilus, Clostridium botulinum, Clostridium butyricum, Clostridium perfringens, Clostridium sporogenes, Clostridium tyrobutyricum,* and *Listeria monocytogenes.*

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas flagellar* protein (GH73) and *Chalaropsis* lysozymes (GH25). Lysozymes from the families GH23 and GH24 are primarily known from bacteriophages and have not been identified in fungi. The lysozyme family GH25 has been found to be structurally unrelated to the other lysozyme families.

Use of lysozyme has been suggested in animal feed (see for example WO 00/21381 and WO 2004/026334), in cheese production (see for example WO 2005/080559), food preservation (Hughey and Johnson (1987) Appl Environ Microbiol 53:2165), detergents (see for example U.S. Pat. No. 5,041,236 and EP 0425016), in oral care (see for example U.S. Pat. No. 4,355,022, WO 2004/017988 and WO 2008/124764), cosmetology and dermatology, contraception, urology, and gynaecology (see for example WO 2008/124764).

A GH25 lysozyme has been reported from *Chalaropsis* (Felsch et al., 1975, "The N,O-Diacetylmuramidase of *Chalaropsis* species; V The complete amino acid sequence, *J. Biol. Chem.* 250(10):3713-3720).

Hen egg white lysozyme which is the primary product available on the commercial market, does not cleave N,6-O-diacetylmuramidase in, e.g., *Staphylococcus aureus* cell walls and is thus unable to lyse this important human pathogen among others (Masschalck et al., 2002, "Lytic and nonlytic mechanism of inactivation of gram-positive bacteria by lysozyme under atmospheric and high hydrostatic pressure", *J. Food Prot.* 65(12):1916-23).

It has been observed that different lysozymes have different specificities towards different microorganisms. It is therefore desirable to have several lysozymes available in order to be able to select suitable enzymes for each particular application. New polypeptides having lysozyme activity is therefore desired.

SUMMARY OF THE INVENTION

The present invention relates to isolated fungal polypeptides belonging to the GH25 family and having lysozyme activity.

The present invention further relates to isolated polypeptides having lysozyme activity selected from the group consisting of:

(a) a polypeptide having at least 80% sequence identity to the mature polypeptide of SEQ ID NO: 4 or to the mature polypeptide of SEQ ID NO: 8;

(b) a polypeptide encoded by a polynucleotide having at least 80% sequence identity to the mature polypeptide coding sequence of SEQ ID NO: 3 or to the mature polypeptide coding sequence of SEQ ID NO: 7;

(c) a polypeptide encoded by a polynucleotide that hybridizes under medium-high stringency conditions with the mature polypeptide coding sequence of SEQ ID NO: 3 or SEQ ID NO: 7, or the full-length complement thereof;

(d) a variant of the mature polypeptide SEQ ID NO: 4 or SEQ ID NO: 8, comprising a substitution, deletion, and/or insertion at one or more (e.g., several) positions; and (e) a fragment of the polypeptide of (a), (b), (c), or (d) that has lysozyme activity.

The present invention also relates to isolated polynucleotides encoding the polypeptides of the present invention; nucleic acid constructs; recombinant expression vectors;

recombinant host cells comprising the polynucleotides; and methods of producing the polypeptides.

Furthermore, the present invention relates to compositions comprising the polypeptide of the present invention, such as detergent compositions, animal feed compositions and a bacterial genomic DNA extraction composition.

The present invention also relates to the polypeptides of the invention having antimicrobial activity and methods of using the polypeptides of the invention as inhibitors of bio-film formation, in detergents, in dental care, in animal feed and for breaking down the cell walls of bacteria.

The present invention also relates to a polynucleotide encoding a signal peptide comprising or consisting of amino acids 1 to 19 of SEQ ID NO: 4 or amino acids −23 to −1 of SEQ ID NO: 8, which is operably linked to a gene encoding a protein; nucleic acid constructs, expression vectors, and recombinant host cells comprising the polynucleotides; and methods of producing a protein.

Overview of Sequence Listing

SEQ ID NO: 1 is the DNA sequence of the P244A7 GH24 gene as isolated from *Acremonium alkalophilum* CBS114.92.

SEQ ID NO: 2 is the amino acid sequence as deduced from SEQ ID NO: 1.

SEQ ID NO: 3 is the DNA sequence of the P242M9 GH25 gene as isolated from *Acremonium alkalophilum* CBS114.92.

SEQ ID NO: 4 is the amino acid sequence as deduced from SEQ ID NO: 3.

SEQ ID NO: 5 is the forward primer F-P242M9.

SEQ ID NO: 6 is the reverse primer R-P242M9.

SEQ ID NO: 7 is the DNA sequence of the synthetically optimised GH25 gene.

SEQ ID NO: 8 is the amino acid sequence as deduced from SEQ ID NO: 7.

SEQ ID NO: 9 is the forward primer BamHI.

SEQ ID NO: 10 is the reverse primer EcoRI.

BRIEF DESCRIPTION OF THE FIGURES

FIG. 4 shows the lysozyme activity of 4 concentrations of the GH25 lysozyme P242M9 (SEQ ID NO: 4), the synthetic GH25 lysozyme (SEQ ID NO: 8) and 11 variants of SEQ ID NO: 8 as determined by optical density drop of a solution of re-suspended *Clostridium perfringens* NN01260.

FIG. 5 shows the lysozyme activity of 4 concentrations of the GH25 lysozyme P242M9 (SEQ ID NO: 4), the synthetic GH25 lysozyme (SEQ ID NO: 8) and 11 variants of SEQ ID NO: 8 as determined by optical density drop of a solution of re-suspended *Clostridium perfringens* clinical isolate.

FIGS. 6A-6AE set forth the atomic coordinates of the three-dimensional structure of the *Acremonium alkalophilum* CBS114.92 GH25 lysozyme. These atomic coordinates can aid in generating a three dimensional model depicting the structure of the *Acremonium alkalophilum* CBS114.92 GH25 lysozyme and a three dimensional model of homologous structures, such as variants of the aforementioned lysozyme.

Figure 1:
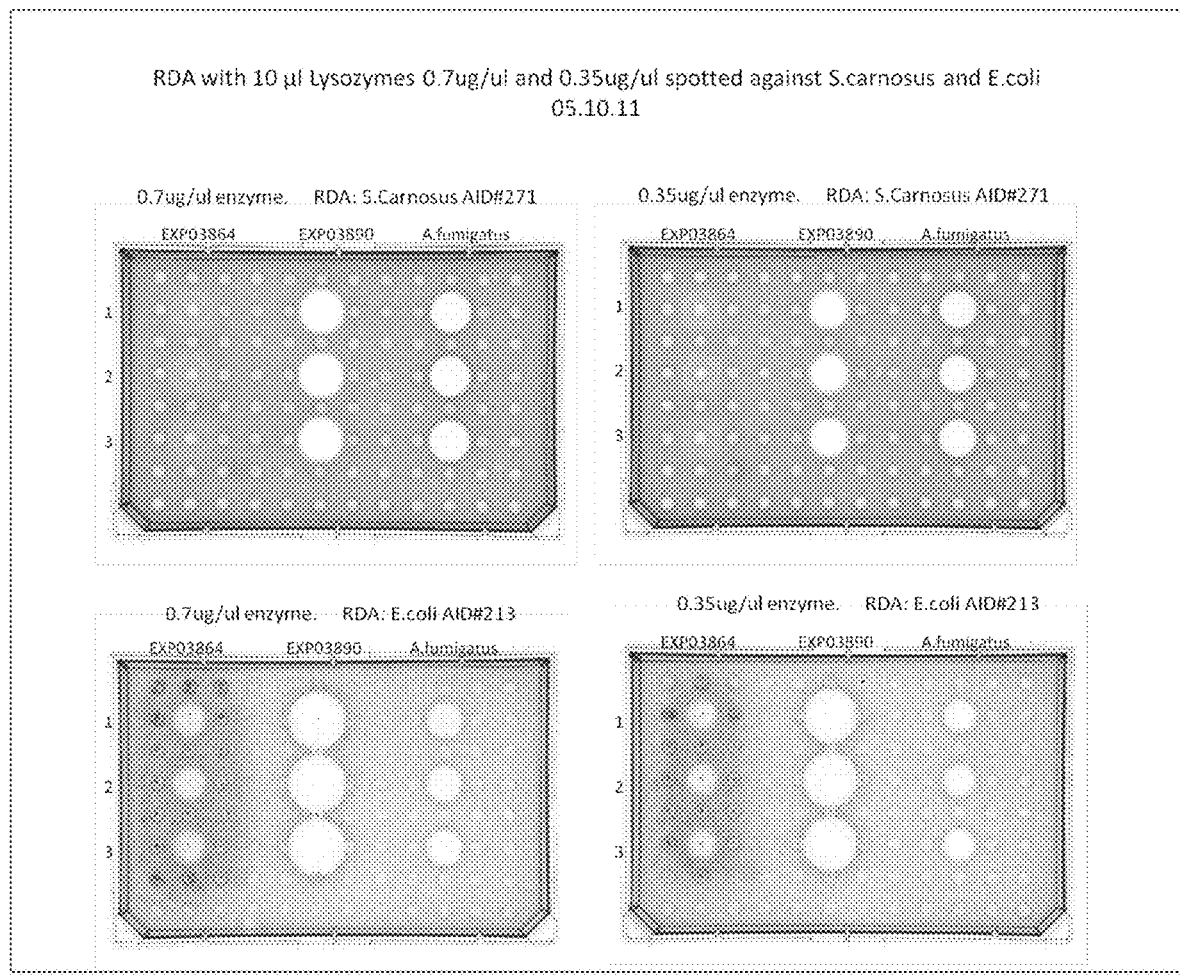
FIG. 1 shows radial diffusion assays of *Acremonium alcalophilum* GH24 lysozyme (EXP03890, SEQ ID NO: 2), *Acremonium alcalophilum* GH25 lysozyme (EXP03864, SEQ ID NO: 4) and a reference lysozyme from *Aspergillus fumigatus* GH25 on *S. carnosus* and *E. coli.*

DEFINITIONS

Lysozyme: The term "lysozyme" activity is defined herein as an O-glycosyl hydrolase, which catalyses the hydrolysis of the glycosidic bond between two or more carbohydrates, or between a carbohydrate and a non-carbohydrate moiety. Lysozymes cleave the glycosidic bond between certain residues in mucopolysaccharides and mucopeptides of bacterial cell walls, such as 1,4-beta-linkages between N-acetylmuramic acid and N-acetyl-D-glucosamine residues in a peptidoglycan and between N-acetyl-D-glucosamine residues in chitodextrins, resulting in bacteriolysis. Lysozyme belongs to the enzyme class EC 3.2.1.17. For purposes of the present invention, lysozyme activity is determined according to the turbidity assay described in example 4. In one aspect, the polypeptides of the present invention have at least 20%, e.g., at least 40%, at least 50%, at least 60%, at least 70%, at least 80%, at least 90%, at least 95%, or at least 100% of the lysozyme activity of the mature polypeptide of one of SEQ ID NO: 4 or SEQ ID NO: 8.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Antimicrobial activity: The term "antimicrobial activity" is defined herein as is an activity that kills or inhibits the growth of microorganisms, such as, algae, archea, bacteria, fungi and/or protozoans. The antimicrobial activity can for example be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect. For purposes of the present invention, antimicrobial activity is determined according to the antimicrobial assay described in example 10.

Altered/modified property: The term "altered/modified property" is defined herein as a characteristic associated with a variant that is altered or modified, as compared relative to the parent lysozyme or an identified reference sequence. The altered or modified property may be a characteristic associated with a variant that is improved, unless otherwise stated, relative to another reference lysozyme or the parent lysozyme. Examples of properties which can be altered/modified or improved are given below.

Thermostability: The term "thermostability" refers to the lysozyme activity after a period of incubation at elevated temperature relative to the parent or an identified reference sequence, either in a buffer or under conditions such as those which exist during product storage/transport or conditions similar to those that exist during industrial use of the variant. A variant may or may not display an altered thermal activity profile relative to the parent. In one aspect, the thermostability of the variant having lysozyme activity is at least 1.0-fold, e.g., at least 1.1-fold, at least 1.5-fold, at least 1.8-fold, at least 2-fold, at least 5-fold, at least 10-fold, at least 15-fold, at least 20-fold, and at least 25-fold more thermostable than the parent or reference sequence at the selected temperature. Preferably the activity is tested using the lysozyme turbidity activity assay described in the "Materials and Methods" section.

Temperature profile/temperature stability: The term "temperature profile/temperature stability" refers to the variant enzyme showing a modified temperature profile as compared to the parent or an identified reference sequence, wherein the temperature profile is determined as lysozyme activity as a function of temperature. The activity at each temperature is preferably indicated as relative activity (in %) normalized to the value at optimum temperature. The optimum temperature is that temperature within the tested temperatures (i.e., those with 5-10° C. jumps) where the activity is highest.

pH stability: The term "pH stability" refers to the variant enzyme displaying structural stability relative to the parent lysozyme or an identified reference sequence, after a period of incubation at a pH which is outside the pH range where the enzyme is active (pH activity range). Such a variant may or may not display an altered pH activity profile relative to the parent. For example, the variant may not be active at the increased or decreased pH, but is able to maintain its three dimensional structure and then regain activity once it is returned to the pH activity range. Alternatively, the variant may have an improved ability to refold relative to the parent following incubation at increased or decreased pH.

In one aspect, the pH stability profile is altered such that a lysozyme variant has improved stability at acidic pH. As used herein, acidic pH means from pH 2 to 5.5, preferably from 2.5 to 5.25, more preferably from 3 to 5, even more preferably from 3.5 to 4. Preferably, the variant lysozyme maintains at least 40%, preferably at least 50%, 60%, 70% or 80%, more preferably at least 90%, even more preferably at least 95% residual activity after incubation at a given pH for 1 hour when compared to the variant which has been maintained at pH 6.5 for the same time. Preferably, the residual activity of the variant lysozyme is at least 1.1-fold, at least 1.3-fold, at least 1.5-fold, preferably at least 2-fold, more preferably at least 5-fold, most preferably at least 7-fold, and even most preferably at least 10-fold higher than the residual activity of the parent lysozyme or an identified reference sequence which has been treated under the same conditions. Preferably, the activity is tested using the lysozyme turbidity activity assay described in the "Materials and Methods" section.

pH activity: The term "pH activity" is defined herein as a variant lysozyme displaying an alteration of the pH-dependent activity profile when compared to the pH activity profile of the parent lysozyme or an identified reference sequence. The pH activity profile provides a measure of the enzyme's efficiency in preventing microbial growth, eliminating microbial cells and/or performing catalysis of a hydrolysis reaction over a pH range at given conditions such as temperature and solvent composition. A lysozyme has a specific pH range wherein the polypeptide is stable and retains its enzymatic activity, outside this range the lysozyme becomes less active and potentially also less stable. Within the pH range there generally is a pH optimum, where the lysozyme shows the highest activity.

A lysozyme variant with improved activity at alkaline pH (e.g., from pH 7.5 to 12, preferably from 8 to 11, more preferably from 8.5 to 10, even more preferably from 9 to 9.5) will be able to function in more alkaline environments such as detergents.

A variant with improved activity at acidic pH (e.g., from pH 2 to 6.5, preferably from 2.5 to 6, more preferably from 3 to 5.5, even more preferably from 3.5 to 5) will be able to function under more acidic conditions, such as preservative in certain foods.

A variant with improved activity at neutral to weakly acidic pH (e.g., from pH 4 to 7.0, preferably from 4.5 to 6.5, more preferably from 5 to 6.5) will be able to function under weakly acidic or neutral conditions, such as for use a eubiotic molecule in feeds, to stabilize the healthy microflora of animals or by suppressing growth/intestinal colonization of viral, parasitic or bacterial pathogens in the GI tracts of animals.

In one aspect, the pH activity profile is altered such that a lysozyme variant has improved activity at a more alkaline pH. Preferably, the activity of the lysozyme variant at a pH at least 0.5 units higher, preferably at least 1.0 pH units higher, more preferably at least 1.5 pH units higher, even more preferably at least 2.0 pH units higher is at least 1.1-fold, preferably at least 1.5-fold, more preferably at least 2-fold, even more preferably at least 5-fold and most preferably at least 10-fold higher than that of the parent enzyme or an identified reference sequence. Preferably, the lysozyme variant at the same time maintains at least 40%, preferably at least 50%, 60%, 70% or 80%, or 90%, more preferably at least 95%, even more preferably at least 100% of the activity that parent lysozyme or an identified reference sequence exhibits at its pH optimum. Preferably, the activity is tested using the lysozyme turbidity activity assay described in the "Materials and Methods" section.

In another aspect, the pH activity profile is altered such that a lysozyme variant has improved activity at a more acidic pH. Preferably, the activity of the lysozyme variant at a pH at least 0.5 units lower, preferably at least 1.0 pH units lower, more preferably at least 1.5 pH units lower, even more preferably at least 2.0 pH units lower is at least 1.1-fold, preferably at least 1.5-fold, more preferably at least 2-fold, even more preferably at least 5-fold and most preferably at least 10-fold higher than that of the parent enzyme or an identified reference sequence. Preferably, the lysozyme variant at the same time maintains at least 40%, preferably at least 50%, 60%, 70% or 80%, or 90%, more preferably at least 95%, even more preferably at least 100% of the activity that parent lysozyme or an identified reference sequence exhibits at its pH optimum. Preferably, the activity is tested using the lysozyme turbidity activity assay described in the "Materials and Methods" section.

Substrate specificity: The term "substrate specificity" refers to the specificity of the lysozyme in regard to the type of bacteria it can kill/inhibit and/or in relation to model lysozyme substrates (e.g., p-NP-(NAG-NAM)n or p-NP-(NAG)m oligomers). By modifying the substrate specificity of the lysozyme, the type of bacteria the lysozyme can kill and/or inhibit can be altered. In one aspect, the substrate specificity of the lysozyme is broadened, thereby allowing other types of bacteria to be killed and/or inhibited apart from the bacteria which the wild type lysozyme can kill and/or inhibit.

Glycation Susceptibility: Non-enzymatic glycation is a spontaneous posttranslational process where reducing sugars bind covalently to free amino groups in proteins primarily at Lysine (K) residues. Glycation may impact the activity of the lysozyme. In accordance with the present invention, the susceptibility of the lysozyme to non-enzymatic glycation may be reduced by specified amino acid changes.

Improved properties may also include thermal properties, such as pelleting stability, steam stability, broader temperature activity profile. Further improved properties may include protease-sensibility, and/or glycosylation pattern. Improvements are preferably assessed in relation to the desired application conditions.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has lysozyme activity. In one aspect, a fragment contains at least 184 amino acid residues (e.g., amino acids 25 to 208 of SEQ ID NO: 4), or at least 195 amino acid residues (e.g., amino acids 22 to 216 of SEQ ID NO: 4). In a further aspect, a fragment contains at least 184 amino acid residues (e.g., amino acids 10 to 193 of SEQ ID NO: 8), or at least 195 amino acid residues (e.g., amino acids 5 to 199 of SEQ ID NO: 8).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 227 of SEQ ID NO: 4 or amino acids 1 to 208 of SEQ ID NO: 8 based on the SignalP program (Nielsen et al., 1997, *Protein Engineering* 10: 1-6) that predicts amino acids 1 to 19 of SEQ ID NO: 4 and amino acids −40 to −18 of SEQ ID NO: 8 are signal peptides. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having lysozyme activity. In one aspect, the mature polypeptide coding sequence is the joined sequence of nucleotides 58 to 147 and nucleotides 302 to 835 of SEQ ID NO: 3, and nucleotides 121 to 744 of SEQ ID NO: 7 based on the SignalP program (Nielsen et al., 1997, supra)] that predicts nucleotides 1 to 57 of SEQ ID NO: 3 and nucleotides 1 to 69 of SEQ ID NO: 7 encode signal peptides.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment).

Stringency conditions: The different strigency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity. In one aspect, a subsequence contains at least 552 nucleotides (e.g., the joint sequence of nucleotides 73 to 147 and nucleotides 302 to 778 of SEQ ID NO: 3), or at least 585 nucleotides (e.g., the joint sequence of nucleotides 64 to 147 and nucleotides 302 to 802 of SEQ ID NO: 3). In a further aspect, a subsequence contains at least 552 nucleotides (e.g., the sequence of nucleotides 148 to 699 of SEQ ID NO: 7), or at least 585 nucleotides (e.g., the sequence of nucleotides 133 to 717 of SEQ ID NO: 7).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position. A variant according to the invention may comprise from 1 to 5; from 1 to 10; from 1 to 15; from 1 to 20; from 1 to 25; from 1 to 30; from 1 to 35; from 1 to 40; from 1 to 45; i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 alterations.

The variants of the present invention have at least one alteration/modification selected from the group consisting of position number 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190 in which the position corresponds to the position in the mature sequence of SEQ ID NO: 8. The variant polypeptide sequence is preferably one which is not found in nature.

Wild-type Lysozyme: The term "wild-type" lysozyme means a lysozyme expressed by a naturally occurring microorganism, such as a bacterium, yeast, or filamentous fungus found in nature.

Conventions for Designation of Variants

For purposes of the present invention, the mature polypeptide disclosed in SEQ ID NO: 8 is used to determine the corresponding amino acid residue in another lysozyme. The amino acid sequence of another lysozyme is aligned with the mature polypeptide disclosed in SEQ ID NO: 8, and based on the alignment, the amino acid position number corresponding to any amino acid residue in the mature polypeptide disclosed in SEQ ID NO: 8 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment−Total Number of Gaps in Alignment). The Needleman-Wunsch algorithm is used for sequence comparisons and for calculating sequence identities.

Identification of the corresponding amino acid residue in another lysozyme can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 8 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent | Variant |
|---|---|
| 195 | 195 195a 195b |
| G | G - K - A |

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg 170Gly", "Tyr167Gly+Arg 170Ala", "Tyr167Ala+Arg 170Gly", and "Tyr167Ala+Arg 170Ala".

DETAILED DESCRIPTION OF THE INVENTION

Polypeptides Having Lysozyme Activity

In an embodiment, the present invention relates to isolated polypeptides having a sequence identity to the mature polypeptide of SEQ ID NO: 4 of at least 80% which have lysozyme activity.

In an embodiment, the present invention relates to isolated polypeptides having a sequence identity to the mature polypeptide of SEQ ID NO: 4 of at least 85% which have lysozyme activity.

In an embodiment, the present invention relates to isolated polypeptides having a sequence identity to the mature polypeptide of SEQ ID NO: 4 of at least 90% which have lysozyme activity.

In an embodiment, the present invention relates to isolated polypeptides having a sequence identity to the mature polypeptide of SEQ ID NO: 4 of at least 91% which have lysozyme activity.

In an embodiment, the present invention relates to isolated polypeptides having a sequence identity to the mature polypeptide of SEQ ID NO: 4 of at least 92% which have lysozyme activity.

In an embodiment, the present invention relates to isolated polypeptides having a sequence identity to the mature polypeptide of SEQ ID NO: 4 of at least 93% which have lysozyme activity.

In an embodiment, the present invention relates to isolated polypeptides having a sequence identity to the mature polypeptide of SEQ ID NO: 4 of at least 94% which have lysozyme activity.

In an embodiment, the present invention relates to isolated polypeptides having a sequence identity to the mature polypeptide of SEQ ID NO: 4 of at least 95% which have lysozyme activity.

In an embodiment, the present invention relates to isolated polypeptides having a sequence identity to the mature polypeptide of SEQ ID NO: 4 of at least 96% which have lysozyme activity.

In an embodiment, the present invention relates to isolated polypeptides having a sequence identity to the mature polypeptide of SEQ ID NO: 4 of at least 97% which have lysozyme activity.

In an embodiment, the present invention relates to isolated polypeptides having a sequence identity to the mature polypeptide of SEQ ID NO: 4 of at least 98% which have lysozyme activity.

In an embodiment, the present invention relates to isolated polypeptides having a sequence identity to the mature polypeptide of SEQ ID NO: 4 of at least 99% which have lysozyme activity.

In one aspect, the polypeptides differ by no more than 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, from the mature polypeptide of SEQ ID NO: 4.

A polypeptide of the present invention preferably comprises or consists of the amino acid sequence of SEQ ID NO: 4 or an allelic variant thereof; or is a fragment thereof having lysozyme activity. In another aspect, the polypeptide comprises or consists of the mature polypeptide of SEQ ID NO: 4. In another aspect, the polypeptide comprises or consists of amino acids 20 to 227 of SEQ ID NO: 4.

In an embodiment, the present invention relates to isolated polypeptides having a sequence identity to the mature polypeptide of SEQ ID NO: 8 of at least 80% which have lysozyme activity.

In an embodiment, the present invention relates to isolated polypeptides having a sequence identity to the mature polypeptide of SEQ ID NO: 8 of at least 85% which have lysozyme activity.

In an embodiment, the present invention relates to isolated polypeptides having a sequence identity to the mature polypeptide of SEQ ID NO: 8 of at least 90% which have lysozyme activity.

In an embodiment, the present invention relates to isolated polypeptides having a sequence identity to the mature polypeptide of SEQ ID NO: 8 of at least 91% which have lysozyme activity.

In an embodiment, the present invention relates to isolated polypeptides having a sequence identity to the mature polypeptide of SEQ ID NO: 8 of at least 92% which have lysozyme activity.

In an embodiment, the present invention relates to isolated polypeptides having a sequence identity to the mature polypeptide of SEQ ID NO: 8 of at least 93% which have lysozyme activity.

In an embodiment, the present invention relates to isolated polypeptides having a sequence identity to the mature polypeptide of SEQ ID NO: 8 of at least 94% which have lysozyme activity.

In an embodiment, the present invention relates to isolated polypeptides having a sequence identity to the mature polypeptide of SEQ ID NO: 8 of at least 95% which have lysozyme activity.

In an embodiment, the present invention relates to isolated polypeptides having a sequence identity to the mature polypeptide of SEQ ID NO: 8 of at least 96% which have lysozyme activity.

In an embodiment, the present invention relates to isolated polypeptides having a sequence identity to the mature polypeptide of SEQ ID NO: 8 of at least 97% which have lysozyme activity.

In an embodiment, the present invention relates to isolated polypeptides having a sequence identity to the mature polypeptide of SEQ ID NO: 8 of at least 98% which have lysozyme activity.

In an embodiment, the present invention relates to isolated polypeptides having a sequence identity to the mature polypeptide of SEQ ID NO: 8 of at least 99% which have lysozyme activity.

In one aspect, the polypeptides differ by no more than 45 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, from the mature polypeptide of SEQ ID NO: 8.

A polypeptide of the present invention preferably comprises or consists of the amino acid sequence of SEQ ID NO: 8 or an allelic variant thereof; or is a fragment thereof having lysozyme activity. In another aspect, the polypeptide comprises or consists of the mature polypeptide of SEQ ID NO: 8. In another aspect, the polypeptide comprises or consists of amino acids 20 to 227 of SEQ ID NO: 8.

In another embodiment, the present invention relates to an isolated polypeptide having lysozyme activity encoded by a polynucleotide that hybridizes under medium stringency conditions, medium-high stringency conditions, high stringency conditions, or very high stringency conditions with the mature polypeptide coding sequence of (i) SEQ ID NO: 3 or SEQ ID NO: 7, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 3 or SEQ ID NO: 7 or a subsequence thereof, as well as the polypeptide of SEQ ID NO: 4 or SEQ ID NO: 8 or a fragment thereof, may be used to design nucleic acid probes to identify and clone DNA encoding polypeptides having lysozyme activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having lysozyme activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 3 or SEQ ID NO: 7 or a subsequence thereof, the carrier material is used in a Southern blot.

For purposes of the present invention, hybridization indicates that the polynucleotide hybridizes to a labeled nucleic acid probe corresponding to (i) SEQ ID NO: 3 or SEQ ID NO: 7; (ii) the mature polypeptide coding sequence of SEQ ID NO: 3 or SEQ ID NO: 7; (iii) the cDNA sequence thereof] (iv) the full-length complement thereof; or (v) a subsequence thereof; under medium to very high stringency conditions. Molecules to which the nucleic acid probe hybridizes under these conditions can be detected using, for example, X-ray film or any other detection means known in the art.

In one aspect, the nucleic acid probe is nucleotides 58 to 147 or nucleotides 302 to 835 of SEQ ID NO: 3 or nucleotides 121 to 744 of SEQ ID NO: 7. In another aspect, the nucleic acid probe is a polynucleotide that encodes the polypeptide of SEQ ID NO: 4 or SEQ ID NO: 8; the mature polypeptide thereof; or a fragment thereof. In another aspect, the nucleic acid probe is SEQ ID NO: 3 or SEQ ID NO: 7 or the cDNA sequence thereof.

In another embodiment, the present invention relates to an isolated polypeptide having lysozyme activity encoded by a polynucleotide having a sequence identity to the mature polypeptide coding sequence of SEQ ID NO: 3 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%.

In a further embodiment, the present invention relates to an isolated polypeptide having lysozyme activity encoded by a polynucleotide having a sequence identity to the mature polypeptide coding sequence of SEQ ID NO: 7 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%.

In a preferred embodiment, the present invention relates to variants of the mature polypeptide of SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 4 is not more than 45, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45.

In a preferred embodiment, the present invention relates to variants of the mature polypeptide of SEQ ID NO: 8 comprising a substitution, deletion, and/or insertion at one or more (e.g., several) positions. In an embodiment, the number of amino acid substitutions, deletions and/or insertions introduced into the mature polypeptide of SEQ ID NO: 8 is not more than 45, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides.

Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

The crystal structure of the *Acremonium alkalophilum* CBS114.92 lysozyme was solved at a resolution of 1.3 Å. The atomic coordinates of this structure are shown in FIG. 6. These atomic coordinates can be used to generate a three dimensional model depicting the structure of the *Acremonium alkalophilum* CBS114.92 lysozyme or homologous structures (such as the variants of the present invention).

The *Acremonium alkalophilum* CBS114.92 lysozyme belongs to the GH25 hydrolase family assigned E.C: number 3.2.1.17. The catalytic mechanism is believed to be the classical Koshland retaining mechanism, with net retention configuration of the confirmation around the anomeric carbon. This is often achieved by a two-step, double displacement mechanism involving a covalent glycosyl-enzyme intermediate. The reaction occurs with acid/base and nucleophilic assistance provided by two amino acids side chains. In the first step (often called the glycosylation step), one amino acid residue (D95) plays the role of a nucleophile attacking the anomeric centre to displace the aglycon and form a glycosyl enzyme intermediate. At the same time, the second amino acid residue (E97) functions as an acid catalyst and protonates the glycosidic oxygen as the bond cleaves. In the second step (often called the deglycosylation step), the glycosyl-enzyme intermediate is hydrolyzed by water, with the second amino acid residue (E97) now acting as a base catalyst deprotonating, the incoming water molecule. The $pK_a$ value of the acid/base group is believed to cycle between high and low values during catalysis to optimize for its role at each step of the catalysis.

Using the x/ray structure, amino acid residues D95 and E97 (using SEQ ID NO: 8 for numbering) have been identified as catalytic residues. In embodiments of the invention (in addition to one or more of the alterations recited herein), no alteration is made to amino acid corresponding to E97 and D95, using SEQ ID NO: 8 for numbering, of the lysozyme variants of the present invention. From several lysozyme molecules it is known that mutation of the nucleophile can lead to an enzyme that retains some catalytic activity supposedly because water (perhaps in the form of OH—) can function as a nucleophile in this first step of the catalytic mechanism (Malcolm et al., 1989, "Site-directed mutagenesis of the catalytic residues Asp-52 and Glu-35 of chicken egg white lysozyme", *Proc. Natl. Acad. Sci.* 86(1), 133-137).

Variants Having Lysozyme Activity

The lysozyme variants of the present invention comprise or consist of an alteration at one or more (e.g., several) positions corresponding to positions 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190 of the mature polypeptide of SEQ ID NO: 8 wherein each alteration is independently a substitution, insertion or deletion and the variant has antimicrobial and/or lysozyme activity.

In an embodiment, the alteration is a substitution. In another embodiment, the alteration is an insertion. In a further embodiment, the alteration is a deletion.

The lysozyme variants of the present invention comprises or consists of a polypeptide comprising an amino acid sequence having at least 80%, at least 85%, at least 90%, at least 93%, at least 95%, at least 96%, at least 97%, at least 98% or at least 99% identity with the mature polypeptide of SEQ ID NO: 4.

The lysozyme variants of the present invention comprises or consists of a polypeptide comprising an amino acid sequence having at least 80%, at least 85%, at least 90%, at least 93%, at least 95%, at least 96%, at least 97%, at least 98% or at least 99% identity with the mature polypeptide of SEQ ID NO: 8.

The lysozyme variants of the present invention comprise or consist of a polypeptide comprising an amino acid sequence having at least 85% identity with the mature polypeptide of SEQ ID NO: 8.

The lysozyme variants of the present invention comprise or consist of a polypeptide comprising an amino acid sequence having at least 90% identity with the mature polypeptide of SEQ ID NO: 8.

The lysozyme variants of the present invention comprise or consist of a polypeptide comprising an amino acid sequence having at least 93% identity with the mature polypeptide of SEQ ID NO: 8.

The lysozyme variants of the present invention comprise or consist of a polypeptide comprising an amino acid sequence having at least 95% identity with the mature polypeptide of SEQ ID NO: 8.

The lysozyme variants of the present invention comprise or consist of a polypeptide comprising an amino acid sequence having at least 96% identity with the mature polypeptide of SEQ ID NO: 8.

The lysozyme variants of the present invention comprise or consist of a polypeptide comprising an amino acid sequence having at least 97% identity with the mature polypeptide of SEQ ID NO: 8.

The lysozyme variants of the present invention comprise or consist of a polypeptide comprising an amino acid sequence having at least 98% identity with the mature polypeptide of SEQ ID NO: 8.

The lysozyme variants of the present invention comprise or consist of a polypeptide comprising an amino acid sequence having at least 99% identity with the mature polypeptide of SEQ ID NO: 8.

In one aspect, the number of alterations in the variants of the present invention is 1-45, e.g., 1-40, 1-35, 1-30, 1-25, 1-20, 1-15, 1-10 and 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 alterations.

In another aspect, a variant comprises an alteration, such as a substitution, insertion or deletion, at one or more (e.g., several) positions corresponding to positions 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and 190 of the mature polypeptide of SEQ ID NO: 8. In another aspect, a variant comprises an alteration at two positions corresponding to any of positions 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and 190 of the mature polypeptide of SEQ ID NO: 8. In another aspect, a variant comprises an alteration at three positions corresponding to any of positions 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and 190 of the mature polypeptide of SEQ ID NO: 8. In another aspect, a variant comprises an alteration at each position corresponding to positions 6, 10, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and 190 of the mature polypeptide of SEQ ID NO: 8.

An embodiment of the invention is to alter the pH activity profile of the lysozyme whilst retaining lysozyme activity and/or antimicroibial activity. A preferred embodiment of the invention is that the lysozyme has improved activity at a more alkaline pH; i.e., the pH of peak antimicrobial or lysozyme activity increases/becomes more alkaline.

In one embodiment, the isolated variant of the present invention comprises or consists of an alteration at position 10 (using SEQ ID NO: 8 for numbering). In an embodiment, the alteration comprises or consists of a substitution of an amino acid at position 10 (using SEQ ID NO: 8 for numbering) which alters the pH activity profile of the lysozyme. In another embodiment, the alteration comprises or consists of the substitution W10H which increases the pH of peak antimicrobial activity.

In one embodiment, the isolated variant of the present invention comprises or consists of an alteration at position 39 (using SEQ ID NO: 8 for numbering). In an embodiment, the alteration comprises or consists of a substitution of an amino acid at position 39 (using SEQ ID NO: 8 for numbering) which alters the pH activity profile of the lysozyme. In another embodiment, the alteration comprises or consists of the substitution S39D which increases the pH of peak antimicrobial activity.

In another embodiment, the isolated variant of the present invention consists of an alteration at position 10 (using SEQ ID NO: 8 for numbering) together with an alteration in one or more of the following positions: 6, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190. A preferred embodiment is the substitution W10H together with an alteration in one or more of the following positions: 6, 11, 28, 30, 33, 37, 39, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190.

In another embodiment, the isolated variant of the present invention consists of an alteration at position 39 (using SEQ ID NO: 8 for numbering) together with an alteration in one or more of the following positions: 6, 10, 11, 28, 30, 33, 37, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190. A preferred embodiment is the substitution S39D together with an alteration in one or more of the following positions: 6, 10, 11, 28, 30, 33, 37, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190.

In a further embodiment, the isolated variant of the present invention consists of an alteration at position 10 and 39 (using SEQ ID NO: 8 for numbering). A preferred embodiment consists of the substitutions W10H and S39D.

In a further embodiment, the isolated variant of the present invention consists of an alteration at position 10 and 39 (using SEQ ID NO: 8 for numbering) together with an alteration in one or more of the following positions: 6, 11, 28, 30, 33, 37, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190. A preferred embodiment are the substitutions W10H and S39D together with an alteration in one or more of the following positions: 6, 11, 28, 30, 33, 37, 59, 60, 61, 62, 63, 92, 93, 94, 96, 98, 99, 100, 101, 106, 133, 134, 135, 136, 137, 139, 140, 142, 143, 158, 161, 162, 178, 183 and/or 190.

In one embodiment, the isolated variant of the present invention comprises or consists of an alteration at position 6 (using SEQ ID NO: 8 for numbering). In an embodiment, the alteration comprises or consists of a substitution of an amino acid at position 6 (using SEQ ID NO: 8 for numbering) which alters the substrate specificity of the lysozyme.

In one embodiment, the isolated variant of the present invention comprises or consists of an alteration at position 11 (using SEQ ID NO: 8 for numbering). In an embodiment, the alteration comprises or consists of a substitution of an amino acid at position 11 (using SEQ ID NO: 8 for numbering) which alters the substrate specificity of the lysozyme.

In one embodiment, the isolated variant of the present invention comprises or consists of an alteration at position 30 (using SEQ ID NO: 8 for numbering). In an embodiment, the alteration comprises or consists of a substitution of an amino acid at position 30 (using SEQ ID NO: 8 for numbering) which alters the substrate specificity of the lysozyme.

In one embodiment, the isolated variant of the present invention comprises or consists of an alteration at position 33 (using SEQ ID NO: 8 for numbering). In an embodiment, the alteration comprises or consists of a substitution of an amino acid at position 33 (using SEQ ID NO: 8 for numbering) which alters the substrate specificity of the lysozyme.

In one embodiment, the isolated variant of the present invention comprises or consists of an alteration at position 37 (using SEQ ID NO: 8 for numbering). In an embodiment, the alteration comprises or consists of a substitution of an amino acid at position 37 (using SEQ ID NO: 8 for numbering) which alters the substrate specificity of the lysozyme.

In one embodiment, the isolated variant of the present invention comprises or consists of an alteration at position 101 (using SEQ ID NO: 8 for numbering). In an embodiment, the alteration comprises or consists of a substitution of an amino acid at position 101 (using SEQ ID NO: 8 for numbering) which alters the substrate specificity of the lysozyme.

In one embodiment, the isolated variant of the present invention comprises or consists of an alteration at position 139 (using SEQ ID NO: 8 for numbering). In an embodiment, the alteration comprises or consists of a substitution of an amino acid at position 139 (using SEQ ID NO: 8 for numbering) which alters the substrate specificity of the lysozyme.

In one embodiment, the isolated variant of the present invention comprises or consists of an alteration at position 161 (using SEQ ID NO: 8 for numbering). In an embodiment, the alteration comprises or consists of a substitution of an amino acid at position 161 (using SEQ ID NO: 8 for numbering) which alters the substrate specificity of the lysozyme.

In one embodiment, the isolated variant of the present invention comprises or consists of an alteration at position 162 (using SEQ ID NO: 8 for numbering). In an embodiment, the alteration comprises or consists of a substitution of an amino acid at position 162 (using SEQ ID NO: 8 for numbering) which alters the substrate specificity of the lysozyme.

In one embodiment, the isolated variant of the present invention comprises or consists of an alteration at position 183 (using SEQ ID NO: 8 for numbering). In an embodiment, the alteration comprises or consists of a substitution of an amino acid at position 183 (using SEQ ID NO: 8 for numbering) which alters the substrate specificity of the lysozyme.

In one embodiment, the isolated variant of the present invention comprises or consists of an alteration at position 190 (using SEQ ID NO: 8 for numbering). In an embodiment, the alteration comprises or consists of a substitution of an amino acid at position 190 (using SEQ ID NO: 8 for numbering) which alters the substrate specificity of the lysozyme.

Sources of Polypeptides Having Lysozyme Activity A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a filamentous fungal polypeptide such as an *Acremonium, Aspergillus, Chrysosporium, Fusarium, Humicola, Penicillium, Thielavia* or a *Trichoderma* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

In another aspect, the polypeptide is an *Acremonium alcalophilum* polypeptide, e.g., a polypeptide obtained from *Acremonium alcalophilum* CBS 114.92.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus* or *Acremonium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 3, SEQ ID NO: 7 or the cDNA sequences thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Signal Peptide

The present invention also relates to an isolated polynucleotide encoding a signal peptide comprising or consisting of amino acids amino acids 1 to 19 of SEQ ID NO: 4, or amino acids −40 to −18 of SEQ ID NO: 4. The polynucleotides may further comprise a gene encoding a protein, which is operably linked to the signal peptide. The protein is preferably foreign to the signal peptide. In one aspect, the polynucleotide encoding the signal peptide is nucleotides 1 to 57 of SEQ ID NO: 3 or nucleotides 1 to 69 of SEQ ID NO: 7.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausi, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is an *Acremonium* cell. In a more preferred aspect, the cell is an *Acremonium alcalophilum* cell. In a most preferred aspect, the cell is an *Acremonium alcalophilum* CBS114.92.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides for example the lysozyme spot assay as described below. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Uses

Examples of preferred uses of the lysozyme or compositions thereof of the present invention are given below. The dosage of the lysozyme and other conditions under which the lysozyme is used may be determined on the basis of methods known in the art.

The polypeptides of the invention are typically useful at any locus subject to contamination by bacteria, fungi, yeast or algae. Typically, loci are in aqueous systems such as cooling water systems, laundry rinse water, oil systems such as cutting oils, lubricants, oil fields and the like, where it is desired to kill the microorganisms or at least to control their growth. However, the present invention may also be used in all applications for which known lysozymes compositions are useful, such as protection of wood, latex, adhesive, glue, paper, cardboard, textile, leather, plastics, caulking, and feed.

A lysozyme, or a composition thereof, of the present invention may be used in several applications to degrade a material comprising a peptidoglycan or a chitodextrin by treating the material with the lysozyme or composition thereof (see for example Proctor and Cunningham, 1988, *Critical Reviews in Food Science and Nutrition* 26:359-395; Carini et al., 1985, *Microbiol. Alimen. Nutr.* 3:299-320; Hughey and Johnson, 1987, *Appl. Environ. Microbiol.* 53:2165-2170; Cunningham et al. (1991) *World's Poultry Science Journal* 47:141-163).

Uses of Lysozymes of the Invention for Cleaning and/or Detergents

A lysozyme of the present invention is preferably incorporated into and/or used together with detergent compositions as described below. When washing is performed repeatedly at temperatures below 60° C. there is an increased risk of malodour in the washing machine (laundry as well as dishwashing) and on the textiles or items washed in the machine. This malodour is likely to be caused by microbial organisms such as bacteria, fungi, algae or other unicellular organisms growing in the washing machine.

Furthermore, the invention relates to a process for laundering of fabrics comprising treating fabrics with a washing solution containing a detergent composition and a lysozyme or a lysozyme composition of the invention. The laundering treatment can for example be carried out in a machine washing process or in a manual washing process. The washing solution can for example be an aqueous washing solution containing the detergent composition and with a pH between 3 and 12.

The fabrics subjected to the methods of the present invention may be conventional washable laundry, for example household laundry. Preferably, the major part of the laundry is garments and fabrics, including knits, wovens, denims, yarns, and towelling, made from cotton, cotton blends or natural or manmade cellulosics (e.g., originating from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax/linen, jute, cellulose acetate fibers, lyocell).

The present invention provides a method of reducing microbial contamination on a surface, such as a textile garment or hard surface such as metal, plastic or rubber parts in a washing machine or dish washing machine, bathroom tiles, floors, table tops, drains, sinks and washbasin, by treating the microbially contaminated surface with a lysozyme or lysozyme composition of the present invention. Such a treatment is also expected to reduce the malodour on textiles and hard surfaces containing microbial contamination.

The reduction of microbial contamination can be assessed in several ways, for example by letting a panel assess whether the smell has been decreased, alternatively a sample may be taken from the surface and cultivated to assess whether the microbial count has been reduced as a result of the treatment compared to a treatment without lysozyme.

Uses of Lysozymes of the Invention in Animal Feed

A lysozyme of the invention may also be used in animal feed. In an embodiment, the present invention provides a method for preparing an animal feed composition comprising adding a lysozyme of the present invention to one or more animal feed ingredients.

A lysozyme of the present invention may for example be used to stabilize the healthy microflora of animals, in particular livestock such as, but not limited to, sheep, goats, cattle (including, but not limited to, beef cattle, cows, and young calves), deer, pigs or swine (including, but not limited to, piglets, growing pigs, and sows), poultry (including, but not limited to, geese, turkeys, ducks and chicken such as broilers, chicks and layers); horses, moose and rabbits but also in fish (including but not limited to salmon, trout, tilapia, catfish and carps; and crustaceans (including but not limited to shrimps and prawns)) by suppressing growth/intestinal colonization of viral (such as Coronaviridae, Porcine reproductive and respiratory syndrome virus (PRRSV), Persivirus coursing Bovin virus diarre and likewise), parasitic pathogens (coccidian protozoa, *Eimeria maxima*, *Eimeria mitis*) or bacterial pathogens such as *Clostridium perfringens*, *Escherichia coli*, *Campylobacter coli*, *C. hyointestinalis* and *C. jejuni*, *Yersinia* ssp., *Treponema suis*, *Brachyspira hyodysenteriae*, *Lawsonia intracellularis* and *Salmonella*, such as *Salmonella enterica*, *Salmonella typhimurium* and *Salmonella mbandaka*. In a preferred embodiment a lysozyme is applied to chicken and has anti-microbal activity against *Clostridium perfringens*. In a further embodiment a lysozyme of the present invention is used as a feed additive, where it may provide a positive effect on the microbial balance of the chicken digestive tract and in this way improve animal performance.

A lysozyme of the present invention may also be used in animal feed as feed enhancing enzymes that improve feed digestibility to increase the efficiency of its utilization according to WO 00/21381 and WO 2004/026334.

In a further embodiment a lysozyme of the present invention may be used as a feed additive, where it may provide a positive effect on the animals digestive tract and in this way improve animal performance in accordance to weight gain, feed conversion ratio (FCR), or improved animal health such as decreased mortality rate. FCR is calculated as the feed intake in g/animal relative to the weight gain in g/animal.

Uses of Lysozymes of the Invention as Antimicrobial Agents

A lysozyme of the present invention may be used as antimicrobial agents. One aspect of the present invention is a method for reducing microbial contamination, comprising treating a microbial contaminated surface with a lysozyme of the present invention.

To assess whether a lysozyme of the present invention is capable of acting as an antimicrobial agent it can be tested in a turbidity assay. In this assay it is tested whether the lysozyme is capable of degrading microbial cells, e.g., a dried substrate of *Exiguobacterium undae* cells (isolated from a smelly sock) or *Micrococcus luteus* cells dissolved in buffer or detergent, and thereby reducing the optical density (OD) at for example 540 nm, when compared to a microbial suspension only treated with buffer.

Uses of Lysozymes of the Invention for Disinfection or as a Disinfectant

A lysozyme of the present invention may be useful as a disinfectant or used for disinfection, e.g., for the treatment of infections in the eye or the mouth, or for cleaning and disinfection of contact lenses, and for preventing or removing biofilm on a surface according to U.S. Pat. No. 6,777,223.

A lysozyme of the present invention may also be used in oral care. For example, lysozyme can be used alone or in combination with other enzymes or even antimicrobial peptides in toothpaste or other oral care products. The polypeptides may be introduced into the oral cavity or applied to an article that is to be introduced into the oral cavity. See for example WO 2008/124764.

In general it is contemplated that the polypeptides of the present invention are useful for cleaning, disinfecting or inhibiting microbial growth on any surface. Examples of surfaces, which may advantageously be contacted with the polypeptides of the invention are surfaces of process equipment used, e.g., dairies, chemical or pharmaceutical process plants, water sanitation systems, oil processing plants, paper pulp processing plants, water treatment plants, and cooling towers. The polypeptides of the invention should be used in an amount, which is effective for cleaning, disinfecting or inhibiting microbial growth on the surface in question.

The polypeptides of the invention may additionally be used for cleaning surfaces and cooking utensils in food processing plants and in any area in which food is prepared or served such as hospitals, nursing homes and restaurants.

Uses of Lysozymes of the Invention in Food Applications

A lysozyme of the present invention may also be used to selectively inhibit the uncontrolled growth of *Clostridium tyrobutyricum* during the maturation of cheeses, in particular those made from pressed and cooked curds, e.g., Swiss Cheese, Parmesan, Edam, Gouda, Cheddar, and many others.

A lysozyme of the present invention may also be used in wine making, to control or inhibit microbial contamination.

Uses of Lysozymes of the Invention as Treatments

A lysozyme of the present invention may also be used in topical treatment of dystrophic and inflammatory lesions of the skin and soft tissues. See for example Palmieri and Boraldi, 1977, *Arch. Sci. Med.* (Torino) 134:481-485.

A lysozyme of the present invention may also be used in skin care. For example, the polypeptide is applied to the skin of a patient suffering from a skin infection, such as acne. The lysozyme may also be used in a wound dressing, which is applied to wounded skin, for example, to aid in healing of the wound. See, for example, U.S. Application No. 2008/0254079.

A lysozyme of the present invention may also be used in lipstick, lip balm, lip gel, or lip gloss. For example, such products can be used for treatment of a localized lip infection, for example, a cold sore. See, for example, U.S. Application No. 2008/0254079.

A lysozyme of the present invention may also be used in the treatment of bronchopulmonary diseases.

A lysozyme of the present invention may also be used as digestive enzymes or digestive aids. A lysozyme of the present invention may also be used to improve the use of dead/live bacteria as a food source, e.g., by controlling undesirable microbial contaminants.

A lysozyme of the present invention may also be used as a therapeutic in a human or other animal, e.g., to control or inhibit bacterial overgrowth in the intestines of a human suffering from a disease, e.g., pancreatic disease or an immuno compromised patient.

Uses of Lysozymes of the Invention for Extracting Bacterial Genomic DNA

A lysozyme of the present invention may also be used to aid in the extraction of bacterial genomic DNA from both pure cultures and environmental samples containing multiple bacterial species. In order to be able to sequence bacterial DNA, the bacterial cell wall needs to be broken down to isolate the DNA inside it. Hen egg white lysozyme is the standard enzyme used for DNA isolation from gram positive bacteria and works by hydrolyzing the peptidoglycan chains present in the cell wall thereby aiding in the degradation of the cell walls. However some gram positive cell walls are not degraded by hen egg white lysozymes. For example, it is recommended that cells from, e.g., *Staphylococcus aureus* are lysed with lysostaphin as described by Pitcher and Saunders, 1989, *App. Environ. Microbiol.* 56(3): 782-787. However, these methods do not work for all types of gram positive bacteria and novel lysozymes thus potentially offer access to novel genomes that cannot be isolated with commercial lysozyme solutions Addition of one or more lysozymes of the present invention, optionally together with lysostaphin or hen egg white lysozyme, affords the breakdown of cell walls from bacteria, preferably gram positive bacteria, which is a not possible using current commercial solutions. In an embodiment the lysozyme is a GH25 lysozyme having SEQ ID NO: 4, SEQ ID NO: 8 or a variant thereof. In a further embodiment, the lysozyme is effective in breaking down the cell walls of bacteria from bacteria such as *Bacillus, Micrococcus, Zobellia, Cellulophaga* and *Streptomyces*. An additional embodiment is bacteria such as *Bacillus subtilis, Micrococcus luteus, Zobellia uliginosa, Cellulophaga lytica* and *Streptomyces mobaraensis*. In another embodiment, the lysozyme is effective in combination with hen egg white lysozyme in breaking down the cell walls of bacteria such as *Bacillus, Micrococcus, Zobellia, Cellulophaga* and *Streptomyces,* such as *Bacillus subtilis*, *Micrococcus luteus*, *Zobellia uliginosa*, *Cellulophaga lytica* and *Streptomyces mobaraensis*. A particular embodiment is breaking down the cell walls from the bacteria *Streptomyces mobaraensis*.

The lysozyme of the present invention may be used in a composition or kit to breakdown the cell walls from bacteria, optionally together with lysostaphin or hen egg white lysozyme. The lysozyme component may be a GH25 lysozyme of the present invention or a GH25 lysozyme having SEQ ID NO: 4, SEQ ID NO: 8 or a variant thereof.

Other Uses of Lysozymes of the Invention

A lysozyme of the present invention may also be used to control microbial growth in a fermentation process, such as, in making ethanol or other products from biomass. See, for example, WO 2007/109750. Accordingly, the lysozyme may be used, e.g., in a process for producing a fermentation product comprising (a) liquefying and/or saccharifying a carbohydrate material and (b) fermenting using a fermentation organism, wherein a lysozyme of the present invention is applied to the fermentation process before, during and/or after fermentation concentrations sufficient to kill and/or inhibit growth of bacterial cells.

A lysozyme of the present invention may also be used in controlling microbial growth in a fish or shrimp farm.

Other uses include preservation of foods, beverages, cosmetics such as lotions, creams, gels, ointments, soaps, shampoos, conditioners, antiperspirants, deodorants, enzyme formulations, or food ingredients.

Compositions

In a still further aspect, the present invention relates to compositions comprising a polypeptide of the present invention having antimicrobial and/or lysozyme activity.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Bacterial Genomic DNA Extraction Composition

The lysozyme of the invention may be added to and thus become a component of a composition to extract genomic DNA from bacteria. The lysozyme may additionally be used in combination with one or more further lysozymes, such as but not limited to lysostaphin, mutanolysin or hen egg white lysozyme. The composition may form part of a kit which can be mixed together according to a set of instructions to extract the genomic DNA from bacteria. The kit may contain a buffer, one or more metal ion binders such as EDTA, a protease such as proteinases K, a detergent such as SDS or Triton X and one or more lysozymes, such as the GH25 lysozyme of the invention, lysostaphin, mutanolysin or hen egg white lysozyme. The bacterial genomic DNA may be extracted from both pure cultures and environmental samples containing multiple bacterial species. A preferred embodiment is a GH25 lysozyme having SEQ ID NO: 4, SEQ ID NO: 8 or a variant thereof.

Animal Feed Compositions

The present invention is also directed to methods for using the polypeptides of the present invention having lysozyme activity in animal feed, as well as to feed compositions and feed additives comprising the lysozymes of the invention.

The term animal includes all animals, including human beings. Examples of animals are non-ruminants, and ruminants. Ruminant animals include, for example, animals such as sheep, goats, and cattle, e.g., beef cattle and cows. In a particular embodiment, the animal is a non-ruminant animal. Non-ruminant animals include mono-gastric animals, e.g., pigs or swine (including, but not limited to, piglets, growing pigs, and sows); poultry such as turkeys, geese, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal. In the use according to the invention the lysozyme can be fed to the animal before, after, or simultaneously with the diet. The latter is preferred. Such lysozyme compositions may of course be mixed with other enzymes.

The lysozyme can be added to the feed in any form, be it as a relatively pure lysozyme or in admixture with other components intended for addition to animal feed, i.e., in the form of animal feed additives, such as the so-called pre-mixes for animal feed. In a further aspect the present invention relates to compositions for use in animal feed, such as animal feed, and animal feed additives, e.g., pre-mixes.

Apart from the lysozyme of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g., carotenoids such as beta-carotene, astaxanthin, and lutein; stabilisers; growth improving additives and aroma compounds/flavorings, e.g., creosol, anethol, deca-, undeca- and/or dodeca-lactones, ionones, irone, gingerol, piperidine, propylidene phthalide, butylidene phatalide, capsaicin and/or tannin; polyunsaturated fatty acids (PUFAs); reactive oxygen generating species; also, a support may be used that may contain, for example, 40-50% by weight of wood fibres, 8-10% by weight of stearine, 4-5% by weight of curcuma powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or animal feed at levels of 0.1 ppm to 1000 ppm, preferably 0.5 ppm to 200 ppm and more preferably 1 ppm to 100 ppm. The aforementioned dosing levels can also be used for premixes.

The animal feed composition of the invention may contain at least one vegetable protein, such as that derived from or originating from a vegetable, including modified proteins and protein-derivatives. Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal, Alternatively, the vegetable protein source is material from one or more plants of the family Chenopodiaceae, e.g., beet, sugar beet, spinach or quinoa. Other examples of vegetable protein sources are rapeseed, sunflower seed, cotton seed, and cabbage and cereals such as barley, wheat, rye, oat, maize (corn), rice, triticale, and sorghum.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

Cleaning or Detergent Compositions

The lysozyme of the invention may be added to and thus become a component of a detergent composition, particularly in a liquid detergent having a pH of 7 or lower.

The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the lysozyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

In one embodiment, the invention is directed to cleaning or detergent compositions comprising of an enzyme of the present invention in combination with one or more additional cleaning components. The choice of additional cleaning components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although the components mentioned below are categorized according to a particular function, this should not be construed as a limitation since the component may have one or more additional functionalities which the skilled artisan will appreciate.

The cleaning or detergent composition may be suitable for the laundring of textiles such as, e.g., fabrics, cloths or linen, or for cleaning hard surfaces such as, e.g., floors, tables, or dish wash.

The invention also relates to polynucleotides encoding the polypeptides, nucleic acid constructs, vectors, and host cells comprising the polynucleotides as well as methods of producing and using the polypeptides.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however, the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 45% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium meta-silicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N,N-diacetic acid (SEDA), isoserine-N,N-diacetic acid (ISDA), phenylalanine-N, N-diacetic acid (PHDA), anthranilic acid-N,N-diacetic acid (ANDA), sulfanilic acid-N, N-diacetic acid (SLDA), taurine-N,N-diacetic acid (TUDA) and sulfomethyl-N,N-diacetic acid (SMDA), N-(2-hydroxyethyl)-ethylidenediamine-N,N',N'-triacetate (HEDTA), diethanolglycine (DEG), diethylenetriamine penta(methylenephosphonic acid) (DTPMP), aminotris(methylenephosphonic acid) (ATMP), and combinations and salts thereof.

Further exemplary builders and/or co-builders are described in, e.g., WO 2009/102854, U.S. Pat. No. 5,977, 053.

Bleaching Systems

The detergent may contain 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy) benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators of interest was disclosed in EP 624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

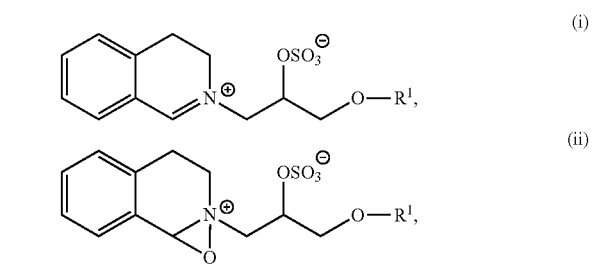

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

Additional Enzymes

In one aspect, the present invention provides a detergent additive comprising a lysozyme of the present invention. The detergent additive as well as the detergent composition may comprise one or more [additional] enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases and Cutinases:

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO96/13580), lipase from strains of *Pseudomonas* (some of these now renamed to *Burkholderia*), e.g., *P. alcaligenes* or *P. pseudoalcaligenes* (EP218272), *P. cepacia* (EP331376), *P.* sp. strain SD705 (WO 95/06720 & WO 96/27002), *P. wisconsinensis* (WO96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/087508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/56782), perhydrolases from the CE 7 family (WO 2009/67279), and variants of the *M. smegmatis* perhydrolase, in particular, the S54V variant used in the commercial product Gentle Power Bleach from Huntsman Textile Effects Pte Ltd (WO 2010/100028).

Amylases:

Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™, Stainzyme™, Natalase™ and BAN™ (Novozymes A/S), Rapidase™ and Purastar™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants:

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents:

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent:

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil Release Polymers:

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents:

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Biofilms

Microorganisms growing in biofilms are less susceptible to all types of antimicrobial agents than the same microorganisms when grown in conventional suspension cultures.

It is well known that starved bacteria can be much less susceptible to a variety of antimicrobial challenges. For example, a number of classical antibiotics such as penicillin, perform poorly in slow or non dividing bacteria. Because lysozyme attacks and destroys the peptidoglycan layer regardless of the growth state of the bacteria, it remains effective.

Biofilm Control; Example Dental Water Lines:

Biofilm buildup within a dental water line can contain biofilms consisting of *Pseudomonas aeruginosa, Proteus mirabilis, Legionella* sp. to name but a few. There is also the possibility of colonisation of species generally found within the oral cavity as a result of the failure of anti retraction valves within the system. The risk of cross infection becomes even more of a potential risk of course when immuno-compromised patients are involved and in this day and age the numbers of patients within this category continues to steadily increase. The need exists for effective control of bacterial biofilm accumulation in dental water lines. A review of biofilms can be found: Watnick and Kolter, 2000, "Biofilm, city of microbes", *J Bacteriol.* 182(10):2675-9.

A typical example of a commercial throat lozenge product is Lysopaine produced by: BOEHRINGER INGELHEIM FRANCE Active Ingredients:
BACITRACIN 200 U.I.
(to 65 iu/mg)
PAPAIN 2 mg
to 30 NK/mg
LYSOZYME CHLORHYDRATE 5 mg
to 26000 U FIP/mg: units determined by measuring OD kinetics of lysis of bacteria suspended in buffer. The unit determination was measured by lysis induced change in turbididy of a bacterial culture suspended in buffer.
Non Active Ingredients:
SACCHARIN excipient
MAGNESIUM STEARATE excipient
Menthol aromatisant
SORBITOL excipient For local treatment of point infections limited to the buccal membranes of the oropharynx. Caution, if clinical indications of a general bacterial infection are evident, antibiotic therapy is advised.

Toothpaste:

Lysozyme can be used alone or in combination with other enzymes or even antimicrobial peptides. Examples of other enzymes are glucose oxidase and lactoperoxidase.

A typical toothpaste composition including lysozyme is "Biotene" by Laclede, Inc., 2030 East University Drive, Rancho Domiguez, Calif. 90220, USA.

Active Ingredients
Contains: Lactoperoxidase (100 gm)
Inactive Ingredients
Glucose Oxidase, Lysozyme, Sodium Monofluorophosphate, Sorbitol, Glycerin, Calcium Pyrophosphate, Hydrated Silica, Zylitol, Cellulose Gum, Flavor, Sodium Benzoate, Beta-d-glucose, Potassium Thiocyanate The present invention is further described by the following examples that should not be construed as limiting the scope of the invention.

EXAMPLES

Strains

*Aspergillus oryzae* MT3568 strain was used for expression of the *Acremonium alkalophilum* gene encoding the GH25 enzyme. *A. oryzae* MT3568 is an amdS (acetamidase) disrupted gene derivative of *Aspergillus oryzae* JaL355 (WO 02/40694) in which pyrG auxotrophy was restored by disrupting the *A. oryzae* acetamidase (amdS) gene with the pyrG gene. According to Central Bureau vor Schnimmelkulture, *Acremonium alkalophilum* CBS 114.92 was isolated by A. Yoneda in 1984 from the sludge of pig faeces compost near Tsukui Lake, Japan. *Aspergillus oryzae* Toc1512 was used for expression of the *Acremonium alkalophilum* gene encoding GH25 enzyme (SEQ ID NO: 7) and variants. *A. oryzae* is and pyrG deficient strain that can be transformed with an pyrG gene and transformants selected by their ability to grow in the absence of uridine.

Media and Solutions

YP medium was composed of 10 g of yeast extract, 20 g of Bactopeptone, and deionized water to 1 liter.

LB medium was composed of 10 g of tryptone, 5 g of yeast extract, 5 g of sodium chloride, and deionized water to 1 liter.

MDU-2 Bp medium was composed of per liter 45 g maltose-1$H_2O$, 7 g yeast extract, 12 g $KH_2PO_4$, 1 g $MgSO_4$-7$H_2O$, 2 g $K_2SO_4$, 5 g Urea, 1 g NaCl, 0.5 ml AMG trace metal solution pH 5.0.

G2-Gly media was composed of 18 g of yeast extract, 24 g of glycerol (86-88%), 1 ml Dowfax 63N10 and deionized water to 1 liter.

Horikoshi aqar medium was composed of: 1% (w/v) Dextrose, 1% soluble starch, 0.5% (w/v) peptone, 0.5% (w/v) yeast extract, 0.02% (w/v) $MgSO_4$-7$H_2O$, 0.1% (w/v) $K_2HPO_4$, and 15 g (w/v) of Bacto-agar. 1% (w/v) $Na_2CO_3$ was added separately after sterilization.

Bacto aqar plates were composed of LB medium and 15 g of Bacto agar per liter.

PDA aqar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g (w/v) of dextrose and 20 g (w/v) of agar powder. The medium was sterilized by autoclaving at 15 psi for 15 minutes (Bacteriological Analytical Manual, 8th Edition, Revision A, 1998).

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl and Triton X-100 (50 µl/500 ml) were added.

NaNO$_3$ Sucrose plates were composed of 20 ml COVE salt solution, 20 g of agar powder, 342 g sucrose and deionized water to 1 liter. The medium was sterilized by autoclaving at 15 psi for 15 minutes (Bacteriological Analytical Manual, 8th Edition, Revision A, 1998). The medium was cooled to 60° C. and 10 mM NaNO$_3$ and Triton X-100 (50 µl/500 ml) were added.

LB aqar plates were composed of 37 g of LB agar and deionized water to 1 liter.

COVE salt solution was composed of 26 g of MgSO$_4$.7H$_2$O, 26 g of KCL, 26 g of KH$_2$PO$_4$, 50 ml of COVE trace metal solution, and deionized water to 1 liter.

COVE trace metal solution was composed of 0.04 g of Na$_2$B$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_4$.2H$_2$O, 10 g of ZnSO$_4$.7H$_2$O, and deionized water to 1 liter.

AMG trace metals were composed of per liter 14.3 g ZnSO$_4$-7H$_2$O, 2.5 g CuSO$_4$-5H$_2$O, 0.5 g NiCl$_2$, 13.8 g FeSO$_4$, 8.5 g MnSO$_4$, 3.0 g citric acid.

COVE N-gly slants were composed of 10 g of 100% glycerol, 50 ml of COVE salt solution, 218 g sorbitol, 2.02 g KNO$_3$, 25 g agar, and deionized water to 1 liter.

Example 1: Lysozyme Assay

*Xanthomonas campestris* is the production organism for all xanthan gum production. The separation of *Xanthomonas* cells from the highly viscous xanthan solution is a cost-intensive process in the industrial production (Homma et al., EP 690072, Murofushi et al., EP 718311, U.S. Pat. No. 5,702,927). Nowadays, the favoured method for recovering xanthan from the fermentation liquid is precipitation with alcohol, mainly isopropanol, after pasteurization to destroy bacterial cells and enzymes (Cottrell et al., 1978, "Xanthan gum: A unique bacterial polysaccharide for food applications", *Ind. Microbiol.* 19:177). Subsequently the xanthan/cell debris precipitate is spray dried and milled to a powder. The alcohol is recovered by distillation. Because of the significant amounts of *Xanthomonas* cell wall debris in some commercial preparations of xanthan gum, and this debris is peptidoglycan rich *Xanthomonas* cell wall material, the gum can be used as a convenient assay for peptidoglycan degrading activity.

Solid Plate Assay:

Commercially prepared Xanthan gum (Sigma #G-1253) is dissolved in a buffered solution or bacterial growth media to 0.5% w/v in the presence of 0.7% agarose and then autoclaved. Enzyme preparations, supernatants or whole organisms are either deposited in wells cut out of the Bacto agar plates or deposited directly on the surface of the media. The preparations are able to form clearing zones in the plates. These clearing zones can indicate degradation of bacterial cell wall material.

Liquid Clearing Assay:

Commercially prepared xanthan gum is dissolved in a buffered solution in the presence or absence of sodium chloride. The solution is autoclaved and used for studies of xanthan gum clearing. Enzyme preparations, supernatants or whole organisms are added to the assay medium and incubated. Resulting treatments are measured in a spectrophotometer to determine the OD of the solution. Typically, a wavelength of 600 nm is used.

Example 2: Cloning and Characterization of the Lysozyme Encoding Gene from *Acremonioum alkalophilum* (SEQ ID NO: 4)

Genomic sequence information was generated by the U.S. Department of Energy Joint Genome Institute (JGI). According to Central Bureau vor Schnimmelkulture, *Acremonium alkalophilum* CBS 114.92 was isolated by A. Yoneda in 1984 from the sludge of pig faeces compost near Tsukui Lake, Japan. A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH25 homologues in the genome. More precise gene models were constructed manually using multiple known GH25 protein sequences as a guide.

*Acremonium alkalophilum* CBS 114.92 was propagated on Horikoshi agar, pH 9 for 7 days at 30° C. Mycelia was harvested directly from the plate and DNA was isolated according to the FastDNA SPIN Kit for Soil (www.mpbio.com). The DNA was eluted in 100 ul 10 mM TRIS buffer, 0.1 mM EDTA, pH 7.5 and stored at 4° C. until use.

The pair of synthetic oligonucleotide primers shown in table 1 below were designed to PCR amplify the *A. alkalophilum* CBS114.92 P242M9 GH25 gene, from the *A. alkalophilum* genomic DNA. An IN-FUSION™ Cloning Kit (Clontech, Mountain View, Calif., USA) was used to clone the fragment directly into the expression vector pDau109 (WO 2005/042735).

TABLE 1

Primers used for GH25 PCR Amplification

| GH25 gene | Specific forward primer | Specific reverse primer |
|---|---|---|
| A. alkalophilum CBS114.92 GH25 P242M9 | F-P242M9<br>5'-<u>ACACAACTGGGGATCC</u>ACCAT GAAGCTTCTTCCCTCCTTGA-3'<br>(SEQ ID NO: 5) | R-P242M9<br>5'-<u>AGATCTCGAGAAGCTT</u>ATTAGTCTC CGTTAGCGAGAGC-3'<br>(SEQ ID NO: 6) |

Bold letters represent coding sequence. The underlined sequence is homologous to the insertion sites of pDau109.

The PCR reaction (25 µl) was composed of 12.5 µl of 2× IPROOF™ HF Master Mix, 0.5 µl of primer F-P242M9 (100 µM), 0.5 µl of primer R-P242M9 (100 µM), 0.5 µl of genomic (100 ng/µl), and 11 µl of deionized water.

The PCR reaction (25 µl) was composed of Phusion High-Fidelity DNA Polymerase (Cat. No. F-530S, Thermoscientific, USA), 5 uls 5× Pfusion buffer, 0.5 ul 10 mM dNTP, 0.5 µl of primer F-P242M9 (100 µM), 0.5 µl of primer R-P242M9 (100 µM), 0.5 µl of genomic (100 ng/µl), and 18 µl of deionized water. The PCR reaction was incubated in a DYAD® Dual-Block Thermal Cycler (MJ Research Inc., Waltham, Mass., USA) programmed for 1 cycle at 95° C. for 2 minutes; 35 cycles each at 98° C. for 10 seconds, 72° C. for 2 minutes and 30 seconds, 1 cycle at 72° C. for 10 minutes. Samples were cooled to 12° C. before removal and further processing.

Five µl of the PCR reaction were analyzed by 1% agarose gel electrophoresis using TAE buffer where an approximately 874 bp product band was observed. The remaining PCR reaction was purified using an ILLUSTRA™ GFX™ PCR DNA and Gel Band Purification Kit according to the manufacturer's instructions.

The fragment was then cloned into Hind III and Bam HI digested pDau109 using an IN-FUSION™ Cloning Kit resulting in plasmid pP242M9. Cloning of the P242M9 gene into Hind III-Bam HI digested pDau109 resulted in the transcription of the *Aspergillus aculeatus* P242M9 gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P242M9 GH25 construct. The treated plasmid and insert were transformed into Fusion Blue™ *E. coli* cells (Clontech, Mountain View, Calif., USA) according to the manufacturer's protocol and plated onto LB plates supplemented with 50 µg of ampicillin per ml. After incubating at 37° C. overnight, colonies were seen growing under selection on the LB ampicillin plates. Ten colonies transformed with the P242M9 GH25 construct were cultivated in LB medium supplemented with 50 µg of ampicillin per ml and plasmid was isolated using a FASTPlasmid mini kit from SPrime (5 PRIME GmbH, Konigstrasse 4a, 22767 Hamburg, Germany) according to the manufacturer's instructions.

Isolated plasmids were sequenced with vector primers and in order to determine a representative plasmid expression clone that was free of PCR errors. The DNA sequencing of the *Acremonium alkalophilum* CBS114.92 GH25 genomic clones were performed with an Applied Biosystems Model 3730xl Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequences obtained were identical to the sequences from the JGI.

The nucleotide sequence and deduced amino acid sequence of the *Acremonium alkalophilum* P242M9 GH25 gene are shown in SEQ ID NO: 3 and SEQ ID NO: 4, respectively. The coding sequence is 838 bp including the stop codon and is interrupted by one intron of 154 bp (nucleotides 148 to 301). The encoded predicted protein is 227 amino acids. Using the SignalP program (Nielsen et al., 1997, *Protein Engineering* 10: 1-6), a signal peptide of 19 residues was predicted. The predicted mature protein contains 207 amino acids.

The *Aspergillus oryzae* strain MT3568 was used for all experiments. *Aspergillus oryzae* MT3568 is an amdS (acetamidase) disrupted derivative of *A. oryzae* JaL355 (WO 02/40694) in which pyrG auxotrophy was restored in the process of knocking out the *A. oryzae* amdS gene. *A. oryzae* MT3568 protoplasts were prepared according to the method of EP 0238023, pages 14-15. Fresh protoplasts of *A. oryzae* MT3568 were prepared and transformed with the pP242M9 GH25 plasmid. Plasmid DNA from the above mini prep procedure was used to transform *A. oryzae* MT3568.

Six ul containing about 3.0 µg total DNA was used for the transformation. The DNA was gently added to 100 µl of *A. oryzae* MT3568 protoplasts and 250 µl of 60% PEG 4000 (Sigma-Aldrich cat. No. 95904). The 60% (W/V) PEG 4000 was prepared in the following manner: PEG 4000 powder was dissolved in double distilled H2O and then heated for 10-20 seconds in a microwave oven at 800 watt until dissolved. The dissolved solution was cooled down to room temperature and then adjusted with $CaCl_2$ solution and Tris-HCl solution (pH 7.5) for a final concentration of 10 mM of each. After adding the 60% PEG 4000 solution, the tube was gently mixed and incubated at 37° C. for 30 minutes. The mix was added to 6 ml of top agar with 10 mM acetamide and plated onto COVE-sorbitol plates with 10 mM acetamide.

The plates were incubated at 37° C. for 3 or more days and then moved to 26° C. for two days. Spores from 4 individual colonies were picked by first dipping a white 10 µl inoculation pin (Nunc A/S, Denmark) in a 0.1% TWEEN® 80 solution, contacting the sporulating colony on the selection plate, and restreaking with the pin onto fresh COVE sorbitol plates containing 10 mM acetamide. After 5 days at 26° C., spores from the restreaked colonies were used to inoculate a 96 well deep dish plate (NUNC, cat. no. 260251, Thermoscientific, USA). The wells of the deep dish plate contained 500 uls of either YP+2% glucose or YP+2% maltodextrin media. The inoculated plate was sealed with gas permeable tape (89009-656, VWR.com). Plates were incubated stationary at 30° C. for 5 days. Expression was verified by analysis of 20 uls of harvested culture fluid on SDS-PAGE using a NUPAGE® 10% Bis-Tris gel (Invitrogen, Carlsbad, Calif., USA) and Coomassie blue staining. One transformant was selected for further work and designated *A. oryzae* EXP03864.

Spores of EXP03864 were inoculated into DAP-4C-1 medium (100 mls in 500 ml Erlenmeyer shake flask with baffles). The cultures were incubated at 26° C. and 150 rpm, 3 days and if necessary 4 days. An SDS gel was run as above to test protein amount.

Plate Test for Lysozyme Activity

A Spot assay was performed with Xanthan gum, at pH 5, 7 and 8 as described in the section lysozyme plate assay.

A 1.5% Agarose (Invitrogen cat. 15510-027, electrophoresis grade) solution was prepared in the following buffers:
pH ~5—in water
pH ~7—in 0.02 M potassium phosphate pH 7
pH ~8—in 0.02 M potassium phosphate pH 8

The agarose was autoclaved for 20 minutes at 121° C. 0.5% Xanthan gum (Sigma G1253) was dissolved in the melted 1.5% agarose and the mixture poured into petri plates. When the plates were set, sample application wells were made with a P-1000 pippette tip (cut off to a 3 mm diameter) attached to a vacuum line.

20 ul of the culture fluid of EXP03899 was deposited in the application wells and incubated at 37° C. overnight. Samples with lysozyme activity were observed by clearing zones where the cell debris in the xanthan gum was observed. Culture fluids from EXP03864 displayed such a clearing zone while the *Aspergillus oryzae* untransformed transformation host MT3568 did not produce a noticeable clearing zone. The remaining culture EXP03899 fluid was filtered though a Fast PES Bottle top filter with a 0.22 μm cut-off. and stored in aliquots at −20° C. until further use.

Example 3: RDA (Radial Diffusion Assays)

Initially, the antimicrobial activity of the culture supernatants and purified fractions containing the recombinantly expressed lysozymes was confirmed using an RDA's as described previously by Lehrer et al. (Lehrer et al., 1991, "Ultrasensitive assays for endogenous antimicrobial polypeptides", *J. Immuno. Methods* 137:167-73), with several modifications. Briefly, 30 mL of melted ⅒ Mueller-Hinton broth (MHB) (Sambrook J, Fritsch E F, Maniatis T. Molecular Cloning: A Laboratory Manual. Cold Spring Harbor: Cold Spring Harbor Laboratory Press, 1989) with 1% agarose was cooled to 42° C., supplemented to $5.0 \times 10^5$ cfu/mL with *S. carnosus* ATCC 51365 or *E. coli* DSM682 (ATCC 10536) and was poured into a single-well omnitray (Nunc) plate. The omnitray plate was overlayed with a TSP plate (Nunc) and left to solidify. After 1 h, the TSP plate was removed; leaving 96 1-mm wells in which 10 μL of the compound of interest could be tested.

10 μl of the test solution is spotted pr. well and the plates are incubated O/N at 37° C. The following day clearing zones indicated no growth of test bacteria and thereby antimicrobial activity. The clearing zones were visualized by colouring with MTT (3-(4,5-dimethylthiazol-2-yl)-2,5-diphenyltetrazolium bromide, a yellow tertrazole), that is reduced to purple formazan in living cells (Mosmann, 1983, "Rapid colorimetric assay for cellular growth and survival: application to proliferation and cytotoxicity assays", *Journal of Immunological Methods* 65(1-2): 55-63). This colouring provides for a dark colouring of living cells and no colouring of the clearing zones without living cells.

The *Aspergillus fumigatus* GH25 lysozyme (prepared as disclosed in Korczynska et al, *Acta Cryst.* (2010) F66, 973-977) was included in the test as a reference. The purified samples shown in table 2 below have been tested in the RDA assay.

TABLE 2

Radial Diffusion Assay of GH24 and GH25 Lysozymes

| Lysozyme | Stock conc. | Dilution 0.7 ug/ul | Dilution 0.35 ug/ul |
| --- | --- | --- | --- |
| *A. alcalophilum* GH24 SEQ ID NO: 2 | 1.4 μg/ul | 37.5 μl enz. + 37.5 μl water | 18.8 μl enz. + 56.2 μl water |
| *A. alcalophilum* GH25 SEQ ID NO: 4 | 0.77 μg/ul | 68.2 μl enz. + 6.8 μl water | 34.1 μl enz. + 40.9 μl water |
| *A. fumigatus* GH25 (reference) | 12.2 μg/ul | 4.3 μl enz. + 70.6 μl water | 2.2 μl enz. + 72.8 μl water |

Measurement of Clearing Zones

The experiment was performed in triplicate with all resulting in same measured clearing zones/zones of inhibition, see FIG. 1. Table 3 below shows the clearing zones in mm.

TABLE 3

Antimicrobial Clearing Zones of the GH25 Lysozymes Against *Staphylococcus carnosus* and *Escherichia coli*.

| | 0.7 μg/μl S. carnosus | 0.35 μg/μl S. carnosus | 0.7 μg/μl E. coli | 0.35 μg/μl E. coli |
| --- | --- | --- | --- | --- |
| *A. alcalophilum* GH24 SEQ ID NO: 2 | 12 | 10 | 16 | 14 |
| *A. alcalophilum* GH25 SEQ ID NO: 4 | faint | faint | 8 (cloudy) | 6 (cloudy) |
| *A. fumigatus* GH25 (reference) | 11 | 10 | 10 | 8 |

The purified lysozyme *A. alcalophilum* GH24 (SEQ ID NO: 4) showed antimicrobial activity against viable cells of the gram positive bacteria *Staphylococcus carnosus* and the Gram negative bacteria *Escherichia coli*.

The antimicrobial activity is not present in culture supernatants from the untransformed *Aspergillus* production host (results not shown).

Large clearing zones with non defined borders were observed surrounding the application zone for *A. alcalophilum* GH24 (SEQ ID NO: 2). The experiment indicates that the *A. alcalophilum* lysozyme (SEQ ID NO: 2) and the *Aspergillus fumigatus* GH25 reference lysozyme have different activity and specificity against the two bacteria tested in this example.

Example 4: Turbidity Assay

The activity of lysozyme was determined by measuring the decrease (drop) in absorbance/optical density of a solution of resuspended *Micrococcus lysodeikticus* ATTC No. 4698 (Sigma-Aldrich M3770) or *Exiguobacterium undea* (DSM14481) measured in a spectrophotometer at 540 nm.
Preparation of *Micrococcus lysodeikticus* Substrate Before use the cells were resuspended in citric acid—phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.
Preparation of Citric Acid—Phosphate Buffer pH 6.5

29 mL 0.1 M citric acid was mixed with 61 mL 0.2 M $Na_2HPO_4$, and the pH was adjusted with HCl or NaOH to pH 6.5.

Preparation of Dried Cells of *Exiquobacterium undae* (the Substrate)

A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C. and 5000 g for 10 minutes, and the pellet was washed two times in sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid—phosphate buffer pH 6.5 so that the optical density (OD) at 540 nm=1.

Measurement of Lysozyme Antimicrobial Activity in the Turbidity Assay

The lysozyme sample to be measured was diluted to a concentration of 100-200 mg enzyme protein/L in citric acid—phosphate buffer pH 6.5, and kept on ice until use. In a 96 well microtiterplate (Nunc) 200 µL of the substrate was added to each well, and the plate was incubated at 25° C. or 37° C. for 5 minutes in a VERSAmax microplate reader (Molecular Devices). Following incubation, the absorbance of each well was measured at 540 nm (start value). To start the activity measurement, 20 µL of the diluted lysozyme sample was added to each substrate (200 µL) and kinetic measurement of absorbance at 540 nm was initiated for minimum 30 minutes up to 24 hours at 25° C. or 37° C. The measured absorbance at 540 nm was monitored for each well and over time a drop in absorbance is seen if the lysozyme has lysozyme activity.

The *Aspergillus fumigatus* GH25 lysozyme (Korczynska et al (2010) supra.) was included in the test as a reference and the results are shown in table 4 below.

TABLE 4

Lysozyme Activity of GH25 Lysozymes against *Micrococcus lysodeikticus* and *Exiguobacterium undea* as measured by Optical Density Drop

|  | *Micrococcus lysodeikticus* | *Exiguobacterium undae* | |
| --- | --- | --- | --- |
| Temperature | 37° C. | 25° C. | 37° C. |
| A. alcalophilum GH25 (SEQ ID NO: 4) | NT | ++ | +++ |
| A. fumigatus GH25 (reference) | + | +++ | +++ |

NT means not tested
− Means no effect
+ means small effect
++ means medium effect
+++ means large effect Example 5: Purification of P242M9 GH25 Protein in *Aspergillus oryzae*

The fermentation supernatant with the lysozyme was filtered through a Fast PES Bottle top filter with a 0.22 µm cut-off. pH was adjusted to 4.5 with 10% acetic acid. After the pH-adjustment the solution became a little cloudy and this was removed by filtration through a Fast PES Bottle top filter with a 0.22 µm cut-off.

After pretreatment about 650 ml of the lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5. The fractions from the column were pooled based on the chromatogram (absorption at 280 and 254 nm) and SDS-PAGE analysis. The pooled fractions were buffer-changed into 50 mM Na-acetate, pH 5.5 and concentrated using Amicon spin filters with a 10 kDa cut-off.

The molecular weight, as estimated from SDS-PAGE, was approximately 22 kDa and the purity was >95%.

Example 6: Temperature Stability of P242M9 GH25

Temperature stability was determined for *Acremonium alcalophilum* P242M9 GH25 lysozyme (SEQ ID NO: 4). The purpose of this study is to determine residual activity of *Acremonium alcalophilum* GH25 lysozyme after heat treatment at 60° C.-85° C.

Samples were incubated at different temperature for a short period of time (30 s and 60 s) after which the residual activity was measured for 1 h at 37° C. in a citric acid—phosphate buffer using gram positive bacteria *Micrococcus luteus* as substrate. OD drop turbidity assay at 540 nm was used to determine lysozyme activity.

Heat Treatment

The heat treatment was performed in a buffered solution of *Acremonium alcalophilum* GH25 lysozyme (SEQ ID NO: 4) in a preheated PCR Thermocycler (GeneAmp PCR system 9700) for 30/60 sec at different temperatures. 60, 65, 70, 75, 80 and 85° C. were used for either 30 or 60 seconds after which the tubes were placed on an ice bath for instant cooling of the samples.

Turbidity Assay

The activity of lysozyme was determined by measuring the decrease (drop) in absorbance/optical density of a solution of re-suspended *Micrococcus luteus* (also named *Micrococcus lysodeikticus*) ATTC No. 4698 (Sigma-Aldrich M3770) measured in a spectrophotometer at 540 nm.

Preparation of *Micrococcus luteus* Substrate

Before use the cells were re-suspended in citric acid—phosphate buffer (prepared by mixing 29 mL 0.1 M citric acid with 61 mL 0.2 M $Na_2HPO_4$ and adjusting to pH 6.5 with HCl or NaOH) to a concentration of 0.5 mg cells/mL and the optical density (OD) at 540 nm was measured. The cell suspension was then adjusted so the cell concentration equaled an OD540=1.0. The adjusted cell suspension was then stored cold before use. Suspended cells were used within 4 hours.

Measurement of Lysozyme Antimicrobial Activity in the Turbidity Assay

The lysozyme sample was diluted to a concentration of 100-200 mg enzyme protein/L in citric acid—phosphate buffer, and kept on ice until use. In a 96 well microtiterplate (Nunc), the *Micrococcus luteus* substrate (200 µL) was added to each well, and the plate was incubated at 37° C. for 5 minutes in a VERSAmax microplate reader (Molecular Devices). Following the incubation the absorbance of each well was measured at 540 nm (start value). To start the activity measurement, the diluted lysozyme sample (20 µL) was added to the pH adjusted diluted substrate (200 µL) in each well and kinetic measurement of absorbance at 540 nm was initiated for minimum 30 minutes up to 24 hours at 37° C.

Figure 2:
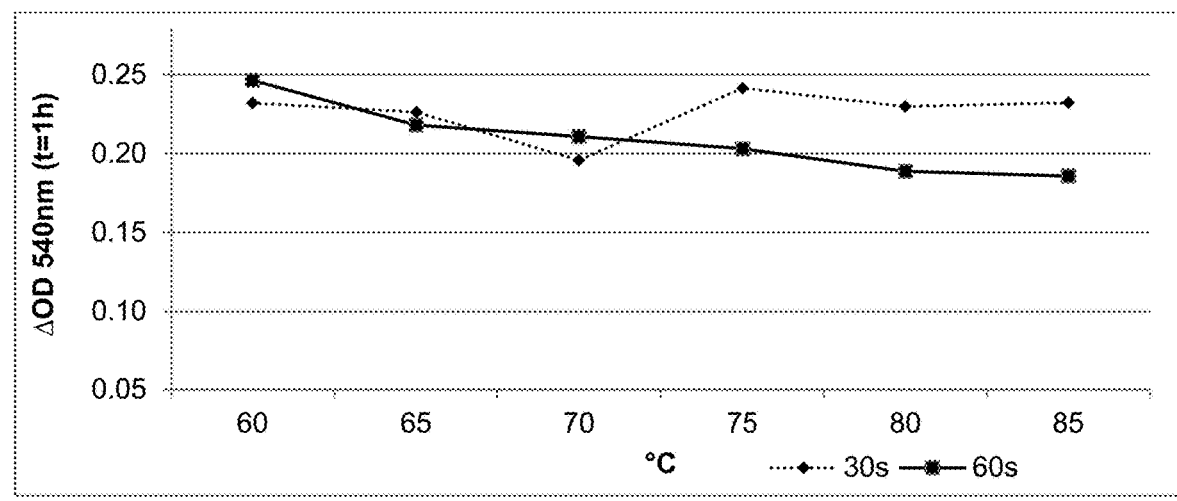
FIG. 2 shows the temperature stability of the *Acremonium alcalophilum* GH25 lysozyme P242M9 (SEQ ID NO: 4) at 60, 76, 70, 75, 80 and 85° C. after 30 or 60 seconds as determined by optical density drop of a solution of re-suspended *Micrococcus luteus* ATTC No. 4698 measured in a spectrophotometer at 540 nm.

The measured absorbance at 540 nm was monitored for each well and over time a drop in absorbance is seen if the lysozyme has antimicrobial activity. The difference between the absorbance at T=0 and the time points was calculated as the ΔOD and compared between test substances (table 5 and FIG. 2). The percentage remaining activity was calculated by comparing the ΔOD of the heat treated sample with the ΔOD of the sample which was not heat treated. The experiment described above was performed in triplicate.

TABLE 5

Temperature Stability of the P242M9 GH25 Lysozyme as measured by OD Drop

| Time | Temperature (° C.) | | | | | | |
|---|---|---|---|---|---|---|---|
| (Sec) | 60 | 65 | 70 | 75 | 80 | 85 | No heat |
| 30 | 0.2320 | 0.2263 | 0.1958 | 0.2416 | 0.2300 | 0.2322 | 0.2210 |
| 60 | 0.2464 | 0.2181 | 0.2109 | 0.2031 | 0.1888 | 0.1858 | 0.2268 |

TABLE 6

Percentage Remaining Activity of the P242M9 GH25 Lysozyme

| | Temperature (° C.) | | | | | | |
|---|---|---|---|---|---|---|---|
| Time (Sec) | 60 | 65 | 70 | 75 | 80 | 85 | No heat |
| 30 | 105% | 102% | 89% | 109% | 104% | 105% | 100% |
| 60 | 109% | 96% | 93% | 90% | 83% | 82% | 100% |

The results show that the P242M9 GH25 lysozyme is stable after 30 seconds even at 85° C. and that the GH25 lysozyme retains over 80% activity even after 60 seconds at 85° C.

Example 7: Thermostability of P242M9 GH25 Determined Using DSC

An aliquot of the protein sample of lysozyme (P242M9 GH25), purified as described in Example 7, was buffer-changed (see buffer in table below) using a prepacked PD-10 column. The sample was 0.45 μm filtered and diluted with buffer to approx. 2 A280 units. The buffer was used as reference solution. The thermostability of the lysozyme in different pH values was determined by Differential Scanning Calorimetry (DSC) using a VP-capillary DSC instrument (MicroCal Inc., Piscataway, N.J., USA) equipped with an auto sampler. The thermal denaturation temperature, Td (° C.), was taken as the top of denaturation peak (major endothermic peak) in thermograms (Cp vs. T) obtained after heating the lysozyme solutions in the buffer at a constant programmed heating rate.

Figure 3:
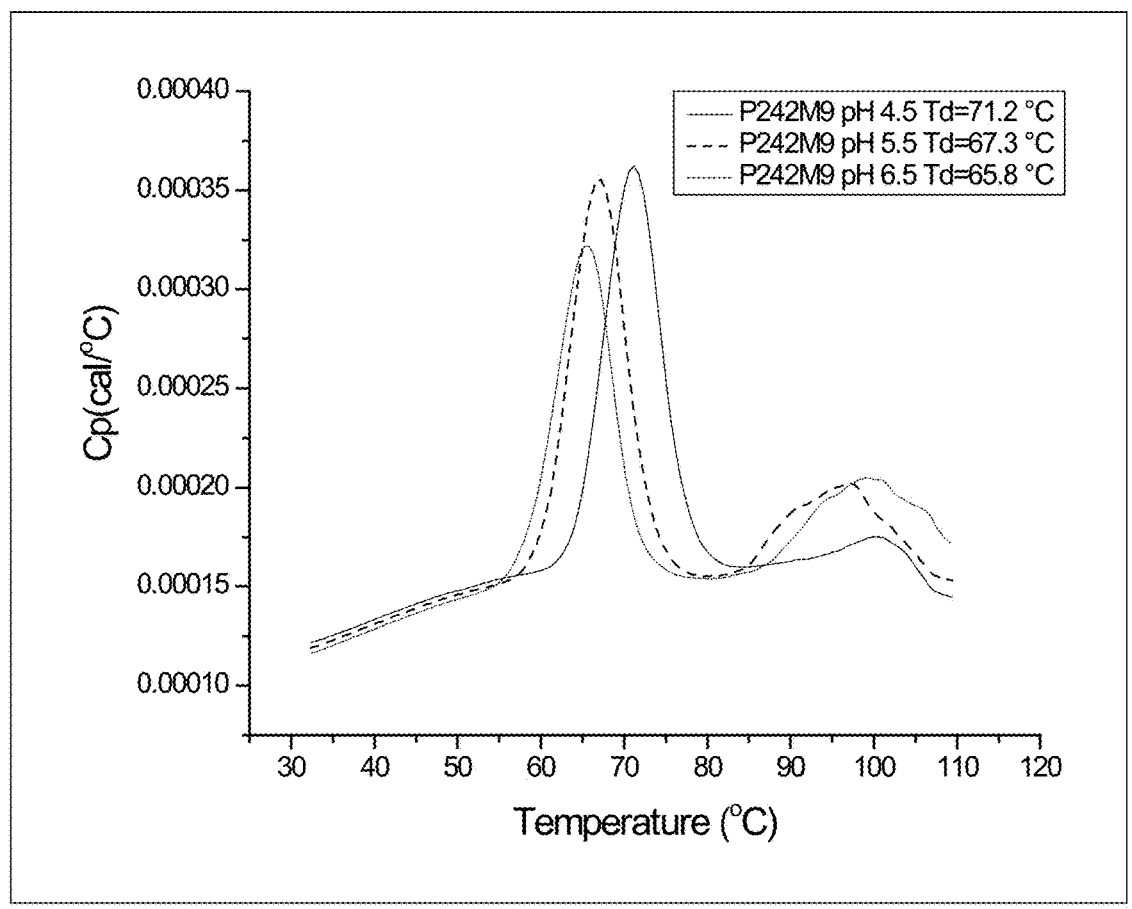
FIG. 3 shows the thermostability of the GH25 lysozyme P242M9 (SEQ ID NO: 4) as determined using Differential Scanning Calorimetry (DSC) in 50 mM Na-acetate pH4.5, 50 mM Na-acetate pH 5.5 and 50 mM MES (2-(N-morpholino)ethanesulfonic acid), pH 6.5.

Sample and reference solutions (approx. 0.5 ml) were thermally pre-equilibrated for 10 minutes at 20° C. and the DSC scan was performed from 20 to 110° C. at a scan rate of 200 K/hour. Data-handling is performed using the Micro-Cal Origin software (version 7.0383). Denaturation temperatures were determined at an accuracy of approximately +/−0.5° C. The results of the DSC measurements are summarized in table 7 and FIG. 3.

TABLE 7

Denaturation Temperature of the P242M9 GH25 Lysozyme

| Buffer | Td (° C.) |
|---|---|
| 50 mM Na-acetate, pH 4.5 | 71.2 |
| 50 mM Na-acetate, pH 5.5 | 67.3 |
| 50 mM MES (2-(N-morpholino)ethanesulfonic acid), pH 6.5 | 65.8 |

Example 8: Cloning and Expression of Lysozyme Encoding Genes from Acremonioum alkalophilum (SEQ ID NO: 8)

Based on the nucleotide sequence identified as SEQ ID NO: 3, a synthetic gene having SEQ ID NO: 7, was synthesized by Gene Art (GENEART AG BioPark, Josef-Engert-Str. 11, 93053, Regensburg, Germany). The PCR primer set listed below in table 8 was used to PCR amplify the synthetic GH25 gene. For cloning purposes the restriction sites BamHI and EcoRI were introduced in the end of the PCR fragment (restriction sites are underlined in the primer sequences listed below and bold letters represent coding sequence).

TABLE 8

Primers used for PCR amplification of the GH25

| GH25 gene | Specific forward primer | Specific reverse primer |
|---|---|---|
| Synthetic gene | Fwd. BamHI<br>5'TACACAACTGGGGATCCAGCGGCCG<br>CACCATGAAGTTCTTCACCAC-3'<br>SEQ ID NO: 9 | Rev. EcoRI<br>5'-ATACTTGTCCGAATTCCT<br>AATCGCCGTTCGCCAATGC-3'<br>SEQ ID NO: 10 |

The PCR fragment was spin purified, digested with BamHI and EcoRI (New England Biolabs) and ligated using the Rapid DNA Ligation kit (Roche) into the dual A. oryzae/E. coli plasmid expression vector pENI1898 that first had been digested with BamHI and EcoRI. pENI1898 is modified from vector pEN11861 (WO 03/070956) as the AMA sequence (Clutterbuck et al., 1991, Gene 98(1): 61-67) has been removed by digestion of the vector with HindIII followed by re-ligation of the agarose gel-purified vector. Further, pENI1861 carries the pyrG gene and is able to complement a pyrG deficient Aspergillus strain.

Following 5 minutes incubation at room temperature the ligation reaction was transformed into competent E. coli TOP10 cells (Invitrogen) which were plated onto LB agar plates containing 150 μg/ml ampicillin. Plates were incubated for 16 hours at 37° C. Plasmid DNA were purified from selected transformants, and sequenced for verification of cloning procedure.

The encoded predicted protein is 248 amino acids and contains a signal peptide of 23 residues and a mature protein of 207 amino acids. The mature sequence of SEQ ID NO: 4 is identical to the mature sequence of SEQ ID NO: 8.

Example 9: Cloning and Expression of Lysozyme GH25 Variants

Variants of GH25 Gene 10 variants containing a single amino acid changes in the synthetic GH25 lysozyme gene were cloned and expressed.

The variants of the GH25 lysozyme consist of the single substitution as follows: W10H, Y28M, S39D, G92P, A93M, E97A, V133M, T142N, F178I or D190A.

Cloning of Variants of GH25

To generate the GH25 variants as described above, PCR-based site-directed mutagenesis was done with mutagenic primers that introduced the desired sequence change (substitutions). Primers were designed so that the mutation lies in the middle of the oligonucleotide with sufficient flanking nucleotides (15-25). The plasmid DNA containing GH25 was used as template and PCR was setup with a proofreading DNA polymerase (Phusion DNA polymerase (New England Biolabs). The PCR products were used to transform competent E. coli TOP 10 cells (Invitrogen) according to the instructions from the manufacturer. Plasmid DNA was isolated from monoclonal transformed E. coli strains, and sequenced to verify the presence of the desired substitution.

Transformation and Expression of GH25 and Variants

The plasmid DNA pENI1898 encoding the lysozyme gene was used for transformation into A. oryzae ToC1512 protoplasts (WO 2005/070962) as described in example 2 and plated onto NaNO₃ sucrose plates without uridine for selection of transformants carrying correct constructs. Plates were incubated 72 hours at 37° C.

Single colonies were isolated by restreaking colonies on NaNO₃ sucrose plates for 72 hours at 37° C. and grown in YP media at 34° C. for 72 hours. Colonies expressing lysozyme were selected after examination of broths by the tubidity assay in 50 mM 3,3 dimethylglutaric acid at pH 6.4 with *Micrococcus lysodeikticus* cell walls as substrates. Further, expression of lysozyme was confirmed by visual inspection of a band of approximately 23 KDa by SDS-PAGE analysis.

Transformants expressing lysozyme were restreaked and grown on COVE N-gly slants at 37° C. for another 5 days and inoculated to 200 ml of G2-Gly shaking flask. After the cultivation with vigorous agitation at 30° C. for 1 day, 3 ml of each culture was transferred to 200 ml of MDU-2Bp in shaking flask to cultivate at 30° C. for 3 days. Culture broths were purified in a similar manor to the purification of the P242M9 GH25 lysozyme in example 6 above.

Example 10: Antimicrobial Activity

The antimicrobial activity of the P242M9 GH25 lysozyme, the synthetic GH25 lysozyme and 11 variants of the synthetic GH25 lysozyme were tested against two *Clostridium perfringens* strains.

Method and Materials

The activity was determined by both measuring the optical density and the number of colony forming units of *Cl. perfringens* cultures before and after exposure to lysozyme. Exposure of *Cl. perfringens* to active lysozymes will result in a kill of the bacteria and a corresponding decrease in both optical density (OD-drop) and the number of colony forming units.

Briefly, lysozyme stock solutions were diluted in PBS (pH 6) to concentrations of 50 µg/ml. Two-fold dilution series of these 50 µg/ml solutions were performed in PBS (pH 6) to end concentrations of 0.4 µg/ml.

Then overnight cultures of *Cl. perfringens* were re-suspended in PBS (pH 6). $OD_{546}$ was measured and adjusted to 1. Cultures (75 µl) were mixed in micro-titre plates (Nunc) 1:1 with prepared lysozyme-solutions (75 µl), which resulted in exposure of *Cl. perfringens* to end concentrations of lysozymes ranging from 0.4-25 µg/ml (7 concentrations in total pr. lysozyme). Cultures were exposed to lysozymes for 4 hours under anaerobic conditions at 42° C. $OD_{546}$ and CFU/ml were measured at time points 0 and 4 hours post-exposure.

Results

The results of the activity testing are shown in tables 9, 10 and 11 and FIGS. 4 and 5. Table 9 shows the decrease in colony forming units of two strains of *Clostridium perfringens* per mL (CFU/mL) of GH25 lysozyme or variant. Exposure to active lysozymes resulted typically in 1-2 log reductions in CFU/mL. Lysozyme activity was evaluated as significant if reduction in CFU/ml was >1 log.

Table 10 shows the optical density drop (delta OD) of *Clostridium perfringens* NN01260 upon exposure to the GH25 lysozyme P242M9 (SEQ ID NO: 4), the synthetic GH25 lysozyme (SEQ ID NO: 8) or 11 variants of SEQ ID NO: 8. Table 11 shows the optical density drop (delta OD) of *Clostridium perfringens* clinical isolate upon exposure to the GH25 lysozyme P242M9 (SEQ ID NO: 4), the synthetic GH25 lysozyme (SEQ ID NO: 8) or 11 variants of SEQ ID NO: 8.

TABLE 9

Decrease in CFU/mL of *Clostridium perfringens* when treated with Wild Type and Variant GH25 Lysozymes

| | Decrease in CFU/mL | |
|---|---|---|
| GH25 Wild Type or Variant | *Cl. perfringens* (NNO11260) | *Cl. perfringens* - clinical isolate from chickens |
| SEQ ID NO: 4 | ++ | ++ |
| V133M | ++ | + |
| W10H | ++ | + |
| S39D | ++ | + |
| F178I | ++ | ++ |
| SEQ ID NO: 8 | ++ | ++ |
| Y28M | ++ | ++ |
| D95A | ++ | + |
| G92P | + | + |
| E97A | − | − |
| D190A | (+) | (+) |
| A93M | + | (+) |
| T142N | + | (+) |

++ significant activity within the whole range of lysozyme concentrations tested.

+ significant activity for a reduced number of lysozyme concentrations tested.

− no significant activity of the lysozyme.

TABLE 10

OD-Drop of *Clostridium perfringens* NN011260 when treated with Wild Type and Variant GH25 Lysozymes

| GH25 Wild Type or Variant | Concentration of *Cl. Perfringens* NN011260 (μg/ml)* | | | | | | | |
|---|---|---|---|---|---|---|---|---|
| | 25 | | 6.25 | | 1.56 | | 0.39 | |
| | Delta $OD_{546}$ | SD | Delta $OD_{546}$ | SD | Delta $OD_{546}$ | SD | Delta $OD_{546}$ | SD |
| SEQ ID NO: 4 | 0.090 | 0.006 | 0.093 | 0.005 | 0.075 | 0.010 | 0.061 | 0.004 |
| V133M | 0.081 | 0.007 | 0.101 | 0.004 | 0.076 | 0.009 | 0.058 | 0.005 |
| W10H | 0.074 | 0.004 | 0.077 | 0.018 | 0.062 | 0.005 | 0.043 | 0.006 |
| S39D | 0.087 | 0.014 | 0.083 | 0.007 | 0.073 | 0.012 | 0.067 | 0.010 |
| F178I | 0.087 | 0.008 | 0.090 | 0.013 | 0.091 | 0.009 | 0.065 | 0.014 |
| SEQ ID NO: 8 | 0.098 | 0.011 | 0.082 | 0.001 | 0.083 | 0.014 | 0.086 | 0.015 |
| Y28M | 0.086 | 0.013 | 0.081 | 0.004 | 0.080 | 0.017 | 0.075 | 0.014 |
| D95A | 0.066 | 0.007 | 0.088 | 0.008 | 0.082 | 0.007 | 0.073 | 0.010 |
| G92P | 0.069 | 0.004 | 0.062 | 0.004 | 0.043 | 0.009 | 0.047 | 0.009 |
| E97A | 0.019 | 0.005 | 0.030 | 0.008 | 0.013 | 0.005 | 0.024 | 0.012 |
| D190A | 0.077 | 0.004 | 0.089 | 0.007 | 0.059 | 0.007 | 0.055 | 0.005 |
| A93M | 0.069 | 0.003 | 0.077 | 0.004 | 0.063 | 0.004 | 0.043 | 0.005 |
| T142N | 0.064 | 0.008 | 0.073 | 0.008 | 0.051 | 0.004 | 0.020 | 0.003 |

*Average of three biological replicates

TABLE 11

OD-Drop of *Clostridium perfringens* clinical isolate when treated with Wild Type and Variant GH25 Lysozymes

| GH25 Wild Type or Variant | Concentration of *Cl. Perfringens* clinical strain (μg/ml)* | | | | | | | |
|---|---|---|---|---|---|---|---|---|
| | 25 | | 6.25 | | 1.56 | | 0.39 | |
| | Delta $OD_{546}$ | SD | Delta $OD_{546}$ | SD | Delta $OD_{546}$ | SD | Delta $OD_{546}$ | SD |
| SEQ ID NO: 4 | 0.068 | 0.014 | 0.062 | 0.012 | 0.028 | 0.021 | 0.009 | 0.003 |
| V133M | 0.060 | 0.010 | 0.050 | 0.009 | 0.016 | 0.009 | −0.001 | 0.006 |
| W10H | 0.050 | 0.018 | 0.024 | 0.029 | 0.007 | 0.016 | −0.005 | 0.011 |
| S39D | 0.058 | 0.016 | 0.047 | 0.006 | 0.025 | 0.015 | 0.003 | 0.006 |
| F178I | 0.070 | 0.015 | 0.068 | 0.018 | 0.033 | 0.010 | 0.008 | 0.005 |
| SEQ ID NO: 8 | 0.073 | 0.015 | 0.060 | 0.013 | 0.042 | 0.018 | 0.011 | 0.008 |
| Y28M | 0.064 | 0.015 | 0.065 | 0.013 | 0.047 | 0.026 | 0.014 | 0.017 |
| D95A | 0.060 | 0.014 | 0.059 | 0.010 | 0.027 | 0.019 | 0.011 | 0.015 |
| G92P | 0.049 | 0.021 | 0.025 | 0.022 | 0.008 | 0.010 | 0.002 | 0.001 |
| E97A | 0.002 | 0.012 | 0.009 | 0.019 | 0.001 | 0.011 | 0.007 | 0.008 |
| D190A | 0.049 | 0.018 | 0.028 | 0.016 | 0.019 | 0.024 | 0.005 | 0.009 |
| A93M | 0.059 | 0.012 | 0.038 | 0.024 | 0.007 | 0.020 | 0.006 | 0.017 |
| T142N | 0.063 | 0.012 | 0.036 | 0.017 | 0.015 | 0.034 | −0.002 | 0.024 |

*Average of three biological replicates

The results show that the mutation of 9 positions did not result in the loss of lysozyme activity. However, mutation of position 97 resulted in loss of activity indicating that this position cannot be mutated.

Example 11: pH Activity Profile

The pH activity profile of the lysozyme of the invention was determined by measuring the decrease (drop) in absorbance/optical density of a solution of resuspended *Micrococcus luteus* ATTC No. 4698 (Sigma-Aldrich M3770) measured in a spectrophotometer at 540 nm for a range of pH values in order to determine at which pH the GH25 lysozyme or variant has peak lysozyme activity.

The *Micrococcus luteus* substrate was prepared as described in example 6. The lysozyme antimicrobial activity was measured as described in example 6 except that the citric acid—phosphate buffer was adjusted to one of the following pH values with HCl or NaOH prior to beginning the experiment: 3.0, 3.5, 4.0, 4.5, 5.0, 5.5, 6.0, 6.5 and 7.0.

The experiment described above was performed in duplicates or triplicates and the results are given in table 12 below.

TABLE 12 pH Activity Profile of Wild Type and Variant GH25 Lysozymes

| GH25 Wild Type or Variant | pH of Peak Antimicrobial Activity |
|---|---|
| SEQ ID NO: 4 | 4.0 |
| V133M | 4.0 |
| W10H | 4.5 |
| S39D | 4.5 |
| F178I | 4.0 |
| SEQ ID NO: 8 | 4.0 |
| Y28M | 4.0 |
| D95A | 4.0 |
| G92P | 4.0 |
| E97A | no activity found |
| D190A | no activity found |

TABLE 12-continued pH Activity Profile of Wild Type and Variant GH25 Lysozymes

| GH25 Wild Type or Variant | pH of Peak Antimicrobial Activity |
|---|---|
| A93M | 4.0 |
| T142N | 4.0 |

The results show that GH25 lysozyme variants of the invention having the substitution Y28M, G92P, A93M, V133M, T142N or F178I retained antimicrobial activity without significant change in the pH activity profile compared to the wild type lysozyme. GH25 lysozyme variants of the invention having the substitution W10H or S39D resulted in an altered pH profile, such that the pH profile increased by 0.5 pH unit, whilst retaining antimicrobial activity.

Example 12: Gastric Stability

The activity of Hen egg white lysozyme, *A. alcalophilum* GH25 lysozyme (SEQ ID NO: 8 and two variants (W10H and S39D)) were activity tested by the turbidity assay after incubation for up to 1 hour in artificial gastric juice (pH 2) containing pepsin. This activity was then compared to a standard curve made for each lysozyme under the same or equivalent conditions but without incubation with gastric juice containing pepsin.

The different lysozymes were incubated in artificial gastric juice for a time span of 0, 15, 30 or 60 minutes. After incubation, a stop buffer was added to raise pH and thereby prevent the low pH and pepsin from degrading peptide bonds of the lysozyme. After deactivation of pepsin, an activity turbidity assay was performed together with a standard curve of different concentrations of the lysozyme in question for comparison.

Artificial Gastric Juice: (HCl pH 2, 1 mg/ml Pepsin, 0.1 M NaCl).
Solution A: 0.01 M HCl, 0.1 M NaCl (prepared by mixing 275 µl 1M HCl with 2.5 ml 1 M NaCl and adding 22.23 ml MQ water to a total volume of 25 ml).
Solution B: 0.01 M HCl, 0.1 M NaCl, 10 mg/ml pepsin (prepared by weighing out 50 mg pepsin and adding 5 ml solution A).
Preparation of Standard Curve Artificial gastric juice (160 µl) was added to each microtiter well followed by 20 µl citric acid—phosphate buffer (pH 7 for hen egg white lysozyme, pH 4 for *A. alcalophilum* GH25 lysozyme and pH 4.5 for the variants W10H and S39D). The lysozyme solution (20 µl) was added then *Micrococcus luteus* substrate (20 µl, prepared as described in example 6) was added to each well (standard curve as well as time series samples) and the OD 540 nm was measured each minute for one hour at 37° C.

The lysozyme antimicrobial activity was measured as described in example 6 except that the citric acid—phosphate buffer was adjusted to the optimal pH for the different lysozymes (as given in the previous paragraph) by addition of HCl or NaOH. The experiment described above was performed in duplicates and the results are given in table 13 below.

TABLE 13

Residual activity of lysozyme after incubation with artificial gastric juice

| | Residual activity (minutes) | | | |
|---|---|---|---|---|
| Lysozyme | 0 min | 15 min | 30 min | 60 min |
| Hen egg white lysozyme | 100% | 56% | 30% | 7% |
| *Acremonium alcalophilum* GH25 lysozyme | 100% | 109% | 109% | 102% |
| *Acremonium alcalophilum* GH25 lysozyme variant W10H | 100% | 97% | 97% | 101% |
| *Acremonium alcalophilum* GH25 lysozyme variant S39D | 100% | 99% | 93% | 89% |

The remaining lysozyme activity after incubation in artificial gastric juice was dramatic reduced for hen egg white lysozymes even after 15 minutes. In comparison, the GH25 lysozyme from *Acremonium alcalophilum* showed no reduction in activity. In addition, the two GH25 variants having the substitution W10H or S39D also retained lysozyme activity, showing similar residual activity as the GH25 lysozymes from *Acremonium alcalophilum*.

Example 13: Isolation of Genomic DNA

The yield of bacterial genomic DNA purifications with added *Acremonium alcalophilum* GH25 lysozyme (SEQ ID NO. 8) and a combination of hen egg white lysozyme and *Acremonium alcalophilum* GH25 lysozyme (SEQ ID NO. 8) were compared to DNA purification without lysozyme and with hen egg white lysozyme alone. Genomic DNA was isolated from five different bacteria.

Method

Bacterial mass was obtained either by scraping off cells from an agar plate with an inoculation loop or by centrifugation of a liquid culture (see table 14). DNA was isolated using a modified version of the QIAamp DNA Blood Mini Kit (Cat. No 51106) and purified either using a Qiagen QIAcube or a manual process.

TABLE 14

Overview of bacterial strains tested, cell starting material and purification method.

| Bacterial strain | DSMZ No.: | Cell starting material | Purification method |
|---|---|---|---|
| *Micrococcus luteus* | DSM20030 | Colony scrape | QIAcube with Qiagen kit #51106 |
| *Bacillus subtilis* | DSM3256 | Colony scrape | QIAcube with Qiagen kit #51106 |
| *Zobillia uliginosa* | DSM2061 | Liquid culture | Qiagen kit #51106 |
| *Streptomyces coelicolor* | DSM40233 | Liquid culture | Qiagen kit #51106 |
| *Celluphaga lytica* | DSM2039 | Colony scrape | Qiagen kit #51106 |
| *Streptomyces mobaraensis* | DSM40847 | Liquid culture | Qiagen kit #51106 |

DNA Isolation Using QIAcube:

A colony scrape fitting a 10 µL inoculation loop was resupended in 3 mL M9 buffer (prepared by dissolving 8.77 g $Na_2HPO.2H_2O$, 3 g $KH_2PO_4$, 4 g NaCl and 0.2 g $MgSO_4.7H_2O$ in 1000 mL $H_2O$ and adjusting the pH to 7 with NaOH or HCl). The solution was centrifuged for 5 min at 3000 RPM and the pellet was resuspended in 3 mL P1 buffer (included in Qiagen kit #51106). 200 µL aliquots were added to 12 2 mL tubes and 15 µL of water, *A. alcalophilum* GH25 lysozyme (10 mg/mL), Hen egg white lysozyme (10 mg/mL) or *A. alcalophilum* GH25 lysozyme (10 mg/mL)+ hen egg white (10 mg/mL) 1:1 mix were added to tubes in triplicates. Tubes were placed in the QIAcube and processed according to Qiagens recommendations.

Manual DNA Isolation:

Liquid culture pellets and colony scrape were resuspended in 3 mL M9 buffer. Bacterial M9 buffer suspensions were centrifuged for 5 min at 3000 RPM and pellets were resuspended in 3 mL P1 buffer. 200 µL aliquots were added to 12 2 mL tubes and 15 µL of water, *A. alcalophilum* GH25 lysozyme (10 mg/mL), Hen egg white lysozyme (10 mg/mL) or *A. alcalophilum* GH25 lysozyme (10 mg/mL)+ hen egg white (10 mg/mL) 1:1 mix were added to tubes in triplicates. Tubes were incubated at 37° C. for 30 min after which 25 µL Qiagen Protease and 200 µL Qiagen buffer AL were added. The tubes were then incubated at 56° C. for 20 min. 210 µL 96% ethanol were next added to each tube. The tubes were vortexed and liquids were transferred to Qiagen spin columns and centrifuged at 8000 rpm for 1 min. The columns were washed twice with 500 µl AW1 buffer (included in Qiagen kit #51106). After the first wash, the columns were centrifuged for 1 min at 8000 RPM and after the second wash, the columns were centrifuged for 3 min at 15000 RPM. Genomic DNA was eluted from column by addition by 100 µL milliQ water (heated to 70° C.) to each column, incubated for 1 min at room temperature and centrifuged into Eppendorf tubes at 8000 RPM for 1 min. All incubations were repeated in triplicate.

Results

The yield of genomic DNA yield was estimated by running the isolated DNA on an agarose gel and visually inspecting the intensity of the DNA band (table 15). The relative DNA yield between the 4 different treatments of each bacterial strain was estimated by eye using 4 different scores.

TABLE 15

Comparison of the Genomic DNA yield between different combinations of *Acremonium alcalophilum* GH25 lysozyme (SEQ ID NO. 8) and hen egg white lysozyme

| Bacterial strain | No lysozyme | *A. alcalophilum* GH25 lysozyme | Hen egg white | *A. alcalophilum* GH25 lysozyme and hen egg white |
|---|---|---|---|---|
| *Micrococcus luteus* | − | ++ | +++ | +++ |
| *Bacillus subtilis* | − | + | +++ | ++ |
| *Zobillia uliginosa* | ++ | +++ | +++ | +++ |
| *Streptomyces coelicolor* | − | − | + | + |
| *Celluphaga lytica* | +++ | +++ | +++ | +++ |
| *Streptomyces mobaraensis* | − | ++ | + | +++ |

Yields were scored by eye using the following scale:
− no DNA band visible
+ weak band
++ medium band
+++ strong band.

The use of *A. alcalophilum* GH25 lysozyme gave as good as or better yield of genomic DNA in 3 out of 6 cases compared to hen egg lysozyme. The use of the combination of *A. alcalophilum* GH25 lysozyme and hen egg lysozyme gave as good as or better yield of genomic DNA in 5 out of 6 cases compared to either lysozyme alone.

The invention claimed is:

1. A method of feeding an animal, comprising administering a polypeptide having lysozyme activity to the animal, wherein the polypeptide has at least 90% sequence identity to the polypeptide of amino acids 1 to 208 of SEQ ID NO: 8.

2. The method of claim 1, wherein the polypeptide has at least 92% sequence identity to the polypeptide sequence of amino acids 1 to 208 of SEQ ID NO: 8.

3. The method of claim 1, wherein the polypeptide has at least 95% sequence identity to the polypeptide sequence of amino acids 1 to 208 of SEQ ID NO: 8.

4. The method of claim 1, wherein the polypeptide has at least 97% sequence identity to the polypeptide sequence of amino acids 1 to 208 of SEQ ID NO: 8.

5. The method of claim 1, wherein the polypeptide is encoded by a polynucleotide that hybridizes under high stringency conditions with the mature polypeptide coding sequence of SEQ ID NO: 3 or SEQ ID NO: 7, or the full-length complement of thereof, and has at least 90% sequence identity to the polypeptide sequence of amino acids 1 to 208 of SEQ ID NO: 8.

6. The method of claim 1, wherein the polypeptide is a variant of the polypeptide sequence of amino acids 1 to 208 of SEQ ID NO: 8, comprising a substitution, deletion, and/or insertion at one or more positions, and has at least 90% sequence identity to the polypeptide sequence of amino acids 1 to 208 of SEQ ID NO: 8.

7. The method of claim 1, wherein the polypeptide is a fragment of the polypeptide sequence of amino acids 1 to 208 of SEQ ID NO: 8, which has lysozyme activity and has at least 90% sequence identity to the polypeptide sequence of amino acids 1 to 208 of SEQ ID NO: 8.

8. The method of claim 1, wherein the polypeptide comprises amino acids 1 to 208 of SEQ ID NO: 8.

9. The method of claim 1, wherein the polypeptide consists of amino acids 1 to 208 of SEQ ID NO: 8.

10. The method of claim 1, wherein the animal is selected from the group consisting of sheep, goats, cattle, deer, pigs or swine, poultry; horses, and fish.

11. The method of claim 1, wherein the animal is selected from the group consisting of beef cattle, cows, and young calves.

12. The method of claim 1, wherein the animal is selected from the group consisting of geese, turkeys, ducks and chicken.

13. The method of claim 1, wherein the animal is selected from the group consisting of broilers, chicks and layers.

14. The method of claim 1, wherein the administering of the polypeptide having lysozyme activity improves animal performance.

15. The method of claim 1, wherein the administering of the polypeptide having lysozyme activity suppresses growth or intestinal colonization of a viral pathogen, parasitic pathogen or bacterial pathogen.

16. The method of claim 15, wherein the administering of the polypeptide having lysozyme activity suppresses growth or intestinal colonization of coccidian protozoa, *Eimeria maxima*, or *Eimeria mitis*.

17. The method of claim 15, wherein the administering of the polypeptide having lysozyme activity suppresses growth or intestinal colonization of *Clostridium perfringens, Escherichia coli, Campylobacter coli, C. hyointestinalis, C. jejuni, Yersinia* ssp., *Treponema suis, Brachyspira hyodysenteriae, Lawsonia intracellularis* or *Salmonella*.

18. The method of claim 15, wherein the animal is chicken and the administering of the polypeptide having lysozyme activity suppresses growth or intestinal colonization of *Clostridium perfringens*.

19. The method of claim 1, wherein the polypeptide having lysozyme activity is administered to the animal in an animal feed or animal feed additive, which comprises at least one fat-soluble vitamin, and/or at least one water soluble vitamin, and/or at least one trace mineral, and/or at least one macro mineral.

20. The method of claim 19, wherein the animal feed or animal feed additive further comprises at least one other enzyme selected from the group consisting of phytase (EC 3.1.3.8 or 3.1.3.26); xylanase (EC 3.2.1.8); galactanase (EC 3.2.1.89); alpha-galactosidase (EC 3.2.1.22); protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and amylase.

21. The method of claim 19, wherein the animal feed or animal feed additive further comprises maize, sorghum, wheat, barley, oats, soybean meal, fish meal, meat and bone meal; and/or whey.

* * * * *

SEQUENCE LISTING

```
<160> NUMBER OF SEQ ID NOS: 10

<210> SEQ ID NO 1
<211> LENGTH: 782
<212> TYPE: DNA
<213> ORGANISM: Acremonium alcalophilum
<220> FEATURE:
<221> NAME/KEY: CDS
<222> LOCATION: (1)..(133)
<220> FEATURE:
<221> NAME/KEY: sig_peptide
<222> LOCATION: (1)..(57)
<220> FEATURE:
<221> NAME/KEY: CDS
<222> LOCATION: (215)..(345)
<220> FEATURE:
<221> NAME/KEY: CDS
<222> LOCATION: (516)..(779)

<400> SEQUENCE: 1 atg gtc tct ttc aag cag ctc gcc ctc ctg gca ctg ggc gcc gtc caa        48
Met Val Ser Phe Lys Gln Leu Ala Leu Leu Ala Leu Gly Ala Val Gln
1               5                   10                  15 gta cag gcg cag tgc gtc ggc ccg gct atc aat tcc gcg gct ctt aac        96
Val Gln Ala Gln Cys Val Gly Pro Ala Ile Asn Ser Ala Ala Leu Asn
            20                  25                  30 ctc atc aag gag ttt gag gga tgg agg ccc aac att t gtgcgttccc          143
Leu Ile Lys Glu Phe Glu Gly Trp Arg Pro Asn Ile
        35                  40 ttctacgtta catcacccag ttcccttgtt attcagacat tatttctata ttcctggcta      203
acactgtaaa g ac cgc gac ccc gtc ggc ctc ccc acc gtc gga tac ggc       252
             Tyr Arg Asp Pro Val Gly Leu Pro Thr Val Gly Tyr Gly
```

```
                    45                  50                  55
cac ctc tgc cgc gac tcg agc tgc tct gac gtc cct tac cca att ccc        300
His Leu Cys Arg Asp Ser Ser Cys Ser Asp Val Pro Tyr Pro Ile Pro
         60                  65                  70 ctg tcc gtt gcc aac ggc gag cgt ctc ctt cgg agc gac cta gcg            345
Leu Ser Val Ala Asn Gly Glu Arg Leu Leu Arg Ser Asp Leu Ala
 75                  80                  85 gtgagtctat cccctttgca cttcataaaa cgtcgccttc tctgttgtca ttctacctgg      405
acagcctccc cctatttctc tcttctatct tttcttcttt cccgttctgc aagcttgacc      465
cctgaccaac catatccacc cagacctacc agaactgcat cacgatgcag acg gcc         521
                                                            Thr Ala
                                                                 90 tcg tcc gtc gtc ctg aat gcg aac cag tac ggc gcc ctg gtc agc tgg        569
Ser Ser Val Val Leu Asn Ala Asn Gln Tyr Gly Ala Leu Val Ser Trp
             95                 100                 105 gcc ttc aac gtc ggc tgc ggc gcc acc agc acg tcg act ctg atc cgc        617
Ala Phe Asn Val Gly Cys Gly Ala Thr Ser Thr Ser Thr Leu Ile Arg
                110                 115                 120 cgc ctc aac gcc gga gag agc ccc aac acc gtc gct gcc cag gag ctg        665
Arg Leu Asn Ala Gly Glu Ser Pro Asn Thr Val Ala Ala Gln Glu Leu
            125                 130                 135 cct cgc tgg aac aag gct ggc ggc cag gtc ctg ccc ggc ctg gtg cgc        713
Pro Arg Trp Asn Lys Ala Gly Gly Gln Val Leu Pro Gly Leu Val Arg
        140                 145                 150 cgc cgt gct gcc gag gta gag ctg cat cgt act tcc acc agt gtc cgt        761
Arg Arg Ala Ala Glu Val Glu Leu His Arg Thr Ser Thr Ser Val Arg
155                 160                 165                 170 gct ctg cct gct tgc tct tag                                            782
Ala Leu Pro Ala Cys Ser
                175

<210> SEQ ID NO 2
<211> LENGTH: 176
<212> TYPE: PRT
<213> ORGANISM: Acremonium alcalophilum

<400> SEQUENCE: 2

Met Val Ser Phe Lys Gln Leu Ala Leu Leu Ala Leu Gly Ala Val Gln
1               5                   10                  15

Val Gln Ala Gln Cys Val Gly Pro Ala Ile Asn Ser Ala Ala Leu Asn
            20                  25                  30

Leu Ile Lys Glu Phe Glu Gly Trp Arg Pro Asn Ile Tyr Arg Asp Pro
        35                  40                  45

Val Gly Leu Pro Thr Val Gly Tyr Gly His Leu Cys Arg Asp Ser Ser
    50                  55                  60

Cys Ser Asp Val Pro Tyr Pro Ile Pro Leu Val Ala Asn Gly Glu
65                  70                  75                  80

Arg Leu Leu Arg Ser Asp Leu Ala Thr Ala Ser Ser Val Val Leu Asn
                85                  90                  95

Ala Asn Gln Tyr Gly Ala Leu Val Ser Trp Ala Phe Asn Val Gly Cys
            100                 105                 110

Gly Ala Thr Ser Thr Ser Thr Leu Ile Arg Arg Leu Asn Ala Gly Glu
        115                 120                 125

Ser Pro Asn Thr Val Ala Ala Gln Glu Leu Pro Arg Trp Asn Lys Ala
    130                 135                 140

Gly Gly Gln Val Leu Pro Gly Leu Val Arg Arg Ala Ala Glu Val
145                 150                 155                 160
```

```
Glu Leu His Arg Thr Ser Thr Ser Val Arg Ala Leu Pro Ala Cys Ser
            165                 170                 175

<210> SEQ ID NO 3
<211> LENGTH: 838
<212> TYPE: DNA
<213> ORGANISM: Acremonium alcalophilum
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: CDS
<222> LOCATION: (302)..(835)

<400> SEQUENCE: 3 atg aag ctt ctt ccc tcc ttg att ggc ctg gcc agt ctg gcg tcc ctc         48
Met Lys Leu Leu Pro Ser Leu Ile Gly Leu Ala Ser Leu Ala Ser Leu
1               5                   10                  15 gcc gtc gcc cgg atc ccc ggc ttt gac att tcg ggc tgg caa ccg acc         96
Ala Val Ala Arg Ile Pro Gly Phe Asp Ile Ser Gly Trp Gln Pro Thr
                20                  25                  30 acc gac ttt gca agg gcg tat gct aat gga gat cgt ttc gtc tac atc        144
Thr Asp Phe Ala Arg Ala Tyr Ala Asn Gly Asp Arg Phe Val Tyr Ile
            35                  40                  45 aag gtacgttcaa ccttgccacc aagttgcgaa cccgagacaa gactgtgacc             197
Lys gcctcctttg ccctggggca gctcacgcac ccagcagcat cccatccccc ggccccccac      257
gtaccaccgg aaagctaaca tcaacccccct accactgcta ccag gcc acc gag ggc      313
                                                  Ala Thr Glu Gly
                                                            50 acc aca ttc aag agc tcc gca ttc agc cgc cag tac acc ggc gca acg        361
Thr Thr Phe Lys Ser Ser Ala Phe Ser Arg Gln Tyr Thr Gly Ala Thr
        55                  60                  65 caa aac ggc ttc atc cgc ggc gcc tac cac ttc gcc cag ccc gcc gcg        409
Gln Asn Gly Phe Ile Arg Gly Ala Tyr His Phe Ala Gln Pro Ala Ala
70                  75                  80                  85 tcc tcg ggc gcc gcg cag gcg aga tac ttc gcc agc aac ggc ggc ggc        457
Ser Ser Gly Ala Ala Gln Ala Arg Tyr Phe Ala Ser Asn Gly Gly Gly
                90                  95                  100 tgg tcc aag gac ggc atc acc ctg ccc ggg gcg ctg gac atc gag tac        505
Trp Ser Lys Asp Gly Ile Thr Leu Pro Gly Ala Leu Asp Ile Glu Tyr
            105                 110                 115 aac ccc aac ggc gcc acc tgc tac ggc ctc tcg caa tcg gcc atg gtg        553
Asn Pro Asn Gly Ala Thr Cys Tyr Gly Leu Ser Gln Ser Ala Met Val
        120                 125                 130 aac tgg atc gag gac ttt gtc acc acc tac cac ggc atc acc tcc cgc        601
Asn Trp Ile Glu Asp Phe Val Thr Thr Tyr His Gly Ile Thr Ser Arg
    135                 140                 145 tgg ccc gtc atc tac acc acc acc gac tgg tgg acc cag tgc acc ggc        649
Trp Pro Val Ile Tyr Thr Thr Thr Asp Trp Trp Thr Gln Cys Thr Gly
150                 155                 160                 165 aac tcc aac cgc ttc gcg aac cgc tgc ccg ctg tgg atc gcc cgc tac        697
Asn Ser Asn Arg Phe Ala Asn Arg Cys Pro Leu Trp Ile Ala Arg Tyr
                170                 175                 180 gcc agc tcc gtc ggc act ctg ccc aat ggc tgg ggc ttt tac acc ttc        745
Ala Ser Ser Val Gly Thr Leu Pro Asn Gly Trp Gly Phe Tyr Thr Phe
            185                 190                 195 tgg cag tac aac gac aag tat cct cag ggc ggt gat tcg aac tgg ttc        793
```

```
Trp Gln Tyr Asn Asp Lys Tyr Pro Gln Gly Gly Asp Ser Asn Trp Phe
            200                 205                 210 aac ggc gat gcg tcg cgt ctc agg gct ctc gct aac gga gac taa          838
Asn Gly Asp Ala Ser Arg Leu Arg Ala Leu Ala Asn Gly Asp
        215                 220                 225

<210> SEQ ID NO 4
<211> LENGTH: 227
<212> TYPE: PRT
<213> ORGANISM: Acremonium alcalophilum

<400> SEQUENCE: 4

Met Lys Leu Leu Pro Ser Leu Ile Gly Leu Ala Ser Leu Ala Ser Leu
1               5                   10                  15

Ala Val Ala Arg Ile Pro Gly Phe Asp Ile Ser Gly Trp Gln Pro Thr
            20                  25                  30

Thr Asp Phe Ala Arg Ala Tyr Ala Asn Gly Asp Arg Phe Val Tyr Ile
        35                  40                  45

Lys Ala Thr Glu Gly Thr Thr Phe Lys Ser Ser Ala Phe Ser Arg Gln
    50                  55                  60

Tyr Thr Gly Ala Thr Gln Asn Gly Phe Ile Arg Gly Ala Tyr His Phe
65                  70                  75                  80

Ala Gln Pro Ala Ala Ser Ser Gly Ala Ala Gln Ala Arg Tyr Phe Ala
                85                  90                  95

Ser Asn Gly Gly Gly Trp Ser Lys Asp Gly Ile Thr Leu Pro Gly Ala
            100                 105                 110

Leu Asp Ile Glu Tyr Asn Pro Asn Gly Ala Thr Cys Tyr Gly Leu Ser
        115                 120                 125

Gln Ser Ala Met Val Asn Trp Ile Glu Asp Phe Val Thr Thr Tyr His
    130                 135                 140

Gly Ile Thr Ser Arg Trp Pro Val Ile Tyr Thr Thr Thr Asp Trp Trp
145                 150                 155                 160

Thr Gln Cys Thr Gly Asn Ser Asn Arg Phe Ala Asn Arg Cys Pro Leu
                165                 170                 175

Trp Ile Ala Arg Tyr Ala Ser Ser Val Gly Thr Leu Pro Asn Gly Trp
            180                 185                 190

Gly Phe Tyr Thr Phe Trp Gln Tyr Asn Asp Lys Tyr Pro Gln Gly Gly
        195                 200                 205

Asp Ser Asn Trp Phe Asn Gly Asp Ala Ser Arg Leu Arg Ala Leu Ala
    210                 215                 220

Asn Gly Asp
225

<210> SEQ ID NO 5
<211> LENGTH: 41
<212> TYPE: DNA
<213> ORGANISM: Artificial sequence
<220> FEATURE:
<223> OTHER INFORMATION: Synthetic construct

<400> SEQUENCE: 5
acacaactgg ggatccacca tgaagcttct tccctccttg a                         41

<210> SEQ ID NO 6
<211> LENGTH: 38
<212> TYPE: DNA
<213> ORGANISM: Artificial sequence
<220> FEATURE:
<223> OTHER INFORMATION: Synthetic construct
```

-continued

<400> SEQUENCE: 6
agatctcgag aagcttatta gtctccgtta gcgagagc                                    38

<210> SEQ ID NO 7
<211> LENGTH: 747
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(744)
<220> FEATURE:
<221> NAME/KEY: sig_peptide
<222> LOCATION: (1)..(69)
<220> FEATURE:
<221> NAME/KEY: mat_peptide
<222> LOCATION: (121)..(744)

<400> SEQUENCE: 7

```
atg aag ttc ttc acc acc atc ctc agc acc gcc agc ctt gtt gct gct      48
Met Lys Phe Phe Thr Thr Ile Leu Ser Thr Ala Ser Leu Val Ala Ala
-40             -35                 -30                 -25 ctc ccc gcc gct gtt gac tcg aac cat acc ccg gcc gct cct gaa ctt      96
Leu Pro Ala Ala Val Asp Ser Asn His Thr Pro Ala Ala Pro Glu Leu
            -20                 -15                 -10 gtt gcc cgg agt cct att cgt cga cgc att ccc gga ttc gat atc tcg     144
Val Ala Arg Ser Pro Ile Arg Arg Arg Ile Pro Gly Phe Asp Ile Ser
        -5              -1  1               5 gga tgg cag ccg acg acg gac ttc gca agg gcg tac gca aac gga gac     192
Gly Trp Gln Pro Thr Thr Asp Phe Ala Arg Ala Tyr Ala Asn Gly Asp
    10                  15                  20 cga ttc gtg tac atc aag gca aca gag gga aca aca ttc aaa tcg tcg     240
Arg Phe Val Tyr Ile Lys Ala Thr Glu Gly Thr Thr Phe Lys Ser Ser
25                  30                  35                  40 gca ttc tcc agg cag tac acc gga gca acc cag aac ggc ttc atc cga     288
Ala Phe Ser Arg Gln Tyr Thr Gly Ala Thr Gln Asn Gly Phe Ile Arg
                45                  50                  55 gga gcc tac cac ttc gcc cag cct gca gcc tcc tcg gga gca gcc cag     336
Gly Ala Tyr His Phe Ala Gln Pro Ala Ala Ser Ser Gly Ala Ala Gln
            60                  65                  70 gca agg tac ttc gca tcg aac ggt ggc ggt tgg tcc aag gac ggt atc     384
Ala Arg Tyr Phe Ala Ser Asn Gly Gly Gly Trp Ser Lys Asp Gly Ile
        75                  80                  85 acc ctc cct ggt gcc ttg gat atc gag tac aac ccc aac gga gca aca     432
Thr Leu Pro Gly Ala Leu Asp Ile Glu Tyr Asn Pro Asn Gly Ala Thr
    90                  95                  100 tgt tat ggt ctc tcg cag tcg gcg atg gtg aac tgg att gag gac ttc     480
Cys Tyr Gly Leu Ser Gln Ser Ala Met Val Asn Trp Ile Glu Asp Phe
105                 110                 115                 120 gtg aca acc tac cac ggc atc acc tcg agg tgg cct gtg atc tac acc     528
Val Thr Thr Tyr His Gly Ile Thr Ser Arg Trp Pro Val Ile Tyr Thr
                125                 130                 135 aca acc gac tgg tgg acg cag tgt acc ggc aac tcc aac cga ttc gcg     576
Thr Thr Asp Trp Trp Thr Gln Cys Thr Gly Asn Ser Asn Arg Phe Ala
            140                 145                 150 aac agg tgt ccg ctc tgg atc gcg agg tat gcc tcc tcc gtc ggc acc     624
Asn Arg Cys Pro Leu Trp Ile Ala Arg Tyr Ala Ser Ser Val Gly Thr
        155                 160                 165 ctc ccg aac gga tgg ggc ttc tat acc ttc tgg cag tac aac gat aag     672
Leu Pro Asn Gly Trp Gly Phe Tyr Thr Phe Trp Gln Tyr Asn Asp Lys
    170                 175                 180
```

```
tac ccc cag gga gga gat tcc aac tgg ttc aac ggt gat gca tcg agg      720
Tyr Pro Gln Gly Gly Asp Ser Asn Trp Phe Asn Gly Asp Ala Ser Arg
185             190                 195                 200 ctc agg gca ttg gcg aac ggc gat tag                                   747
Leu Arg Ala Leu Ala Asn Gly Asp
                205
```

<210> SEQ ID NO 8
<211> LENGTH: 248
<212> TYPE: PRT
<213> ORGANISM: Artificial sequence
<220> FEATURE:
<223> OTHER INFORMATION: Synthetic Construct

<400> SEQUENCE: 8

```
Met Lys Phe Phe Thr Thr Ile Leu Ser Thr Ala Ser Leu Val Ala Ala
-40             -35                 -30                 -25

Leu Pro Ala Ala Val Asp Ser Asn His Thr Pro Ala Ala Pro Glu Leu
                -20                 -15                 -10

Val Ala Arg Ser Pro Ile Arg Arg Ile Pro Gly Phe Asp Ile Ser
                -5              -1  1               5

Gly Trp Gln Pro Thr Thr Asp Phe Ala Arg Ala Tyr Ala Asn Gly Asp
10                  15                  20

Arg Phe Val Tyr Ile Lys Ala Thr Glu Gly Thr Thr Phe Lys Ser Ser
25                  30                  35                  40

Ala Phe Ser Arg Gln Tyr Thr Gly Ala Thr Gln Asn Gly Phe Ile Arg
                45                  50                  55

Gly Ala Tyr His Phe Ala Gln Pro Ala Ser Ser Gly Ala Ala Gln
                60                  65                  70

Ala Arg Tyr Phe Ala Ser Asn Gly Gly Gly Trp Ser Lys Asp Gly Ile
                75                  80                  85

Thr Leu Pro Gly Ala Leu Asp Ile Glu Tyr Asn Pro Asn Gly Ala Thr
                90                  95                  100

Cys Tyr Gly Leu Ser Gln Ser Ala Met Val Asn Trp Ile Glu Asp Phe
105                 110                 115                 120

Val Thr Thr Tyr His Gly Ile Thr Ser Arg Trp Pro Val Ile Tyr Thr
                125                 130                 135

Thr Thr Asp Trp Trp Thr Gln Cys Thr Gly Asn Ser Asn Arg Phe Ala
                140                 145                 150

Asn Arg Cys Pro Leu Trp Ile Ala Arg Tyr Ala Ser Ser Val Gly Thr
                155                 160                 165

Leu Pro Asn Gly Trp Gly Phe Tyr Thr Phe Trp Gln Tyr Asn Asp Lys
                170                 175                 180

Tyr Pro Gln Gly Gly Asp Ser Asn Trp Phe Asn Gly Asp Ala Ser Arg
185                 190                 195                 200

Leu Arg Ala Leu Ala Asn Gly Asp
                205
```

<210> SEQ ID NO 9
<211> LENGTH: 46
<212> TYPE: DNA
<213> ORGANISM: Artificial sequence
<220> FEATURE:
<223> OTHER INFORMATION: Synthetic construct

<400> SEQUENCE: 9
tacacaactg gggatccagc ggccgcacca tgaagttctt caccac          46

```
<210> SEQ ID NO 10
<211> LENGTH: 37
<212> TYPE: DNA
<213> ORGANISM: Artificial sequence
<220> FEATURE:
<223> OTHER INFORMATION: Synthetic construct

<400> SEQUENCE: 10
atacttgtcc gaattcctaa tcgccgttcg ccaatgc                                37
```